US006355810B1

(12) United States Patent
Griffin et al.

(10) Patent No.: US 6,355,810 B1
(45) Date of Patent: Mar. 12, 2002

(54) MULTIBINDING INHIBITORS OF HMG-COA REDUCTASE

(75) Inventors: John H. Griffin, Atherton; Michael R. Leadbetter, San Leandro; Donald E. Schmidt, Jr., Brisbane, all of CA (US)

(73) Assignee: Advanced Medicine, Inc., South San Francisco, CA (US)

( * ) Notice: Subject to any disclaimer, the term of this patent is extended or adjusted under 35 U.S.C. 154(b) by 0 days.

(21) Appl. No.: 09/325,663

(22) Filed: Jun. 4, 1999

Related U.S. Application Data

(60) Provisional application No. 60/088,448, filed on Jun. 8, 1998, provisional application No. 60/093,072, filed on Jul. 16, 1998, and provisional application No. 60/114,083, filed on Dec. 28, 1998.

(51) Int. Cl.$^7$ .................... C07D 207/04; C07D 405/00; C07D 333/00; C07D 213/04; A61K 31/40
(52) U.S. Cl. .................. 548/574; 435/7.1; 435/7.2; 436/501; 436/518; 514/99; 514/414; 514/427; 514/428; 514/460; 546/255; 546/267; 548/517; 548/562; 548/577; 548/400; 548/414; 548/494; 549/6; 549/60; 549/216; 549/264; 549/292
(58) Field of Search ................................ 424/1.11, 9.1, 424/178.1, 193.1; 435/7.1, 7.2; 436/501, 518; 514/99, 414, 460, 427, 428; 549/6, 60, 216, 264, 292; 548/400, 414, 494, 574, 517, 562, 577; 530/345, 389.1, 402, 807; 546/255, 267

(56) References Cited

U.S. PATENT DOCUMENTS

| 4,739,073 A | 4/1988 | Kathawala |
| 4,963,538 A | 10/1990 | Duggan et al. |
| 5,294,724 A | 3/1994 | Jendralla et al. |
| 5,463,564 A | 10/1995 | Agrafiotis et al. |

FOREIGN PATENT DOCUMENTS

| EP | 0 251 625 A2 | 1/1988 |
| EP | 0 251 625 B1 | 5/1991 |
| WO | 92/05802 A1 | 4/1992 |
| WO | 97/35195 A1 | 9/1997 |

OTHER PUBLICATIONS

Portoghese, J. Med. Chem. 1992, 35(11), 1927–1937.
Zeng et al., J. Chrom. A. 1998, 794, 3–13.
G. Beck et al., *J. Med. Chem.* 1990, 33, 52–60.
J. D. Bergstrom et al., Biochim. Biophys. Acta 1998, 1389, 213–221.
H. Bischoff et al., *Atherosclerosis* 1997, 135, 119–130.
C.B. Blum, *J. Cardiol* 1994, 73, 3D–11D.
C. Chan et al., *J. Med. Chem.* 1993, 36, 3646–3657.
P.H. Chong et al., *Pharmacotherapy* 1997, 17, 1157–1177.
A. Endo et al., *FEBS Letters* 1976, 72, 323–326.
D.S. Karanewsky et al., *J. Med. Chem.* 1990, 33, 2952–2956.
C.M. Lawrence et al., *Science* 1995, 268, 1758–1762.
P. Louis–Flamberg et al., *Biochemistry* 1990, 29, 4115–4120.
C.E. Nakamura et al., *Biochemistry* 1985, 24, 1364–1376.
J. Robl et al., *J. Med. Chem.* 1991, 34, 2804–2815.
B.D. Roth et al., *J. Med. Chem.* 1990, 34, 357–366.
S.B. Shuker et al., *Science* 1996, 274, 1531–1534.
D.R. Sliskovic et al., *J. Med. Chem.* 1991, 34, 367–373.

*Primary Examiner*—Jyothsna Venkat
*Assistant Examiner*—Maurie E. Garcia
(74) *Attorney, Agent, or Firm*—David E. Boone; Jeffrey A. Hagenah

(57) ABSTRACT

Disclosed are multibinding compounds which inhibit 3-hydroxy-3-methylglutaryl coenzyme A reductase (HMG-COA reductase), the rate limiting enzyme in cholesterol biosynthesis. The multibinding compounds of this invention containing from 2 to 10 ligands covalently attached to one or more linkers. Each ligand is a moiety capable of binding to HMG-CoA reductase and the distance between ligands is at least 10 Å. The multibinding compounds of this invention are useful in the treatment and prevention of hypercholesterolemia, hyperlipidemia, atherosclerosis and the like.

8 Claims, 13 Drawing Sheets

Mevastatin compactin

Lovastatin

Simvastatin

Pravastatin

Atrovastatin    Fluvastatin    Cerivastatin

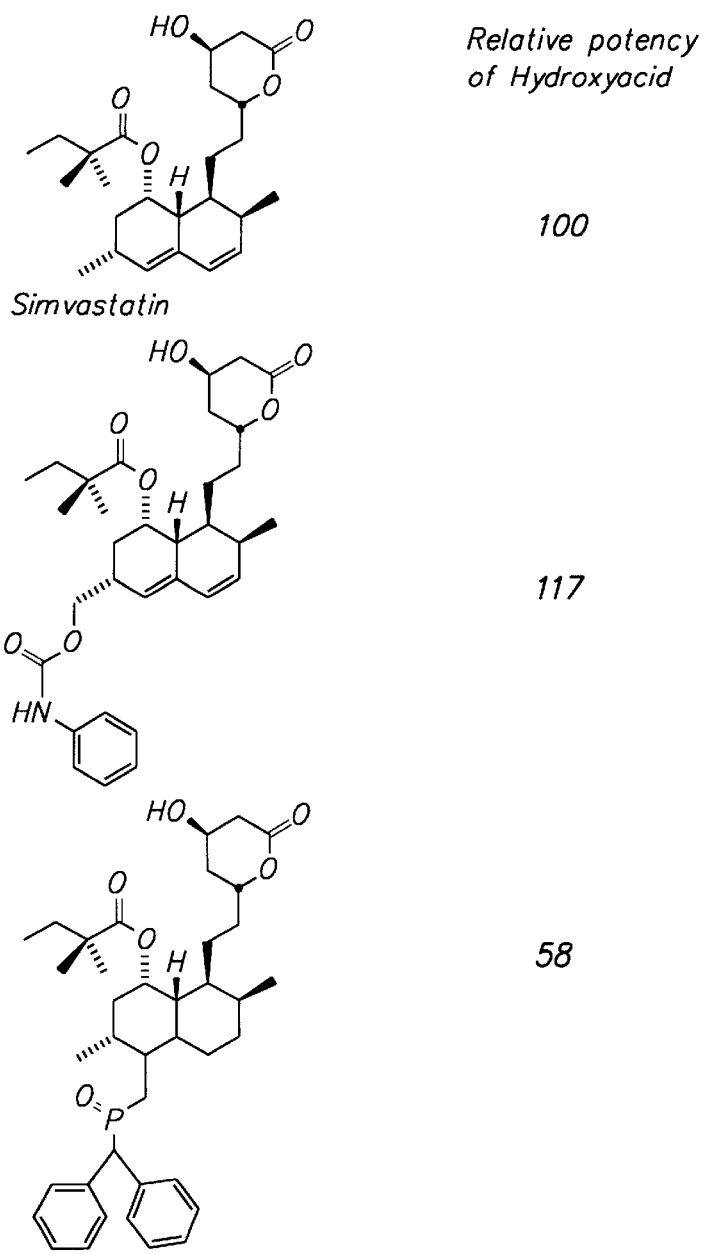
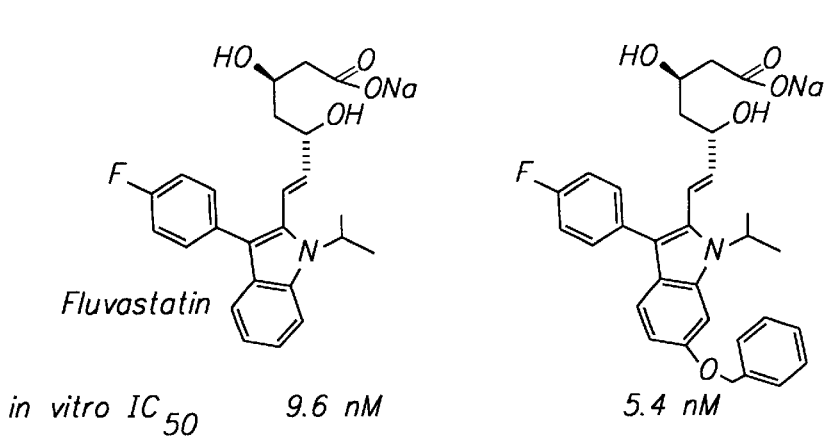
FIG. 8
FIG. 9

MULTIBINDING INHIBITORS OF HMG-COA REDUCTASE

CROSS-REFERENCE TO RELATED APPLICATIONS

This application claims the benefit of U.S. patent application Ser. No. 60/088,448, filed Jun. 8, 1998; U.S. patent application Ser. No. 60/093,072, filed Jul. 16, 1998; and U.S. patent application Ser. No. 60/114,083, filed Dec. 28, 1998; the disclosures of which are incorporated herein by reference in their entirety.

BACKGROUND OF THE INVENTION

1. Field of the Invention

This invention relates to novel multibinding compounds (agents) that inhibit 3-hydroxy-3-methylglutaryl coenzyme A (HMG-CoA) reductase, the rate limiting enzyme in cholesterol biosynthesis, and to pharmaceutical compositions comprising such compounds. Accordingly, the multibinding compounds and pharmaceutical compositions of this invention are useful in the treatment and prevention of hypercholesterolemia, hyperlipidemia, atherosclerosis and the like.

2. References

The following publications are cited in this application as superscript numbers:

[1] A. Endo et al., *FEBS Letters* 1976, 72, 323–326.
[2] P. Louis-Flamberg et al., *Biochemistry* 1990, 29, 4115–4120.
[3] H. Pang et al., *Pharmacotherapy* 1997, 17, 1157–1177.
[4] H. Bischoff et al., *Atherosclerosis* 1997, 135, 119–130.
[5] C. B. Blum, *J. Cardiol* 1994, 73, 3D–11D.
[6] J. D. Bergstrom et al., *Biochim. Biophys. Acta* 1998, 1389, 213–221.
[7] C. E. Nakamura et al., *Biochemistry* 1985, 24, 1364–1376.
[8] U.S. Pat. No. 4,963,538, issued Oct. 16, 1990 to Duggan et al.
[9] EP Publication No. 0 251 625 B1, published May 29, 1991.
[10] U.S. Pat. No. 4,739,073, issued Apr. 19, 1988 to Kathawala.
[11] B. D. Roth et al., *J. Med. Chem.* 1990, 34, 357–366.
[12] C. Chan et al., *J. Med. Chem.* 1993, 36, 3646–3657.
[13] G. Beck et al., *J. Med. Chem.* 1990, 33, 52–60.
[14] J. Robl et al., *J. Med. Chem.* 1991, 34, 2804–2815.
[15] C. M. Lawrence et al., *Science* 1995, 268, 1758–1762.

All of the above publications are herein incorporated by reference in their entirety to the same extent as if each individual publication was specifically and individually indicated to be incorporated by reference in its entirety.

3. State of the Art

Over the past 15 years, a number of new drugs collectively known as statins or vastatins have been introduced to reduce serum LDL cholesterol levels (representative examples of these drugs are shown in FIG. 1). High LDL cholesterol levels have been shown to be an important risk factor in the development of arteriosclerosis and ischaernic heart disease. The statins have been found to lower serum LDL cholesterol levels in a dose dependent manner. Additionally, these drugs lower serum triglyceride levels; another risk factor for heart disease.

The statins lower serum LDL cholesterol levels by competitive inhibition of 3-hydroxyl-3-methylglutaryl-Coenzyme A reductase (HMG-COA reductase), an enzyme involved in the biosynthesis of cholesterol.[1-4] The two-step reduction of HMG-CoA is illustrated in FIG. 2. The statins, such as simvastatin, appear to be mimics or analogs of intermediate C shown in FIG. 2. By binding tightly to the active site of the enzyme, the statins block the reduction of HMG-CoA, a step necessary in the biosynthesis of cholesterol. This inhibition of cholesterol biosynthesis by the statins results in a decrease in the production and secretion of LDL cholesterol. In addition, the upregulation of LDL receptors, especially in the liver, leads to the removal of LDLs from the serum. Thus, by reducing the production of LDL cholesterol and by causing LDL cholesterol to be removed from the serum, the statins effectively reduce overall serum LDL cholesterol levels.

Two-thirds of the total cholesterol found in the body is of endogenous origin. The major site of cholesterol biosynthesis is in the liver. Such liver-derived cholesterol is the main cause of the development of hyper-cholesterolaemia. In contrast, cholesterol production in non-hepatic cells is needed for normal cell function. Therefore, selective inhibition of HMG-CoA reductase in the liver is an important requirement for HMG-COA reductase inhibitors. In this regard, the statins typically have high oral availability and high hepatic extraction during their first pass through the liver.[5]

Even though the current HMG-CoA reductase inhibitors are quite potent, (i.e., having $IC_{50}$'s in the range of about 1 nanomolar), a need exists for even more potent and longer lasting HMG-CoA reductase inhibitors. Tighter binding inhibitors would decrease the amount of drug that escapes from the liver and this, in turn, would decrease adverse side effects. Additionally, a longer plasma half-life appears to be associated with maximum cholesterol lowering.[6] Thus, increasing the duration of effect of the inhibitor is expected to result in even lower serum cholesterol levels.

It has now been discovered that HMG-CoA reductase inhibitors having surprising and unexpected properties can be prepared by linking from 2 to 10 ligands capable of binding to HMG-CoA reductase to one or more linkers. Such multibinding compounds provide greater biological and/or therapeutic effects than the aggregate of the unlinked ligands due to their multibinding properties.

SUMMARY OF THE INVENTION

This invention is directed to novel multibinding compounds (agents) that inhibit 3-hydroxy-3-methylglutaryl coenzyme A (HMG-CoA) reductase. The multibinding compounds of this invention are useful in the treatment and prevention of hypercholesterolemia, hyperlipidemia, atherosclerosis and the like.

Accordingly, in one of its composition aspects, this invention provides a multibinding compound comprising from 2 to 10 ligands covalently attached to one or more linkers, wherein each of said ligands independently comprises a moiety capable of binding to 3-hydroxy-3-methylglutaryl coenzyme A reductase and further wherein the distance between ligands is at least 10 Å; and pharmaceutically acceptable salts thereof.

In another of its composition aspects, this invention provides a multibinding compound of formula I:

$$(L)_p(X)_q \qquad \text{I}$$

wherein each L is independently a ligand comprising a moiety capable of binding to 3-hydroxy-3-methylglutaryl coenzyme A reductase; each X is independently a linker; p is an integer of from 2 to 10; and q is an integer of from 1 to 20; and further wherein the distance between ligands is at least 10 Å; and pharmaceutically acceptable salts thereof.

Preferably, q is less than p in the multibinding compounds of this invention.

Preferably, each ligand, L, in the multibinding compound of formula I is independently selected from the group consisting of:

(a) a compound of formula IA:

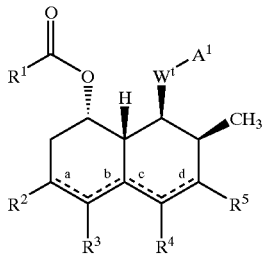

IA wherein
A$^1$ is selected from the group consisting of:

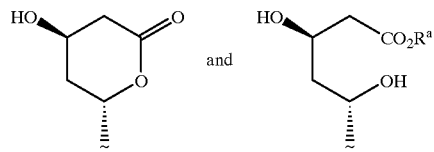

and where IV is selected from the group consisting of hydrogen, lower alkyl and a pharmaceutically-acceptable cation;

R$^1$ is selected from the group consisting of alkyl, substituted alkyl, alkenyl, substituted alkenyl, alkynyl, substituted alkynyl, cycloalkyl, substituted cycloalkyl, alkoxy, substituted alkoxy, aryl, heterocyclic, amino, substituted amino, thioalkoxy, substituted thioalkoxy and thioaryloxy;

R$^2$ is selected from the group consisting of hydrogen, alkyl, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or R$^2$ together with the carbon atom to which it is attached represents a spiro-attached cycloalkyl group;

R$^3$ is selected from the group consisting of hydrogen, alkyl, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or R$^3$ together with the carbon atom to which it is attached represents a spiro-attached cycloalkyl group;

R$^4$ is selected from the group consisting of hydrogen, alkyl, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or R$^4$ together with the carbon atom to which it is attached represents a spiro-attached cycloalkyl group;

R$^5$ is selected from the group consisting of hydrogen, alkyl, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or R$^2$ together with the carbon atom to which it is attached represents a spiro-attached cycloalkyl group; and a, b, c and d represent optional double bonds, provided that when a or c is a double bond, b is not a double bond; and when b or d is a double bond, c is not a double bond; and W$^1$ is —CH$_2$CH$_2$—;

provided that one of R$^2$, R$^3$, R$^4$ or R$^5$ is a covalent bond linking the ligand to a linker;

(b) a compound of formula IB:

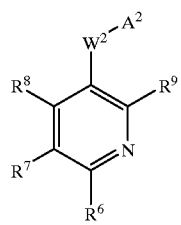

IB wherein
A$^2$ is selected from the group consisting of:

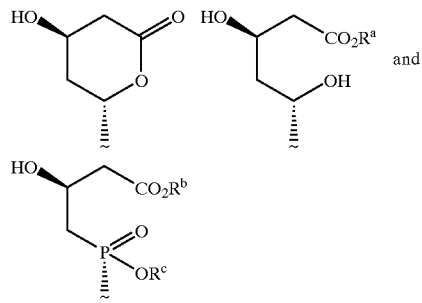

and where R$^a$, R$^b$ and R$^c$ are independently selected from the group consisting of hydrogen, lower alkyl and a pharmaceutically-acceptable cation;

R$^6$ is selected from the group consisting of hydrogen, alkyl, substituted alkyl, alkenyl, substituted alkenyl, alkoxy, substituted alkoxy, cycloalkyl, substituted cycloalkyl, cycloalkenyl, substituted cycloalkenyl, aryl, substituted amino, heterocyclic, heteroaryl and a covalent bond attaching the ligand to a linker;

R$^7$ is selected from the group consisting of hydrogen, alkyl, substituted alkyl, alkenyl, substituted alkenyl, alkoxy, substituted alkoxy, cycloalkyl, substituted cycloalkyl, cycloalkenyl, substituted cycloalkenyl, aryl, substituted amino, heterocyclic, heteroaryl, alkoxycarbonyl, cyano, carboxyl and a covalent bond attaching the ligand to a linker;

R$^8$ and R$^9$ are independently selected from the group consisting of hydrogen, alkyl, alkenyl, cycloalkyl, cycloalkenyl, aryl, aralkyl and aralkoxy;

W$^2$ is —CH$_2$CH$_2$—, —CH=CH— or —C≡—;

provided that one of R$^6$ or R$^7$ is a covalent bond linking the ligand to a linker;

(c) a compound of formula IC:

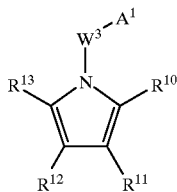

IC wherein
$A^1$ is as defined above;
$R^{10}$ is selected from the group consisting of cycloalkyl and aryl;
one of $R^{11}$ and $R^{12}$ is —C(O)NR$^{14}$R$^{15}$ where $R^{14}$ and $R^{15}$ are independently selected from the group consisting of hydrogen, alkyl, aryl and a covalent bond attaching the ligand to a linker; and the other of $R^{11}$ and $R^{12}$ is selected from the group consisting of hydrogen, alkyl, cycloalkyl and a covalent bond attaching the ligand to a linker;
$R^{13}$ is selected from the group consisting of alkyl, cycloalkyl and trifluoromethyl;
$W^3$ is —CH$_2$—, —CH$_2$CH$_2$—, —CH$_2$CH$_2$CH$_2$— or —CH$_2$CH(CH$_3$)—;
provided that one of $R^{11}$, $R^{12}$, $R^{14}$ or $R^{15}$ is a covalent bond linking the ligand to a linker; and (d) a compound of formula ID:

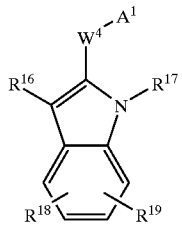

ID wherein
$A^1$ is as defined above;
one of $R^{16}$ and $R^{17}$ is aryl; and the other of $R^{16}$ and $R^{17}$ is selected from the group consisting of alkyl, cycloalkyl and aralkyl;
$R^{18}$ and $R^{19}$ are independently selected from the group consisting of hydrogen, alkyl, cycloalkyl, alkoxy, halo, aryloxy, aralkoxy and a covalent bond attaching the ligand to a linker; and
$W^4$ is —CH$_2$—, —CH$_2$CH$_2$—, —CH$_2$CH$_2$CH$_2$— or —CH=CH—;
provided that one of $R^{18}$ or $R^{19}$ is a covalent bond linking the ligand to a linker;
and pharmaceutically-acceptable salts thereof.

In still another of its composition aspects, this invention provides a multibinding compound of formula II:

L'—X'—L'    II wherein each L' is independently a ligand comprising a moiety capable of binding to 3-hydroxy-3-methylglutaryl coenzyme A reductase; and X' is a linker;
and further wherein the distance between the ligands is at least 10 Å; and pharmaceutically-acceptable salts thereof.

Preferably, each ligand, L', in the multibinding compound of formula II is independently selected from the group consisting of:

(a) a compound of formula IIA:

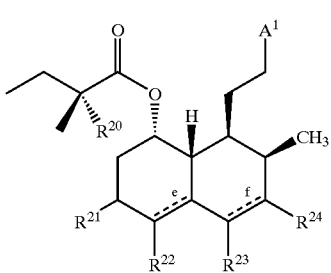

IIA wherein
$A^1$ is selected from the group consisting of:

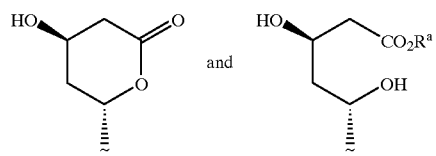

and where $R^a$ is selected from the group consisting of hydrogen, lower alkyl and a pharmaceutically-acceptable cation;
$R^{21}$ is selected from the group consisting of hydrogen, lower alkyl, hydroxy and a covalent bond attaching the ligand to a linker;
$R^{22}$, $R^{23}$ and $R^{24}$ are independently selected from the group consisting of hydrogen and a covalent bond attaching the ligand to a linker; and
e and f represent optional double bonds;
provided that one of $R^{21}$, $R^{22}$, $R^{23}$ or $R^{24}$ is a covalent bond linking the ligand to a linker;

(b) a compound of formula IIB:

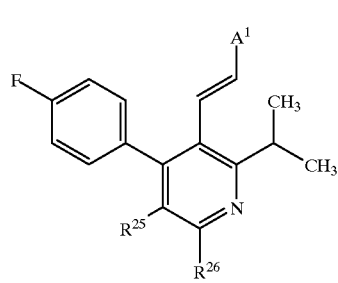

IIB wherein
$A^1$ is as define above;
$R^{25}$ is selected from the group consisting of hydrogen, alkyl, alkoxyalkyl and a covalent bond attaching the ligand to a linker; and
$R^{26}$ is selected from the group consisting of hydrogen, alkyl, cycloalkyl and a covalent bond attaching the ligand to a linker;
provided that one of $R^{25}$ or $R^{26}$ is a covalent bond linking the ligand to a linker;

(c) a compound of formula IIC:

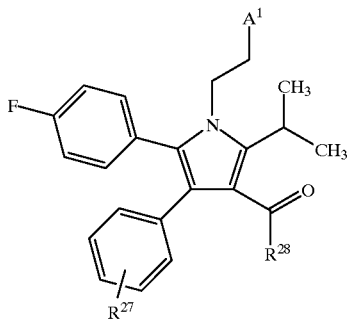

IIC wherein
$A^1$ is as defined above;
$R^{27}$ is selected from the group consisting of hydrogen and a covalent bond attaching the ligand to a linker; and
$R^{28}$ is selected from the group consisting of amino, substituted amino and a covalent bond attaching the ligand to a linker;
provided that one of $R^{27}$ or $R^{28}$ is a covalent bond linking the ligand to a linker; and (d) a compound of formula IID:

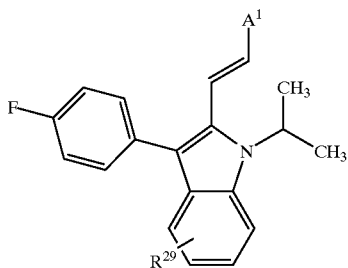

IID wherein
$A^1$ is as defined above; and
$R^{29}$ is a covalent bond attaching the ligand to a linker;
and pharmaceutically-acceptable salts thereof.

In a preferred embodiment, this invention is also directed to a multibinding compound of formula III:

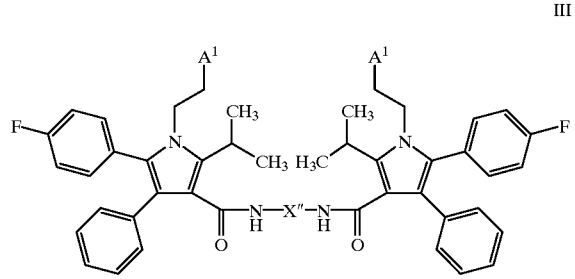

III wherein
each $A^1$ is independently selected from the group consisting of:

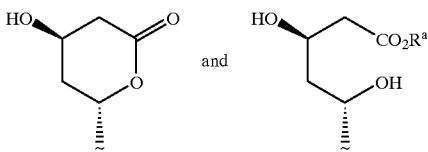

where $R^a$ is selected from the group consisting of hydrogen, lower alkyl and a pharmaceutically-acceptable cation; and X" is a linker; and further wherein the distance between ligands is at least 10 Å; and pharmaceutically-acceptable salts thereof.

In another preferred embodiment, this invention is directed to a multibinding compound of formula IV:

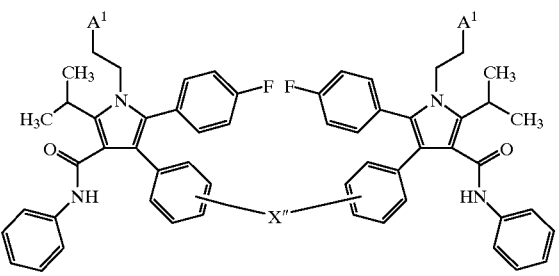

IV wherein
each $A^1$ is independently selected from the group consisting of:

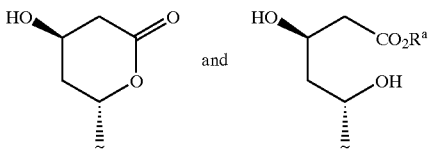

where $R^a$ is selected from the group consisting of hydrogen, lower alkyl and a pharmaceutically-acceptable cation; and X" is a linker; and further wherein the distance between ligands is at least 10 Å; and pharmaceutically-acceptable salts thereof.

Preferably, in the above embodiments, each linker (i.e., X, X' or X") independently has the formula:

$$-X^a-Z-(Y^a-Z)_m-Y^b-Z-X^a-$$

wherein
m is an integer of from 0 to 20;
$X^a$ at each separate occurrence is selected from the group consisting of —O—, —S—, —NR—, —C(O)—, —C(O)O—, —C(O)NR—, —C(S), —C(S)O—, —C(S)NR— or a covalent bond where R is as defined below;
Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;
$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —N=C(X$^a$)—NR'—, —P(O)(OR')—O—, —S(O)$_n$CR'R''—, —S(O)$_n$—NR'—, —S—S— and a covalent bond; where n is 0, 1 or 2; and R, R' and R'' at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

In yet another of its composition aspects, this invention provides a pharmaceutical composition comprising a pharmaceutically acceptable carrier and an effective amount of a multibinding compound comprising from 2 to 10 ligands covalently attached to one or more linkers, wherein each of said ligands independently comprises a moiety capable of binding to 3-hydroxy-3-methylglutaryl coenzyme A reductase and further wherein the distance between ligands is at least 10 Å; and pharmaceutically acceptable salts thereof.

This invention is also directed to pharmaceutical compositions comprising a pharmaceutically acceptable carrier and an effective amount of a multibinding compound of formula I, II, III or IV.

The multibinding compounds of this invention are effective inhibitors of the enzyme 3-hydroxyl-3-methylglutaryl-Coenzyme A reductase (HMG-COA reductase), an enzyme involved in the biosynthesis of cholesterol. Accordingly, in one of its method aspects, this invention provides a method for reducing cholesterol biosynthesis in a mammal comprising administering to said mammal an effective amount of a pharmaceutical composition comprising a pharmaceutically acceptable carrier and a multibinding compound comprising from 2 to 10 ligands covalently attached to one or more linkers, wherein each of said ligands independently comprises a moiety capable of binding to 3-hydroxy-3-methylglutaryl coenzyme A reductase and further wherein the distance between ligands is at least 10 Å; and pharmaceutically acceptable salts thereof.

This invention is also directed to general synthetic methods for generating large libraries of diverse multimeric compounds which multimeric compounds are candidates for possessing multibinding properties for 3-hydroxy-3-methylglutaryl coenzyme A reductase. The diverse multimeric compound libraries provided by this invention are synthesized by combining a library of linkers with a library of ligands each having complementary functional groups permitting covalent linkage. The library of linkers is preferably selected to have diverse properties such as valency, linker length, linker geometry and rigidity, hydrophilicity or hydrophobicity, amphiphilicity, acidity, basicity, polarizability and polarization. The library of ligands is preferably selected to have diverse attachment points on the same ligand, different functional groups at the same site of otherwise the same ligand, and the like.

Additionally, this invention is directed to libraries of diverse multimeric compounds which multimeric compounds are candidates for possessing multibinding properties for 3-hydroxy-3-methylglutaryl coenzyme A reductase. These libraries are prepared via the methods described above and permit the rapid and efficient evaluation of what molecular constraints impart multibinding properties to a ligand or a class of ligands for 3-hydroxy-3-methylglutaryl coenzyme A reductase.

Accordingly, in one of its method aspects, this invention is directed to a method for identifying multimeric ligand compounds possessing multibinding properties for 3-hydroxy-3-methylglutaryl coenzyme A reductase, which method comprises:

(a) identifying a ligand or a mixture of ligands wherein each ligand contains at least one reactive functionality;

(b) identifying a library of linkers wherein each linker in said library comprises at least two functional groups having complementary reactivity to at'least one of the reactive functional groups of the ligand;

(c) preparing a multimeric ligand compound library by combining at least two stoichiometric equivalents of the ligand or mixture of ligands identified in (a) with the library of linkers identified in (b) under conditions wherein the complementary functional groups react to form a covalent linkage between said linker and at least two of said ligands; and (d) assaying the multimeric ligand compounds produced in the library prepared in (c) above to identify multimeric ligand compounds possessing multibinding properties for 3-hydroxy-3-methylglutaryl coenzyme A reductase.

In another of its method aspects, this invention is directed to a method for identifying multimeric ligand compounds possessing multibinding properties for 3-hydroxy-3-methylglutaryl coenzyme A reductase, which method comprises:

(a) identifying a library of ligands wherein each ligand contains at least one reactive functionality;

(b) identifying a linker or mixture of linkers wherein each linker comprises at least two functional groups having complementary reactivity to at least one of the reactive functional groups of the ligand;

(c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands; and (d) assaying the multimeric ligand compounds produced in the library prepared in (c) above to identify multimeric ligand compounds possessing multibinding properties for 3-hydroxy-3-methylglutaryl coenzyme A reductase.

Preferably, in these methods, the preparation of the multimeric ligand compound library is achieved by either the sequential or concurrent combination of the two or more stoichiometric equivalents of the ligands identified in (a) with the linkers identified in (b).

Additionally, the multimeric ligand compounds comprising the multimeric ligand compound library are preferably dimeric. In one embodiment, the dimeric ligand compounds comprising the dimeric ligand compound library are heterodimeric. The heterodimeric ligand compound library is preferably prepared by sequential addition of a first and second ligand.

In a preferred embodiment of the above methods, prior to procedure (d), each member of the multimeric ligand compound library is isolated from the library. More preferably, each member of the library is isolated by preparative liquid chromatography mass spectrometry (LCMS).

In the above methods, the linker or linkers employed are preferably selected from the group comprising flexible linkers, rigid linkers, hydrophobic linkers, hydrophilic linkers, linkers of different geometry, acidic linkers, basic linkers, linkers of different polarization and/or polarizability and amphiphilic linkers. More preferably, the linkers comprise linkers of different chain length and/or having different complementary reactive groups. Still more preferably, the linkers are selected to have different linker lengths ranging from about 10 to 100 Å.

The ligand or mixture of ligands employed in the above methods is preferably selected to have reactive functionality at different sites on said ligands. More preferably, the reactive functionality is selected from the group consisting of carboxylic acids, carboxylic acid halides, carboxyl esters, amines, halides, pseudohalides, isocyanates, vinyl unsaturation, ketones, aldehydes, thiols, alcohols, anhydrides, boronates, and precursors thereof wherein the reactive functionality on the ligand is selected to be complementary to at least one of the reactive groups on the linker so that a covalent linkage can be formed between the linker and the ligand.

In one preferred embodiment of the above methods, the multimeric ligand compound library comprises homomeric ligand compounds. In another preferred embodiment, the multimeric ligand compound library comprises heteromeric ligand compounds.

In one of its composition aspects, this invention is directed to a library of multimeric ligand compounds which may possess multivalent properties for 3-hydroxy-3-methylglutaryl coenzyme A reductase, which library is prepared by the method comprising:
  (a) identifying a ligand or a mixture of ligands wherein each ligand contains at least one reactive functionality;
  (b) identifying a library of linkers wherein each linker in said library comprises at least two functional groups having complementary reactivity to at least one of the reactive functional groups of the ligand; and
  (c) preparing a multimeric ligand compound library by combining at least two stoichiometric equivalents of the ligand or mixture of ligands identified in (a) with the library of linkers identified in (b) under conditions wherein the complementary functional groups react to form a covalent linkage between said linker and at least two of said ligands.

In another of its composition aspects, this invention is directed to a library of multimeric ligand compounds which may possess multivalent properties for 3-hydroxy-3-methylglutaryl coenzyme A reductase, which library is prepared by the method comprising:
  (a) identifying a library of ligands wherein each ligand contains at least one reactive functionality;
  (b) identifying a linker or mixture of linkers wherein each linker comprises at least two functional groups having complementary reactivity to at least one of the reactive functional groups of the ligand; and
  (c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands.

In a preferred embodiment, the linker or linkers employed are preferably selected from the group comprising flexible linkers, rigid linkers, hydrophobic linkers, hydrophilic linkers, linkers of different geometry, acidic linkers, basic linkers, linkers of different polarization and/or polarizability and amphiphilic linkers. More preferably, the linkers comprise linkers of different chain length and/or having different complementary reactive groups. Still more preferably, the linkers are selected to have different linker lengths ranging from about 10 to 100 Å.

In the above libraries, the ligand or mixture of ligands is preferably selected to have reactive functionality at different sites on said ligands. Preferably, the reactive functionality is selected from the group consisting of carboxylic acids, carboxylic acid halides, carboxyl esters, amines, halides, pseudohalides, isocyanates, vinyl unsaturation, ketones, aldehydes, thiols, alcohols, anhydrides, boronates, and precursors thereof wherein the reactive functionality on the ligand is selected to be complementary to at least one of the reactive groups on the linker so that a covalent linkage can be formed between the linker and the ligand.

In one embodiment, the multimeric ligand compound library comprises homomeric ligand compounds (i.e., each of the ligands is the same, although it may be attached at different points). In another embodiment, the multimeric ligand compound library comprises heteromeric ligand compounds (i.e., at least one of the ligands is different from the other ligands).

In another of its method aspects, this invention is directed to an iterative method for identifying multimeric ligand compounds possessing multibinding properties for 3-hydroxy-3-methylglutaryl coenzyme A reductase, which method comprises:
  (a) preparing a first collection or iteration of multimeric compounds which is prepared by contacting at least two stoichiometric equivalents of the ligand or mixture of ligands which target a receptor with a linker or mixture of linkers wherein said ligand or mixture of ligands comprises at least one reactive functionality and said linker or mixture of linkers comprises at least two functional groups having complementary reactivity to at least one of the reactive functional groups of the ligand wherein said contacting is conducted under conditions wherein the complementary functional groups react to form a covalent linkage between said linker and at least two of said ligands;
  (b) assaying said first collection or iteration of multimeric compounds to assess which if any of said multimeric compounds possess multibinding properties for 3-hydroxy-3-methylglutaryl coenzyme A reductase;
  (c) repeating the process of (a) and (b) above until at least one multimeric compound is found to possess multibinding properties for 3-hydroxy-3-methylglutaryl coenzyme A reductase;
  (d) evaluating what molecular constraints imparted or are consistent with imparting multibinding properties to the multimeric compound or compounds found in the first iteration recited in (a)–(c) above;
  (e) creating a second collection or iteration of multimeric compounds which elaborates upon the particular molecular constraints imparting multibinding properties to the multimeric compound or compounds found in said first iteration;
  (f) evaluating what molecular constraints imparted or are consistent with imparting enhanced multibinding properties to the multimeric compound or compounds found in the second collection or iteration recited in (e) above;
  (g) optionally repeating steps (e) and (f) to further elaborate upon said molecular constraints.

Preferably, steps (e) and (f) are repeated from 2–50 times. More preferably, steps (e) and (f) are repeated from 5–50 times.

Preferably, the ligands employed in the above methods and library compositions are selected from ligands of formula IA–ID, more preferably, from ligands of formula IIA–IID.

BRIEF DESCRIPTION OF THE DRAWINGS

FIG. 8 shows various simvastatin analogs having bulky substitutents in the "southern" binding domain and their in vitro activity.

FIG. 9 shows a fluvastatin analog having a bulky substitutent in the "southern" binding domain and its in vitro activity.

DETAILED DESCRIPTION OF THE INVENTION

Figure 1:
FIG. 1 shows the chemical structures for representative statins or vastatins, each of which is an inhibitor of the enzyme HMG-COA reductase.
Figure 1:
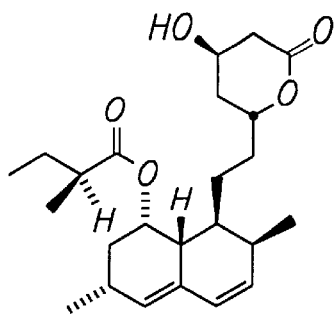
Figure 1:
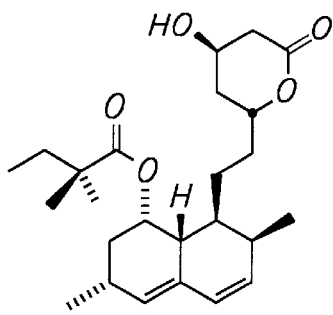
Figure 1:
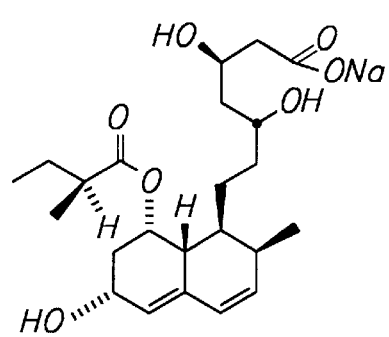
Figure 1:
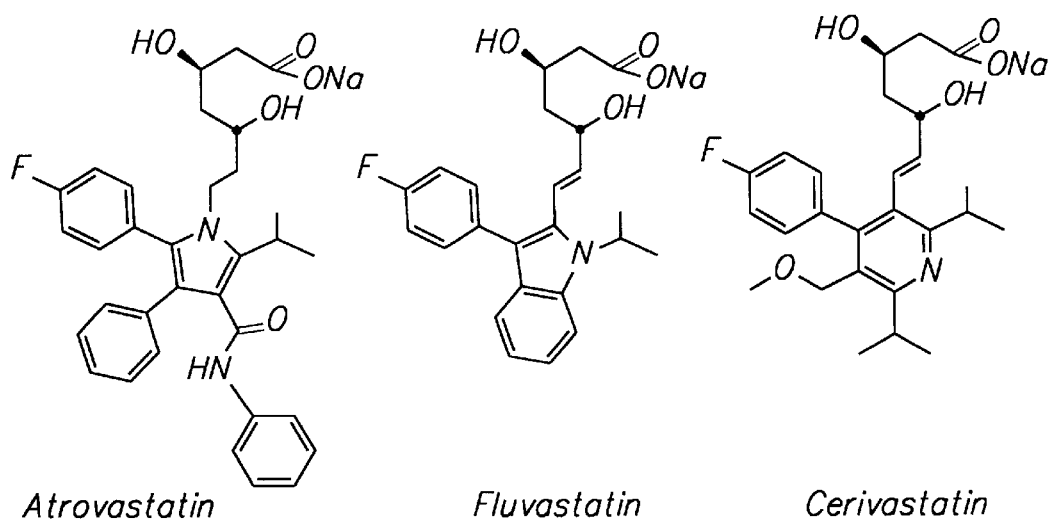
Figure 2:
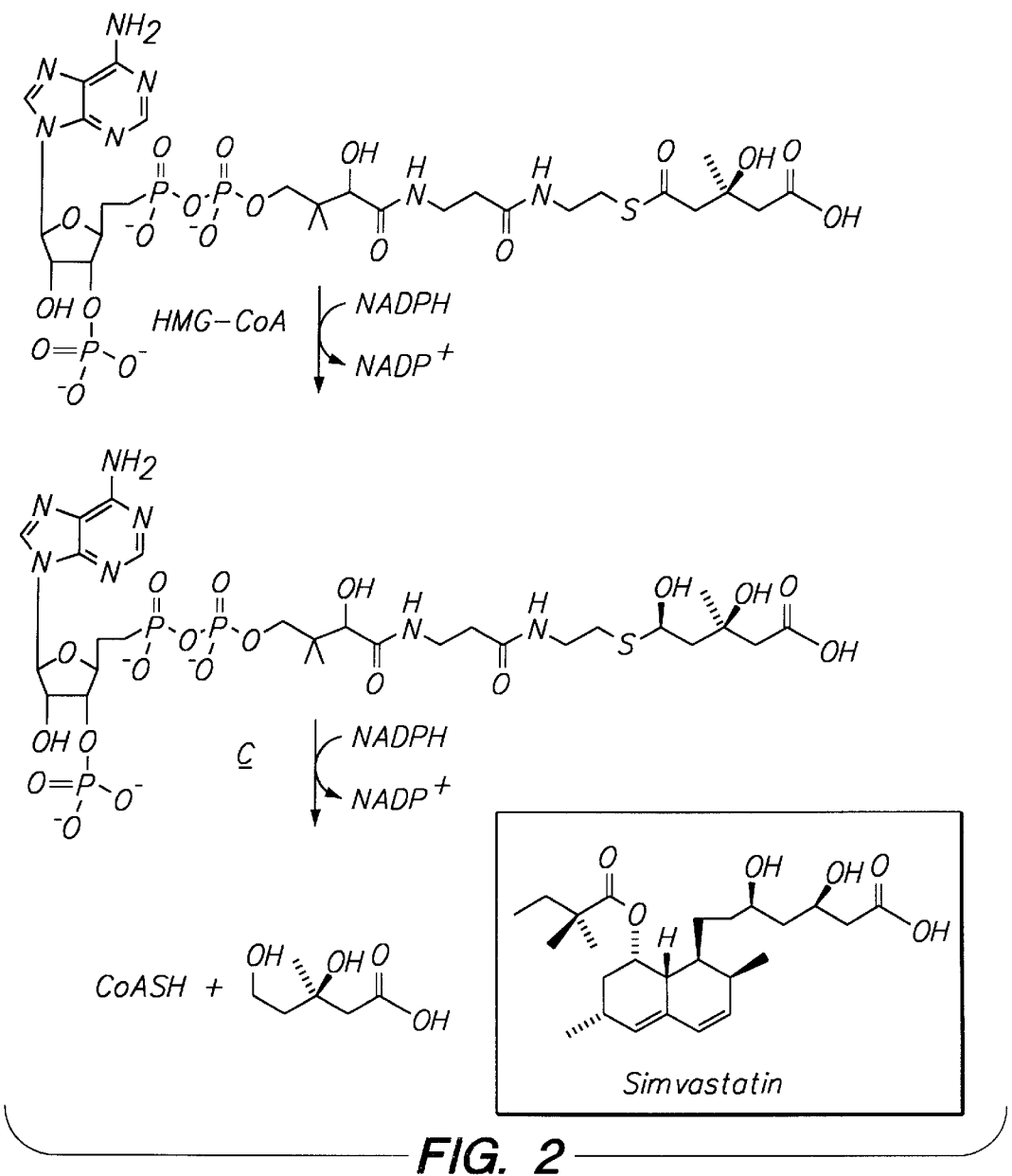
FIG. 2 illustrates the reduction of HMG-CoA with NADPH and shows the structural similarity between intermediate C and a representative statin, i.e., simvastatin.

This invention is directed to multibinding compounds which inhibit the enzyme HMG-CoA reductase, pharmaceutical compositions containing such compounds and methods for reducing cholesterol biosynthesis in mammals. When discussing such compounds, compositions or methods, the following terms have the following meanings unless otherwise indicated. Any undefined terms have their art recognized meanings.

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above, having from 1 to 5 substitutents, and preferably 1 to 3 substitutents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkylene" refers to a diradical of a branched or unbranched saturated hydrocarbon chain, preferably having from 1 to 40 carbon atoms, more preferably 1 to 10 carbon atoms and even more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures.

The term "alkaryl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. This term is exemplified by groups such as ethenylene (—CH=CH—), the propenylene isomers (e.g., —CH$_2$CH=CH— and —C(CH$_3$)=CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1–6 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of an unsaturated hydrocarbon preferably having from 2 to 40 carbon atoms, more preferably 2 to 10 carbon atoms and even more preferably 2 to 6 carbon atoms and having at least 1 and preferably from 1–6 sites of acetylene (triple bond) unsaturation. Preferred alkynylene groups include ethenylene (—C≡C—), propargylene (—CH$_2$C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, amninoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, -SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "heterocycle" or "heterocyclic" refers to a monoradical saturated unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "heterocyclooxy" refers to the group heterocyclic-O—.

The term "thioheterocyclooxy" refers to the group heterocyclic-S—.

The term "heterocyclene" refers to the diradical group formed from a heterocycle, as defined herein, and is exemplified by the groups 2,6-morpholino, 2,5-morpholino and the like.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "spiro-attached cycloalkyl group" refers to a cycloalkyl group attached to another ring via one carbon atom common to both rings.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "pharmaceutically-acceptable salt" refers to salts which retain the biological effectiveness and properties of the multibinding compounds of this invention and which are not biologically or otherwise undesirable. In many cases, the multibinding compounds of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri (cycloalkyl) amines, substituted cycloalkyl amines, disubstituted cycloalkyl amine, trisubstituted cycloalkyl amines, cycloalkenyl amines, di(cycloalkenyl) amines, tri (cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri (iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically-acceptable cation" refers to the cation of a pharmaceutically-acceptable salt.

The term "protecting group" or "blocking group" refers to any group which when bound to one or more hydroxyl, thiol, amino or carboxyl groups of the compounds (including intermediates thereof) prevents reactions from occurring at these groups and which protecting group can be removed by conventional chemical or enzymatic steps to reestablish the hydroxyl, thiol, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product.

Preferred removable thiol blocking groups include disulfide groups, acyl groups, benzyl groups, and the like.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC), and the like which can be removed by conventional conditions compatible with the nature of the product.

Preferred carboxyl protecting groups include esters such as methyl, ethyl, propyl, t-butyl etc. which can be removed by mild conditions compatible with the nature of the product.

The term "optional" or "optionally" means that the subsequently described event, circumstance or substituent may or may not occur, and that the description includes instances where said event or circumstance occurs and instances where it does not.

The term "ligand" as used herein denotes a compound or moiety that is capable of binding to the enzyme HMG CoA reductase. The specific region or regions of the ligand that is (are) recognized by the enzyme is designated as the "ligand domain". A ligand may be either capable of binding to an enzyme by itself, or may require the presence of one or more non-ligand components for binding (e.g., $Ca^{+2}$, $Mg^{+2}$ or a water molecule is required for the binding of a ligand to various ligand binding sites). Preferably, the ligand is an inhibitor of the enzyme HMG CoA reductase Examples of ligands useful in this invention are described herein. Those skilled in the art will appreciate that portions of the ligand structure that are not essential for specific molecular recognition and binding activity may be varied substantially, replaced or substituted with unrelated structures (for example, with ancillary groups as defined below) and, in some cases, omitted entirely without affecting the binding interaction. The primary requirement for a ligand is that it has a ligand domain as defined above. It is understood that the term ligand is not intended to be limited to compounds known to be useful in binding to HMG CoA reductase (e.g., known drugs). Those skilled in the art will understand that the term ligand can equally apply to a molecule that is not normally associated with enzyme binding properties. In addition, it should be noted that ligands that exhibit marginal activity or lack useful activity as monomers can be highly active as multivalent compounds because of the benefits conferred by multivalency.

The term "multibinding compound or agent" refers to a compound that is capable of multivalency, as defined below, and which has 2–10 ligands covalently bound to one or more linkers which may be the same or different. Multibinding compounds provide a biological and/or therapeutic effect greater than the aggregate of unlinked ligands equivalent thereto which are made available for binding. That is to say that the biological and/or therapeutic effect of the ligands attached to the multibinding compound is greater than that achieved by the same amount of unlinked ligands made available for binding to the ligand binding sites (receptors). The phrase "increased biological or therapeutic effect" includes, for example: increased affinity, increased selectivity for target, increased specificity for target, increased potency, increased efficacy, decreased toxicity, improved duration of activity or action, increased ability to kill cells such as fungal pathogens, cancer cells, etc., decreased side effects, increased therapeutic index, improved bioavailibity, improved pharmacokinetics, improved activity spectrum, and the like. The multibinding compounds of this invention will exhibit at least one and preferably more than one of the above-mentioned affects.

The term "multimeric compound" refers to a compound containing 2 to 10 ligands covalently connected through at least one linker which compound may or may not possess multibinding properties.

The term "potency" refers to the minimum concentration at which a ligand is able to achieve a desirable biological or therapeutic effect. The potency of a ligand is typically proportional to its affinity for its ligand binding site. In some cases, the potency may be non-linearly correlated with its affinity. In comparing the potency of two drugs, e.g., a multibinding agent and the aggregate of its unlinked ligand, the dose-response curve of each is determined under identical test conditions (e.g., in an in vitro or in vivo assay, in an appropriate animal model such a human patient). The finding that the multbinding agent produces an equivalent biological or therapeutic effect at a lower concentration than the aggregate unlinked ligand is indicative of enhanced potency.

The term "univalency" as used herein refers to a single binding interaction between one ligand as defined herein with one ligand binding site as defined herein. It should be noted that a compound having multiple copies of a ligand (or ligands) exhibit univalency when only one ligand is interacting with a ligand binding site. Examples of univalent interactions are depicted below.

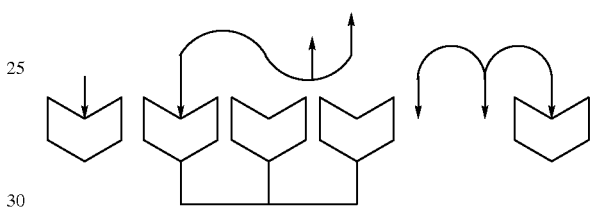

The term "multivalency" as used herein refers to the concurrent binding of from 2 to 10 linked ligands (which may be the same or different) and two or more corresponding receptors (ligand binding sites) on one or more enzymes which may be the same or different.

For example, two ligands connected through a linker that bind concurrently to two ligand binding sites would be considered as bivalency; three ligands thus connected would be an example of trivalency. An example of trivalent binding, illustrating a multibinding compound bearing three ligands versus a monovalent binding interaction, is shown below:

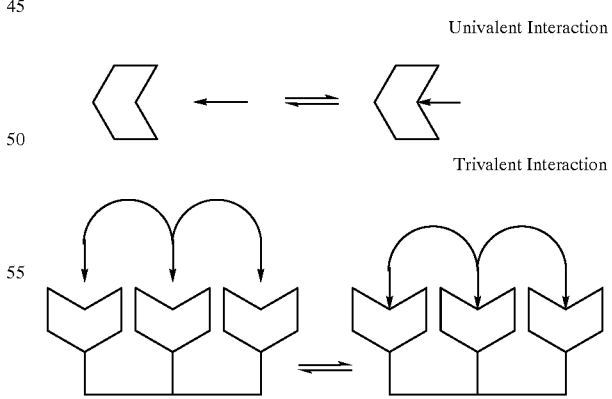

It should be understood that all compounds that contain multiple copies of a ligand attached to a linker or to linkers do not necessarily exhibit the phenomena of multivalency, i.e., that the biological and/or therapeutic effect of the multibinding agent is greater than the sum of the aggregate of unlinked ligands made available for binding to the ligand binding site (receptor). For multivalency to occur, the ligands that are connected by a linker or linkers have to be presented to their ligand binding sites by the linker(s) in a specific manner in order to bring about the desired ligand-orienting result, and thus produce a multibinding event.

The term "selectivity" or "specificity" is a measure of the binding preferences of a ligand for different ligand binding sites (receptors). The selectivity of a ligand with respect to its target ligand binding site relative to another ligand binding site is given by the ratio of the respective values of $K_d$ (i.e., the dissociation constants for each ligand-receptor complex) or, in cases where a biological effect is observed below the $K_d$, the ratio of the respective $EC_{50}$'s (i.e., the concentrations that produce 50% of the maximum response for the ligand interacting with the two distinct ligand binding sites (receptors)).

The term "ligand binding site" denotes the site on the HMG CoA reductase enzyme that recognizes a ligand domain and provides a binding partner for the ligand. The ligand binding site may be defined by monomeric or multimeric structures. This interaction may be capable of producing a unique biological effect, for example, agonism, antagonism, modulatory effects, may maintain an ongoing biological event, and the like.

It should be recognized that the ligand binding sites of the enzyme that participate in biological multivalent binding interactions are constrained to varying degrees by their intra- and inter-molecular associations (e.g., such macromolecular structures may be covalently joined to a single structure, noncovalently associated in a multimeric structure, embedded in a membrane or polymeric matrix, and so on) and therefore have less translational and rotational freedom than if the same structures were present as monomers in solution.

The terms "agonism" and "antagonism" are well known in the art. The term "modulatory effect" refers to the ability of the ligand to change the activity of an agonist or antagonist through binding to a ligand binding site.

The term "inert organic solvent" or "inert solvent" means a solvent which is inert under the conditions of the reaction being described in conjunction therewith including, by way of example only, benzene, toluene, acetonitrile, tetrahydrofuran, dimethylformamide, chloroform, methylene chloride, diethyl ether, ethyl acetate, acetone, methylethyl ketone, methanol, ethanol, propanol, isopropanol, t-butanol, dioxane, pyridine, and the like. Unless specified to the contrary, the solvents used in the reactions described herein are inert solvents.

The term "treatment" refers to any treatment of a pathologic condition in a mammal, particularly a human, and includes:

(i) preventing the pathologic condition from occurring in a subject which may be predisposed to the condition but has not yet been diagnosed with the condition and, accordingly, the treatment constitutes prophylactic treatment for the disease condition;

(ii) inhibiting the pathologic condition, i.e., arresting its development;

(iii) relieving the pathologic condition, i.e., causing regression of the pathologic condition; or (iv) relieving the conditions mediated by the pathologic condition.

The term "pathologic condition which is modulated by treatment with a ligand" covers all disease states (i.e., pathologic conditions) which are generally acknowledged in the art to be usefully treated with a ligand for the enzyme HMG CoA reductase in general, and those disease states which have been found to be usefully treated by a specific multibinding compound of our invention. Such disease states include, by way of example only, the treatment of a mammal afflicted with hypercholesterolemia, atherosclerosis and the like.

The term "therapeutically effective amount" refers to that amount of multibinding compound which is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "linker", identified where appropriate by the symbol X, X' or X", refers to a group or groups that covalently links from 2 to 10 ligands (as identified above) in a manner that provides for a compound capable of multivalency. Each linker may be chiral or achiral. Among other features, the linker is a ligand-orienting entity that permits attachment of multiple copies of a ligand (which may be the same or different) thereto. In some cases, the linker may itself be biologically active. The term "linker" does not, however, extend to cover solid inert supports such as beads, glass particles, fibers, and the like. But it is understood that the multibinding compounds of this invention can be attached to a solid support if desired. For example, such attachment to solid supports can be made for use in separation and purification processes and similar applications.

The extent to which multivalent binding is realized depends upon the efficiency with which the linker or linkers that joins the ligands presents these ligands to the array of available ligand binding sites. Beyond presenting these ligands for multivalent interactions with ligand binding sites, the linker or linkers spatially constrains these interactions to occur within dimensions defined by the linker or linkers. Thus, the structural features of the linker (valency, geometry, orientation, size, flexibility, chemical composition, etc.) are features of multibinding agents that play an important role in determining their activities.

The linkers used in this invention are selected to allow multivalent binding of ligands to the ligand binding sites of HMG CoA reductase, whether such sites are located interiorly, both interiorly and on the periphery of the enzyme structure, or at any intermediate position thereof. The distance between the nearest neighboring ligand domains is preferably greater than about 10 Å, more preferably in the range of about 50 Å to about 100 Å, still more preferably in the range of about 60 Å to about 100 Å.

The ligands are covalently attached to the linker or linkers using conventional chemical techniques providing for covalent linkage of the ligand to the linker or linkers. Reaction chemistries resulting in such linkages are well known in the art and involve the use of complementary functional groups on the linker and ligand. Preferably, the complementary functional groups on the linker are selected relative to the functional groups available on the ligand for bonding or which can be introduced onto the ligand for bonding. Again, such complementary functional groups are well known in the art. For example, reaction between a carboxylic acid of either the linker or the ligand and a primary or secondary amine of the ligand or the linker in the presence of suitable, well-known activating agents results in formation of an amide bond covalently linking the ligand to the linker; reaction between an amine group of either the linker or the ligand and a sulfonyl halide of the ligand or the linker results in formation of a sulfonamide bond covalently linking the ligand to the linker; and reaction between an alcohol or phenol group of either the linker or the ligand and an alkyl or aryl halide of the ligand or the linker results in formation of an ether bond covalently linking the ligand to the linker.

Table I below illustrates numerous complementary reactive groups and the resulting bonds formed by reaction there between.

TABLE I

Representative Complementary Binding Chemistries

| First Reactive Group | Second Reactive Group | Linkage |
|---|---|---|
| hydroxyl | isocyanate | urethane |
| amine | epoxide | β-hydroxyamine |
| sulfonyl halide | amine | sulfonamide |
| carboxyl | amine | amide |
| hydroxyl | alkyl/aryl halide | ether |

The linker is attached to the ligand at a position that retains ligand domain-ligand binding site interaction and specifically which permits the ligand domain of the ligand to orient itself to bind to the ligand binding site. Such positions and synthetic protocols for linkage are well known in the art. The term linker embraces everything that is not considered to be part of the ligand.

The relative orientation in which the ligand domains are displayed derives from the particular point or points of attachment of the ligands to the linker, and on the framework geometry. The determination of where acceptable substitutions can be made on a ligand is typically based on prior knowledge of structure-activity relationships (SAR) of the ligand and/or congeners and/or structural information about ligand-receptor complexes (e.g., X-ray crystallography, NMR, and the like). Such positions and the synthetic methods for covalent attachment are well known in the art. Following attachment to the selected linker (or attachment to a significant portion of the linker, for example 2–10 atoms of the linker), the univalent linker-ligand conjugate may be tested for retention of activity in the relevant assay.

Suitable linkers are discussed more fully below.

At present, it is preferred that the multibinding agent is a bivalent compound, e.g., two ligands which are covalently linked to linker X.

The term "library" refers to at least 3, preferably from $10^2$ to $10^9$ and more preferably from $10^2$ to $10^4$ multimeric compounds. Preferably, these compounds are prepared as a multiplicity of compounds in a single solution or reaction mixture which permits the facile synthesis thereof. In one embodiment, the library of multimeric compounds can be directly assayed for multibinding properties. In another embodiment, each member of the library of multimeric compounds is first isolated and, optionally, characterized. This member is then assayed for multibinding properties.

The term "collection" refers to a set of multimeric compounds which are prepared either sequentially or concurrently (e.g., combinatorially). The collection comprises at least 2 members; preferably from 2 to $10^4$ members and still more preferably from 10 to $10^4$ members.

The term "pseudohalide" refers to a functional group which react in a displacement reaction in a manner similar to a halogen, e.g., functions as a leaving group is a displacement reaction. Such functional groups include, by way of example, mesyl, tosyl, azido, cyano and the like.

Methodology

The linker, when covalently attached to multiple copies of the ligands, provides a biocompatible, substantially non-immunogenic multibinding compound. The biological activity of the multibinding compound is highly sensitive to the valency, geometry, composition, size, flexibility or rigidity, etc. of the linker and, in turn, on the overall structure of the multibinding compound, as well as the presence or absence of anionic or cationic charge, the relative hydrophobicity/hydrophilicity of the linker, and the like on the linker. Accordingly, the linker is preferably chosen to maximize the biological activity of the multibinding compound. The linker may be chosen to enhance the biological activity of the molecule. In general, the linker may be chosen from any organic molecule construct that orients two or more ligands to their ligand binding sites to permit multivalency. In this regard, the linker can be considered as a "framework" on which the ligands are arranged in order to bring about the desired ligand-orienting result, and thus produce a multibinding compound.

For example, different orientations can be achieved by including in the framework groups containing mono- or polycyclic groups, including aryl and/or heteroaryl groups, or structures incorporating one or more carbon-carbon multiple bonds (alkenyl, alkenylene, alkynyl or alkynylene groups). Other groups can also include oligomers and polymers which are branched- or straight-chain species. In preferred embodiments, rigidity is imparted by the presence of cyclic groups (e.g., aryl, heteroaryl, cycloalkyl, heterocyclic, etc.). In other preferred embodiments, the ring is a six or ten member ring. In still further preferred embodiments, the ring is an aromatic ring such as, for example, phenyl or naphthyl.

Different hydrophobic/hydrophilic characteristics of the linker as well as the presence or absence of charged moieties can readily be controlled by the skilled artisan. For example, the hydrophobic nature of a linker derived from hexamethylene diamine ($H_2N(CH_2)_6NH_2$) or related polyamines can be modified to be substantially more hydrophilic by replacing the alkylene group with a poly(oxyalkylene) group such as found in the commercially available "Jeffamines".

The intersection of the framework (linker) and the ligand group, and indeed, the framework (linker) itself can have many different bonding patterns. Examples of acceptable patterns of three contiguous atom arrangements are shown in the following diagram:

```
CCC NCC OCC SCC PCC

CCN NCN OCN SCN PCN

CCO NCO OCO SCO PCO

CCS NCS OCS SCS PCS

CCP NCP OCP SCP PCP

CNC NNC ONC SNC PNC

CNN NNN ONN SNN PNN

CNO NNO ONO SNO PNO

CNS NNS ONS SNS PNS

CNP NNP ONP SNP PNP

COC NOC OOC SOC POC

CON NON OON SON PON
```

```
COO  NOO  OOO  SOO  POO

COS  NOS  OOS  SOS  POS

COP  NOP  OOP  SOP  POP

CSC  NSC  OSC  SSC  PSC

CSN  NSN  OSN  SSN  PSN

CSO  NSO  OSO  SSO  PSO

CSS  NSS  OSS  SSS  PSS

CSP  NSP  OSP  SSP  PSP

CPC  NPC  OPC  SPC  PPC

CPN  NPN  OPN  SPN  PPN

CPO  NPO  OPO  SPO  PPO

CPS  NPS  OPS  SPS  PPS

CPP  NPP  OPP  SPP  PPP
```

One skilled in the art would be able to identify bonding patterns that would produce multivalent compounds. Methods for producing these bonding arrangements are described in March, "Advanced Organic Chemistry", 4th Edition, Wiley-Interscience, New York, N.Y. (1992). These arrangements are described in the grid of dots shown in the scheme above. All of the possible arrangements for the five most preferred atoms are shown. Each atom has a variety of acceptable oxidation states. The bonding arrangements underlined are less acceptable and are not preferred.

Examples of molecular structures in which the above bonding patterns could be employed as components of the linker are shown below.

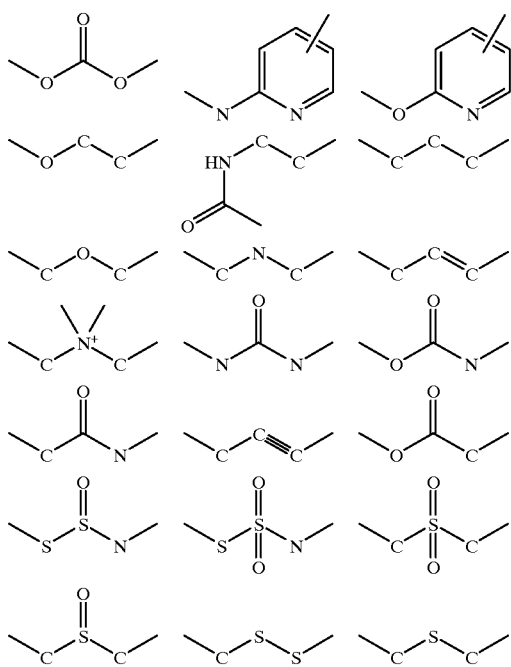

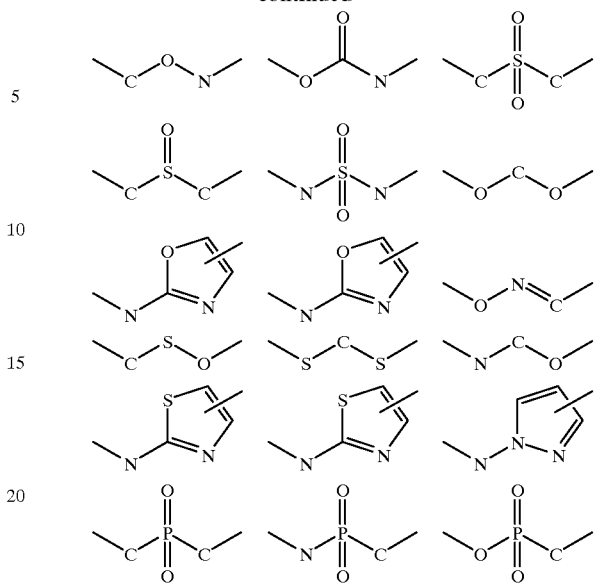

Figure 4:
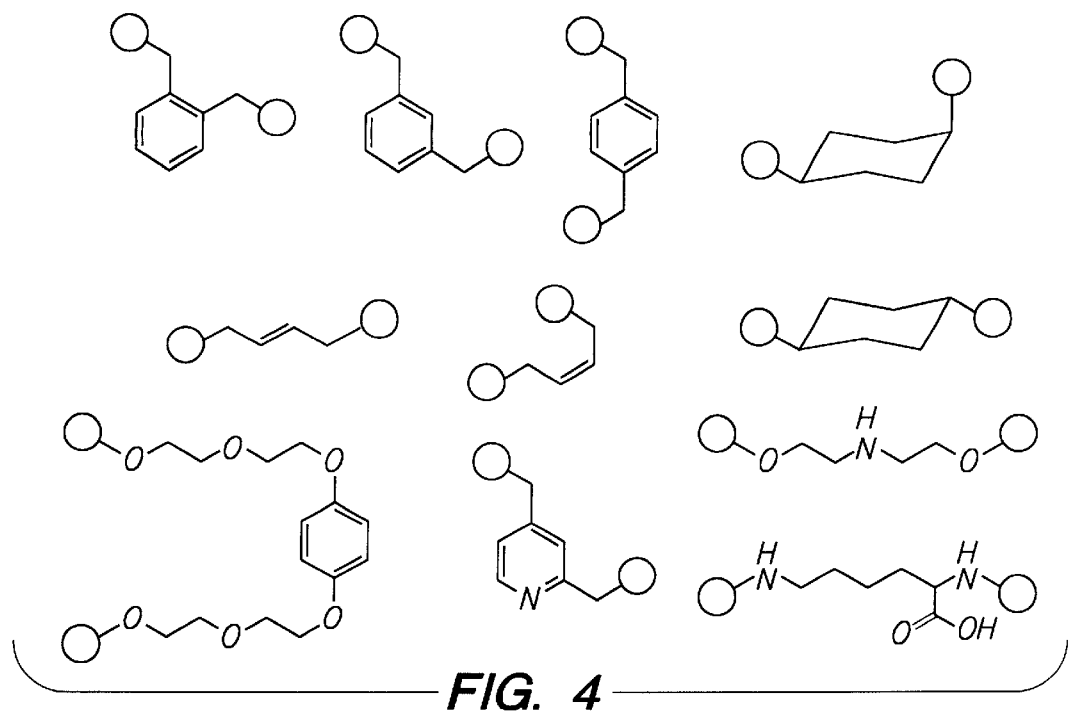
FIG. 4 illustrates examples of multibinding compounds comprising 2 ligands attached in different formats to a linker.

The identification of an appropriate framework geometry and size for ligand domain presentation are important steps in the construction of a multibinding compound with enhanced activity. Systematic spatial searching strategies can be used to aid in the identification of preferred frameworks through an iterative process. FIG. 4 illustrates a useful strategy for determining an optimal framework display orientation for ligand domains. Various other strategies are known to those skilled in the art of molecular design and can be used for preparing compounds of this invention.

As shown in FIG. 4, display vectors around similar central core structures such as a phenyl structure and a cyclohexane structure can be varied, as can the spacing of the ligand domain from the core structure (i.e., the length of the attaching moiety). It is to be noted that core structures other than those shown here can be used for determining the optimal framework display orientation of the ligands. The process may require the use of multiple copies of the same central core structure or combinations of different types of display cores.

Figure 5:
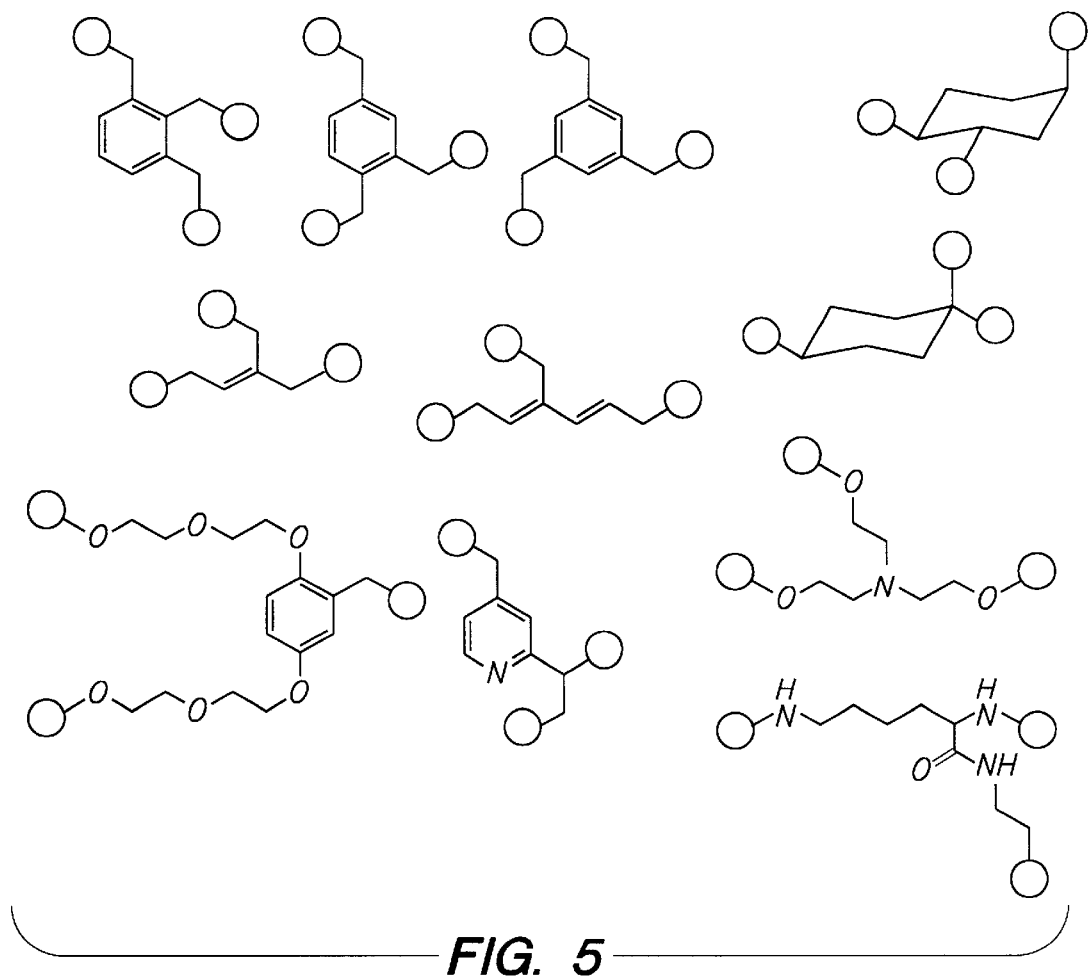
FIG. 5 illustrates examples of multibinding compounds comprising 3 ligands attached in different formats to a linker.
Figure 6:
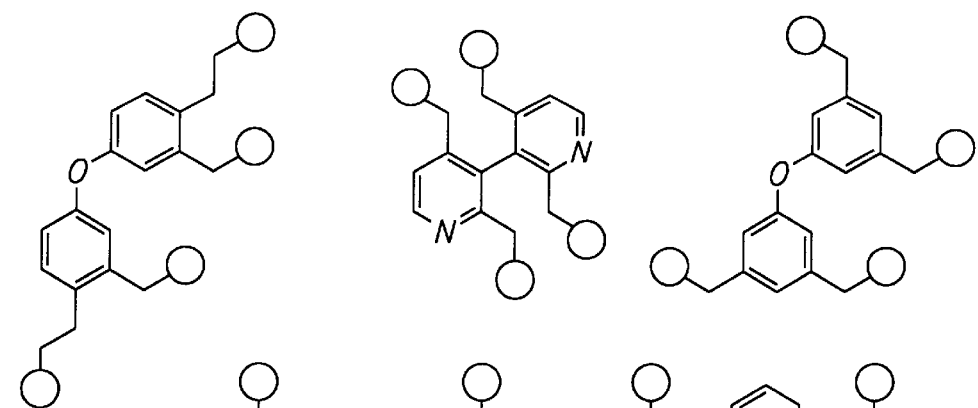
FIG. 6 illustrates examples of multibinding compounds comprising 4 ligands attached in different formats to a linker.
Figure 6:
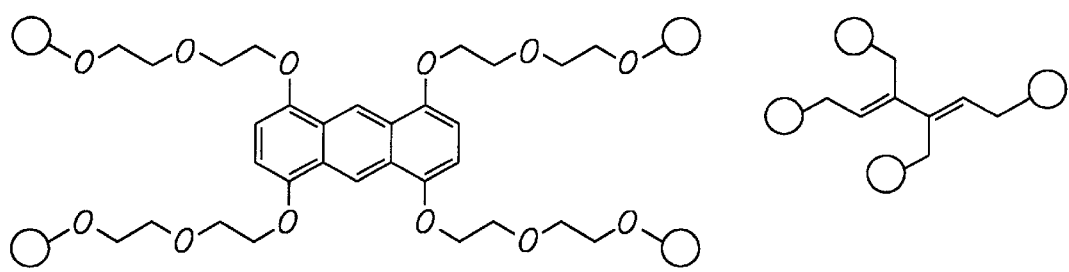
Figure 6:
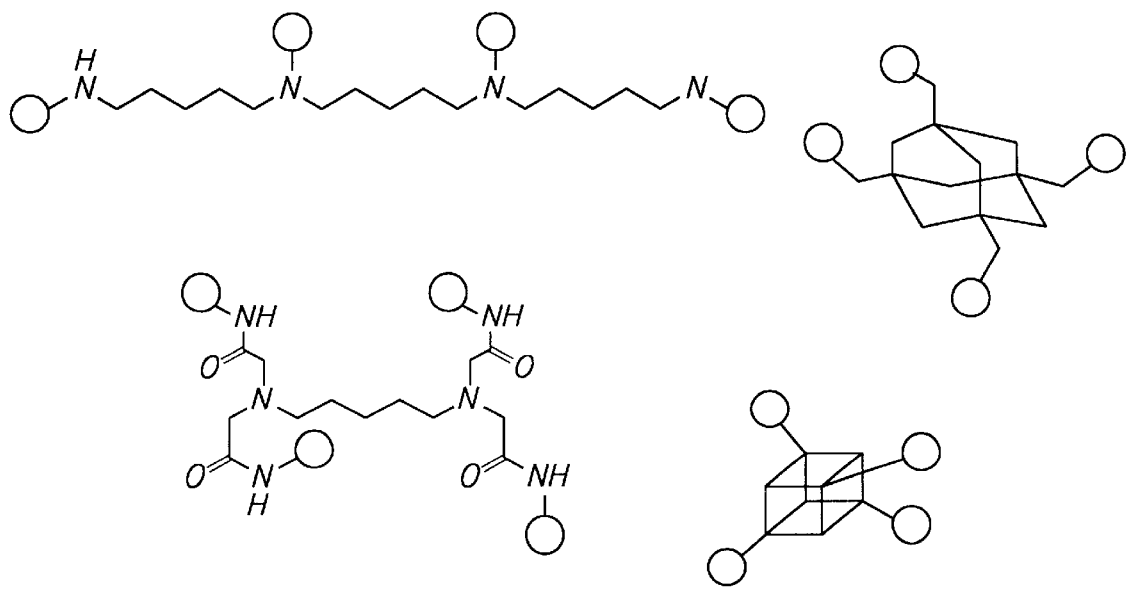
Figure 7:
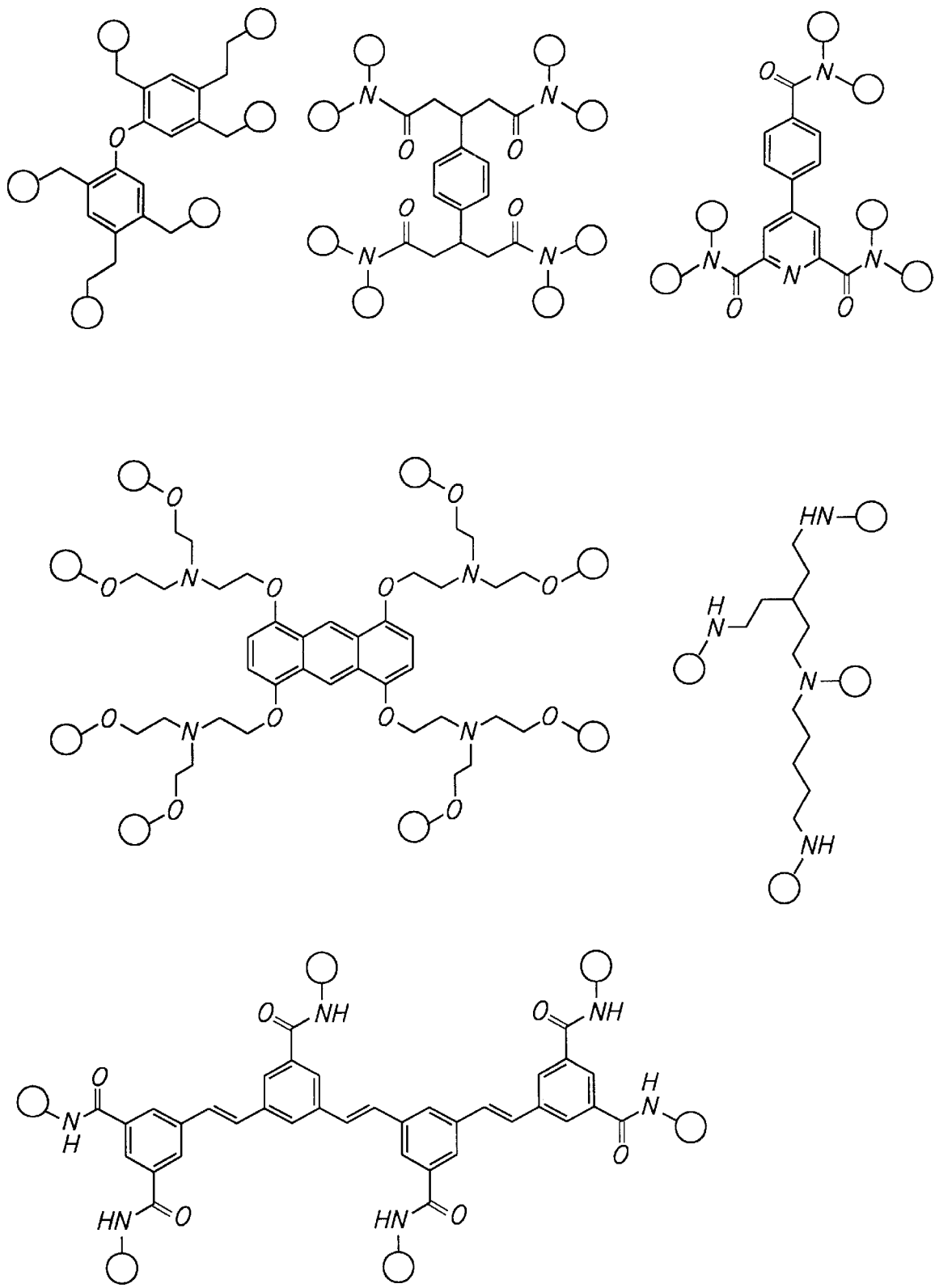
FIG. 7 illustrates examples of multibinding compounds comprising >4 ligands attached in different formats to a linker.
Figure 10:
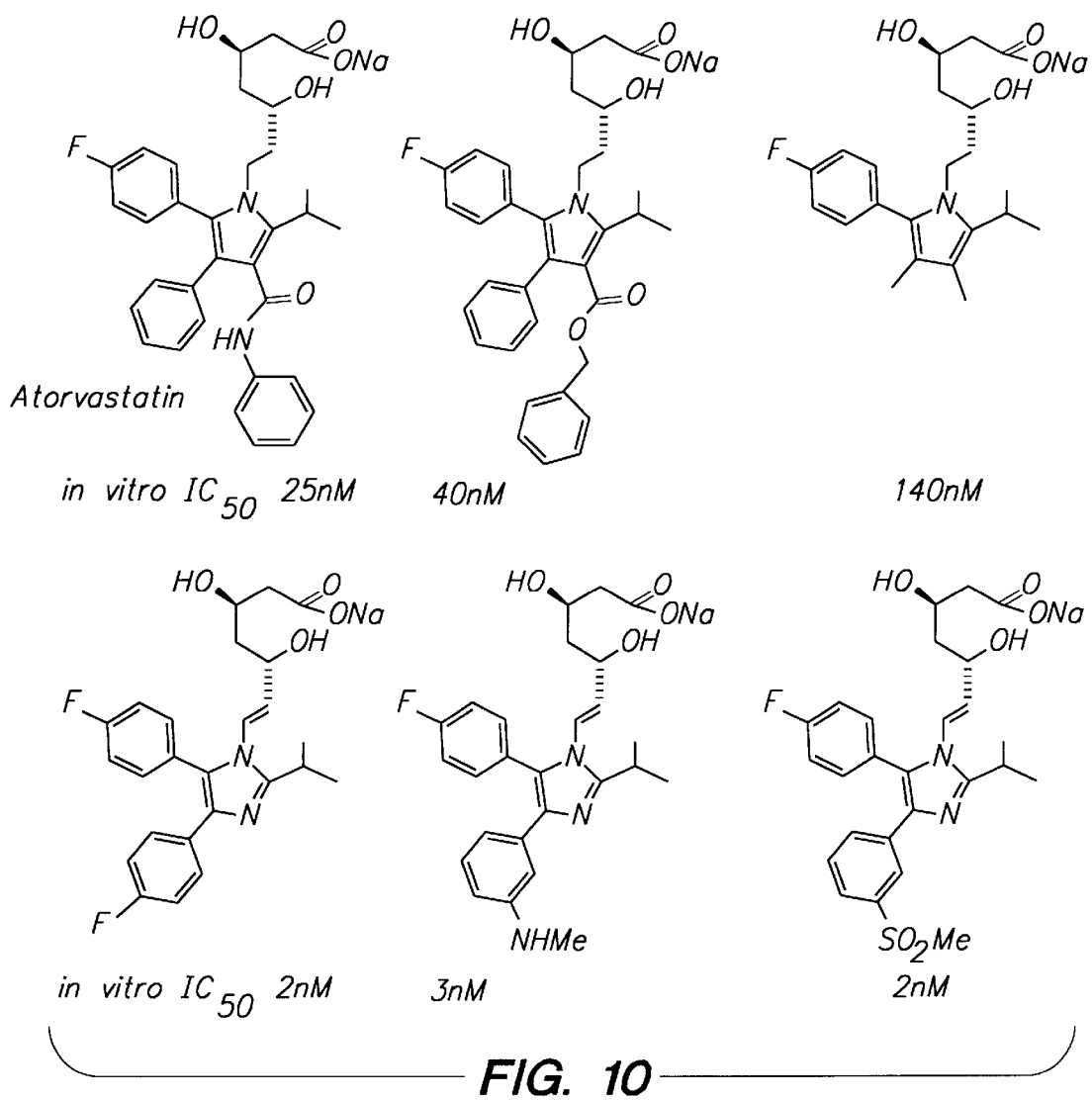
FIG. 10 shows various atorvastatin analogs having bulky substitutents in the "southern" binding domain and their in vitro activity.

The above-described process can be extended to trimers (FIG. 5) and compound of higher valency (FIGS. 6 and 7).

Assays of each of the individual compounds of a collection generated as described above will lead to a subset of compounds with the desired enhanced activities (e.g., potency, selectivity, etc.). The analysis of this subset using a technique such as Ensemble Molecular Dynamics will provide a framework orientation that favors the properties desired. A wide diversity of linkers is commercially available (see, e.g., Available Chemical Directory (ACD)). Many of the linkers that are suitable for use in this invention fall into this category. Other can be readily synthesized by methods well known in the art and/or are described below.

Having selected a preferred framework geometry, the physical properties of the linker can be optimized by varying the chemical composition thereof. The composition of the linker can be varied in numerous ways to achieve the desired physical properties for the multibinding compound.

It can therefore be seen that there is a plethora of possibilities for the composition of a linker. Examples of linkers include aliphatic moieties, aromatic moieties, steroidal moieties, peptides, and the like. Specific examples are peptides or polyamides, hydrocarbons, aromatic groups, ethers, lipids, cationic or anionic groups, or a combination thereof.

Examples are given below, but it should be understood that various changes may be made and equivalents may be substituted without departing from the true spirit and scope of the invention. For example, properties of the linker can be modified by the addition or insertion of ancillary groups into or onto the linker, for example, to change the solubility of the multibinding compound (in water, fats, lipids, biological fluids, etc.), hydrophobicity, hydrophilicity, linker flexibility, antigenicity, stability, and the like. For example, the introduction of one or more poly(ethylene glycol) (PEG) groups onto or into the linker enhances the hydrophilicity and water solubility of the multibinding compound, increases both molecular weight and molecular size and, depending on the nature of the unPEGylated linker, may increase the in vivo retention time. Further PEG may decrease antigenicity and potentially enhances the overall rigidity of the linker.

Ancillary groups which enhance the water solubility/hydrophilicity of the linker and, accordingly, the resulting multibinding compounds are useful in practicing this invention. Thus, it is within the scope of the present invention to use ancillary groups such as, for example, small repeating units of ethylene glycols, alcohols, polyols (e.g., glycerin, glycerol propoxylate, saccharides, including mono-, oligosaccharides, etc.), carboxylates (e.g., small repeating units of glutamic acid, acrylic acid, etc.), amines (e.g., tetraethylenepentamine), and the like) to enhance the water solubility and/or hydrophilicity of the multibinding compounds of this invention. In preferred embodiments, the ancillary group used to improve water solubility/hydrophilicity will be a polyether.

The incorporation of lipophilic ancillary groups within the structure of the linker to enhance the lipophilicity and/or hydrophobicity of the multibinding compounds described herein is also within the scope of this invention. Lipophilic groups useful with the linkers of this invention include, by way of example only, aryl and heteroaryl groups which, as above, may be either unsubstituted or substituted with other groups, but are at least substituted with a group which allows their covalent attachment to the linker. Other lipophilic groups useful with the linkers of this invention include fatty acid derivatives which do not form bilayers in aqueous medium until higher concentrations are reached.

Also within the scope of this invention is the use of ancillary groups which result in the multibinding compound being incorporated or anchored into a vesicle or other membranous structure such as a liposome or a micelle. The term "lipid" refers to any fatty acid derivative that is capable of forming a bilayer or a micelle such that a hydrophobic portion of the lipid material orients toward the bilayer while a hydrophilic portion orients toward the aqueous phase. Hydrophilic characteristics derive from the presence of phosphate, carboxylic, sulfato, amino, sulfhydryl, nitro and other like groups well known in the art. Hydrophobicity could be conferred by the inclusion of groups that include, but are not limited to, long chain saturated and unsaturated aliphatic hydrocarbon groups of up to 20 carbon atoms and such groups substituted by one or more aryl, heteroaryl, cycloalkyl, and/or heterocyclic group(s). Preferred lipids are phosphglycerides and sphingolipids, representative examples of which include phosphatidylcholine, phosphatidylethanolamine, phosphatidylserine, phosphatidylinositol, phosphatidic acid, pahnitoyleoyl phosphatidylcholine, lysophosphatidylcholine, lysophosphatidyl-ethanolamine, dipalmitoylphosphatidylcholine, dioleoylphosphatidylcholine, distearoylphosphatidylcholine or dilinoleoylphosphatidylcholine could be used. Other compounds lacking phosphorus, such as sphingolipid and glycosphingolipid families are also within the group designated as lipid. Additionally, the amphipathic lipids described above may be mixed with other lipids including triglycerides and sterols.

The flexibility of the linker can be manipulated by the inclusion of ancillary groups which are bulky and/or rigid. The presence of bulky or rigid groups can hinder free rotation about bonds in the linker or bonds between the linker and the ancillary group(s) or bonds between the linker and the functional groups. Rigid groups can include, for example, those groups whose conformational lability is restrained by the presence of rings and/or multiple bonds within the group, for example, aryl, heteroaryl, cycloalkyl, cycloalkenyl, and heterocyclic groups. Other groups which can impart rigidity include polypeptide groups such as oligo- or polyproline chains.

Rigidity can also be imparted electrostatically. Thus, if the ancillary groups are either positively or negatively charged, the similarly charged ancillary groups will force the presenter linker into a configuration affording the maximum distance between each of the like charges. The energetic cost of bringing the like-charged groups closer to each other will tend to hold the linker in a configuration that maintains the separation between the like-charged ancillary groups. Further ancillary groups bearing opposite charges will tend to be attracted to their oppositely charged counterparts and potentially may enter into both inter- and intramolecular ionic bonds. This non-covalent mechanism will tend to hold the linker into a conformation which allows bonding between the oppositely charged groups. The addition of ancillary groups which are charged, or alternatively, bear a latent charge when deprotected, following addition to the linker, include deprotectation of a carboxyl, hydroxyl, thiol or amino group by a change in pH, oxidation, reduction or other mechanisms known to those skilled in the art which result in removal of the protecting group, is within the scope of this invention.

Rigidity may also be imparted by internal hydrogen bonding or by hydrophobic collapse.

Bulky groups can include, for example, large atoms, ions (e.g., iodine, sulfur, metal ions, etc.) or groups containing large atoms, polycyclic groups, including aromatic groups, non-aromatic groups and structures incorporating one or more carbon-carbon multiple bonds (i.e., alkenes and alkynes). Bulky groups can also include oligomers and polymers which are branched- or straight-chain species. Species that are branched are expected to increase the rigidity of the structure more per unit molecular weight gain than are straight-chain species.

In preferred embodiments, rigidity is imparted by the presence of cyclic groups (e.g., aryl, heteroaryl, cycloalkyl, heterocyclic, etc.). In other preferred embodiments, the linker comprises one or more six-membered rings. In still further preferred embodiments, the ring is an aryl group such as, for example, phenyl or naphthyl.

In view of the above, it is apparent that the appropriate selection of a linker group providing suitable orientation, restricted/unrestricted rotation, the desired degree of hydrophobicity/hydrophilicity, etc. is well within the skill of the art. Eliminating or reducing antigenicity of the multibinding compounds described herein is also within the scope of this invention. In certain cases, the antigenicity of a multibinding compound may be eliminated or reduced by use of groups such as, for example, poly(ethylene glycol).

As explained above, the multibinding compounds described herein comprise 2–10 ligands attached to a linker that links the ligands in such a manner that they are presented to the enzyme for multivalent interactions with ligand binding sites thereon/therein. The linker spatially constrains these interactions to occur within dimensions defined by the linker. This and other factors increases the biological activity of the multibinding compound as compared to the same number of ligands made available in monobinding form.

The compounds of this invention are preferably represented by the empirical formula $(L)_p(X)_q$ where L, X, p and q are as defined above. This is intended to include the several ways in which the ligands can be linked together in order to achieve the objective of multivalency, and a more detailed explanation is described below.

As noted previously, the linker may be considered as a framework to which ligands are attached. Thus, it should be recognized that the ligands can be attached at any suitable position on this framework, for example, at the termini of a linear chain or at any intermediate position.

The simplest and most preferred multibinding compound is a bivalent compound which can be represented as L—X—L, where each L is independently a ligand which may be the same or different and each X is independently the linker. Examples of such bivalent compounds are provided in FIG. 4 where each shaded circle represents a ligand. A trivalent compound could also be represented in a linear fashion, i.e., as a sequence of repeated units L—X—L—X—L, in which L is a ligand and is the same or different at each occurrence, as can X. However, a trimer can also be a radial multibinding compound comprising three ligands attached to a central core, and thus represented as $(L)_3X$, where the linker X could include, for example, an aryl or cycloalkyl group. Illustrations of trivalent and tetravalent compounds of this invention are found in FIGS. 5 and 6 respectively where, again, the shaded circles represent ligands. Tetravalent compounds can be represented in a linear array, e.g.,

L—X—L—X—L—X—L in a branched array, e.g.,

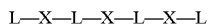
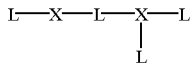

(a branched construct analogous to the isomers of butane—n-butyl, iso-butyl, sec-butyl, and t-butyl) or in a tetrahedral array, e.g.,

where X and L are as defined herein. Alternatively, it could be represented as an alkyl, aryl or cycloalkyl derivative as above with four (4) ligands attached to the core linker.

The same considerations apply to higher multibinding compounds of this invention containing 5–10 ligands as illustrated in FIG. 7 where, as before, the shaded circles represent ligands. However, for multibinding agents attached to a central linker such as aryl or cycloalkyl, there is a self-evident constraint that there must be sufficient attachment sites on the linker to accommodate the number of ligands present; for example, a benzene ring could not directly accommodate more than 6 ligands, whereas a multi-ring linker (e.g., biphenyl) could accommodate a larger number of ligands.

Certain of the above described compounds may alternatively be represented as cyclic chains of the form:

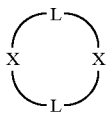

and variants thereof.

All of the above variations are intended to be within the scope of the invention defined by the formula $(L)_p(X)_q$.

With the foregoing in mind, a preferred linker may be represented by the following formula:

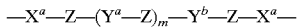

in which:

m is an integer of from 0 to 20;

$X^a$ at each separate occurrence is selected from the group consisting of —O—, —S—, —NR—, —C(O)—, —C(O)O—, —C(O)NR—, —C(S), —C(S)O—, —C(S)NR— or a covalent bond where R is as defined below;

Z is at each separate occurrence is selected from the group consisting of alkylene, substituted ,lene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;

$Y^a$ and $Y^b$ at each separate occurrence are selected from the group consisting of:

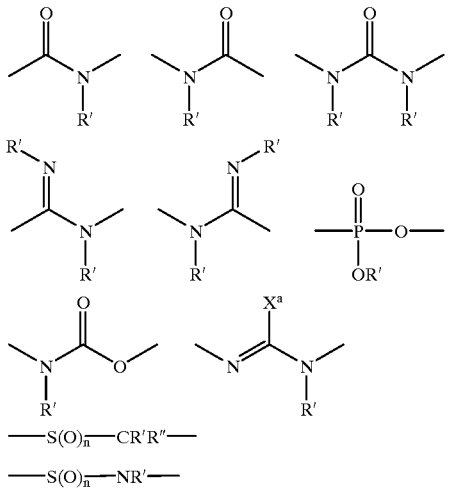

—S—S— or a covalent bond;

in which:

n is 0, 1 or 2; and

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

Additionally, the linker moiety can be optionally substituted at any atom therein by one or more alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic group.

In one embodiment of this invention, the linker (i.e., X, X' or X") is selected those shown in Table II:

TABLE II

Representative Linkers

Linker

—HN—(CH$_2$)$_2$—NH—C(O)—(CH$_2$)—C(O)—NH—(CH$_2$)$_2$—NH—
—HN—(CH$_2$)$_2$—NH—C(O)—(CH$_2$)$_2$—C(O)—NH—(CH$_2$)$_2$—NH—
—HN—(CH$_2$)$_2$—NH—C(O)—(CH$_2$)$_3$—C(O)—NH—(CH$_2$)$_2$—NH—
—HN—(CH$_2$)$_2$—NH—C(O)—(CH$_2$)$_4$—C(O)—NH—(CH$_2$)$_2$—NH—
—HN—(CH$_2$)$_2$—NH—C(O)—(CH$_2$)$_5$—C(O)—NH—(CH$_2$)$_2$—NH—
—HN—(CH$_2$)$_2$—NH—C(O)—(CH$_2$)$_6$—C(O)—NH—(CH$_2$)$_2$—NH—
—HN—(CH$_2$)$_2$—NH—C(O)—(CH$_2$)$_7$—C(O)—NH—(CH$_2$)$_2$—NH—
—HN—(CH$_2$)$_2$—NH—C(O)—(CH$_2$)$_8$—C(O)—NH—(CH$_2$)$_2$—NH—
—HN—(CH$_2$)$_2$—NH—C(O)—(CH$_2$)$_9$—C(O)—NH—(CH$_2$)$_2$—NH—
—HN—(CH$_2$)$_2$—NH—C(O)—(CH$_2$)$_{10}$—C(O)—NH—(CH$_2$)$_2$—NH—
—HN—(CH$_2$)$_2$—NH—C(O)—(CH$_2$)$_{11}$—C(O)—NH—(CH$_2$)$_2$—NH—
—HN—(CH$_2$)$_2$—NH—C(O)—(CH$_2$)$_{12}$—C(O)—NH—(CH$_2$)$_2$—NH—
—HN—(CH$_2$)$_2$—NH—C(O)-Z-C(O)—NH—(CH$_2$)$_2$—NH—where Z is 1,2—phenyl
—HN—(CH$_2$)$_2$—NH—C(O)-Z-C(O)—NH—(CH$_2$)$_2$—NH—where Z is 1,3—phenyl
—HN—(CH$_2$)$_2$—NH—C(O)-Z-C(O)—NH—(CH$_2$)$_2$—NH—where Z is 1,4—phenyl
—HN—(CH$_2$)$_2$—NH—C(O)-Z-O-Z-C(O)—NH—(CH$_2$)$_2$—NH—where Z is 1,4—phenyl
—HN—(CH$_2$)$_2$—NH—C(O)—(CH$_2$)$_2$—CH(NH—C(O)—(CH$_2$)$_8$—CH$_3$)—C(O)—NH—(CH$_2$)$_2$—NH—
—HN—(CH$_2$)$_2$—NH—C(O)—(CH$_2$)—O—(CH$_2$)—C(O)—NH—(CH$_2$)$_2$—NH—
—HN—(CH$_2$)$_2$—NH—C(O)-Z-C(O)—NH—(CH$_2$)$_2$—NH—
where Z is 5-(n-octadecyloxy)-1,3-phenyl
—HN—(CH$_2$)$_2$—NH—C(O)—(CH$_2$)$_2$—CH(NH—C(O)-Z)—C(O)—NH—(CH$_2$)$_2$—NH—
where Z is 4-biphenyl
—HN—(CH$_2$)$_2$—NH—C(O)-Z-C(O)—NH—(CH$_2$)$_2$—NH—
where Z is 5-(n-butyloxy)-1,3-phenyl
—HN—(CH$_2$)$_2$—NH—C(O)—(CH$_2$)$_8$—trans—(CH=CH)—C(O)—NH—(CH$_2$)$_2$—NH—
—HN—(CH$_2$)$_2$—NH—C(O)—(CH$_2$)$_2$—CH(NH—C(O)—(CH$_2$)12—CH3)—C(O)—NH—(CH$_2$)$_2$—NH—
—HN—(CH$_2$)$_2$—NH—C(O)—(CH$_2$)$_2$—CH(NH—C(O)-Z)—C(O)—NH—(CH$_2$)$_2$—NH—
where Z is 4-(n-octyl)-phenyl
—HN—(CH$_2$)-Z-O—(CH$_2$)$_6$—O-Z-(CH$_2$)—NH—where Z is 1,4-phenyl
—HN—(CH$_2$)$_2$—NH—C(O)—(CH$_2$)$_2$—NH—C(O)—(CH$_2$)$_3$—C(O)—NH—(CH$_2$)$_2$—C(O)—NH—(CH$_2$)$_2$—NH—
—HN—(CH$_2$)$_2$—NH—C(O)—(CH$_2$)$_2$—CH(NH—C(O)—Ph)—C(O)—NH—(CH$_2$)$_2$—NH—
—HN—(CH$_2$)$_2$—NH—C(O)—(CH$_2$)—N+((CH$_2$)$_9$—CH$_3$)(CH$_2$—C(O)—NH—(CH$_2$)$_2$—NH$_2$)—(CH$_2$)—C(O)—NH—(CH$_2$)$_2$—NH—
—HN—(CH$_2$)$_2$—NH—C(O)—(CH$_2$)—N((CH$_2$)$_9$—CH$_3$)—(CH$_2$)—C(O)—NH—(CH$_2$)$_2$—NH—
—HN—(CH$_2$)$_2$—NH—C(O)—(CH$_2$)$_2$—NH—C(O)—(CH$_2$)$_2$—NH—C(O)—(CH$_2$)$_3$—C(O)—NH—(CH$_2$)$_2$—C(O)—NH—(CH$_2$)$_2$—C(O)—NH—(CH$_2$)$_2$—NH—
—HN—(CH$_2$)$_2$—NH—C(O)-Z-C(O)—NH—(CH$_2$)$_2$—NH—
where Z is 5-hydroxy-1,3-phenyl In another embodiment of this invention, the linker (i.e., X, X' or X") has the formula:

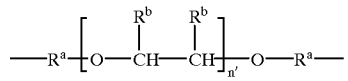

wherein
each $R^a$ is independently selected from the group consisting of a covalent bond, alkylene, substituted alkylene and arylene;
each $R^b$ is independently selected from the group consisting of hydrogen, alkyl and substituted alkyl; and
n' is an integer ranging from 1 to about 20.
In yet another embodiment, the linker (i.e., X or X') has the formula: —(CH$_2$)$_{n'}$—, where n' is an integer ranging from I to about 20, preferably from 2 to 6.
In view of the above description of the linker, it is understood that the term "linker" when used in combination with the term "multibinding compound" includes both a covalently contiguous single linker (e.g., L—X—L) and multiple covalently non-contiguous linkers (L—X—L—X—L) within the multibinding compound.

Preparation of Multibinding Compounds

The multibinding compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Second Edition, Wiley, New York, 1991, and references cited therein.

Any compound which binds to or inhibits HMG-CoA reductase can be used as a ligand in this invention. As discussed in further detail below, numerous such HMG-CoA reductase inhibitors are known in the art and any of these known compounds or derivatives thereof may be employed as ligands in this invention. Typically, a compound selected for use as a ligand will have at least one functional group, such as an amino, hydroxyl, thiol or carboxyl group and the like, which allows the compound to be readily coupled to the linker. Compounds having such functionality are either known in the art or can be prepared by routine modification of known compounds using conventional reagents and procedures. The patents and publications set forth below provide numerous examples of suitably functionalized HMG-CoA reductase inhibitors and intermediates thereof which may be used as ligands in this invention.

Figure 3:
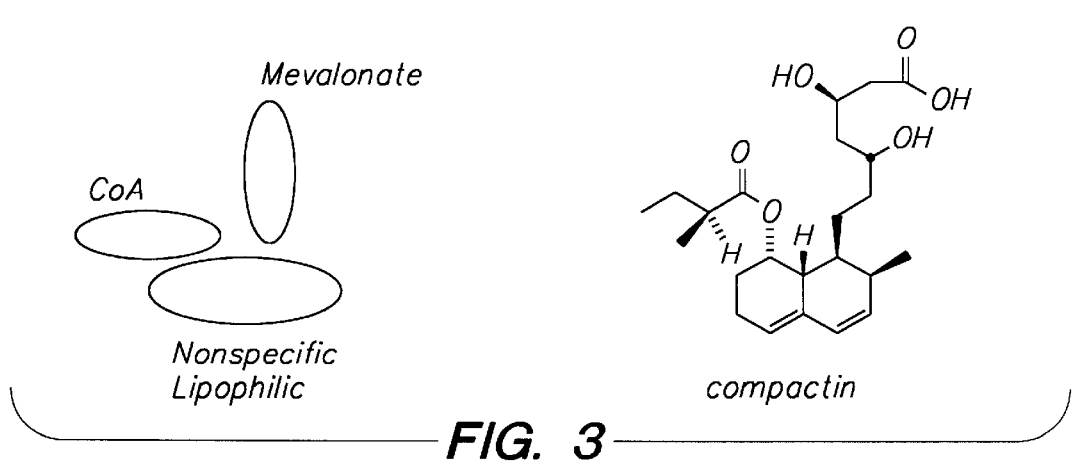
FIG. 3 illustrates a binding model for the statins and the chemical structure of a representative statin, i.e., mevastatin (compactin).

The ligand can be covalently attached to the linker through any available position on the ligand, provided that when the ligand is attached to the linker, the ligand retains its ability to bind to or inhibit HMG-CoA reductase. Certain sites of attachment of the linker to the ligand are preferred based on proposed binding models[7] and known structure-activity relationships.[8-4] In this regard, a proposed binding model for the statins is shown in FIG. 3. Known HMG-CoA reductase inhibitors, such as mevastatin, typically contain a mevalonate-type moiety or a derivative thereof (i.e., $A^1$ and $A^2$ as defined herein) in the "northern" binding domain of the inhibitor. Preferably, the linker is not attached through this mevalonate-type moiety, but is instead, covalently attached to the "southern" binding domain of the inhibitor, i.e., the nonspecific lipophilic binding domain of the inhibitor opposite the mevalonate moiety. The ability of the statins to accept bulky substitution in the "southern" binding domain is demonstrated in FIGS. 8–11 which illustrate various derivatives of simnvastatin, fluvastatin, atorvastatin and cerivastatin, respectively, having relatively bulky substituents in "southern" binding domain of the inhibitor and which retain good in vitro activity. Accordingly, covalent attachment of the linker to the "southern" binding domain of the inhibitor is preferred.

The only HMG-CoA reductase-like enzyme which has been studied by crystallography is from *Pseudomonas mevalonii*.[15] While there are some differences between this enzyme and the mammalian reductases, this crystallography study of this enzyme may provide some insight into the binding site for reductases in general. While not intending to be limited to theory, the crystallography study shows that the packing of the subunits in the crystal reveals a dimer with an extensive intersubunit interface formed by the two monomers. Twenty eight percent of the total monomer surface is buried at the dimer interface. The dimer is T-shaped with dimensions of 70 Å by 60 Å by 50 Å. The dimer axis runs vertically through the stem of the T. The foot of the T contains the amino termini of the two monomers and is the position where the membrane anchoring segments of the mammalian enzymes reside. Two active sites are located at the intersection of the stem of the T with the arms. Interestingly, in the active site the NAD(H) binding site resides on one subunit while the HMG-CoA site resides on the other subunit. The thioester of the HMG-CoA and the C-4 of the nocotinamide ring of the NAD(H) are within 3.5 Å. This may explain why the monomers are inactive even though each monomer binds one HMG-CoA and one NAD(H). Thus, in the monomeric configuration, the two substrates are not close enough for hydride transfer.

A first group of preferred ligands for use in this invention are those ligands having formula IA:

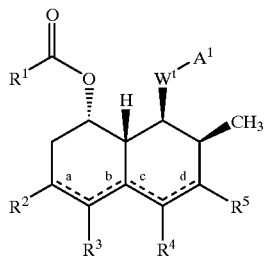

IA wherein $A^1$, $R^1$, $R^2$, $R^3$, $R^4$, $R^5$, $W^1$ and a, b, c and d are as defined herein. Such ligands include derivatives of mevastatin (compacting, lovastatin, simvastatin, pravastatin and the like.

Ligands of formula IA (and the precursors thereof) are well-known in the art and can be readily prepared using art-recognized starting materials, reagents and reaction conditions. By way of illustration, the following patents and publications disclose compounds, intermediates and procedures useful in the preparation of ligands of formula IA or related compounds suitable for use in this invention: U.S. Pat. No. 3,983,140, issued Sep. 28, 1976 to Endo et al.; U.S. Pat. No. 4,049,495, issued Sep. 20, 1997 to Endo et al.; U.S. Pat. No. 4,137,322, issued Jan. 30, 1979 to Endo et al.; U.S. Pat. No. 4,231,938, issued Nov. 4, 1980 to Monaghan et al.; U.S. Pat. No. 4,293,496, issued Oct. 6, 1981 to Willard; U.S. Pat. No. 4,294,846, issued Oct. 13, 1981 to Albers-Schonberg et al; U.S. Pat. No. 4,346,227, issued Aug. 24, 1982 to Terahara et al.; U.S. Pat. No. 4,351,844, issued Sep. 28, 1982 to Patchett et al.; U.S. Pat. No. 4,361,515, issued Nov. 30, 1982 to Terahara et al.; U.S. Pat. No. 4,410,629, issued Oct. 18, 1983 to Terahara et al.; U.S. Pat. No. 4,420,491, issued Dec. 13, 1983 to Albers-Schnonberg et al.; U.S. Pat. No. 4,438,277, issued Mar. 20, 1984 to Terahara et al.; U.S. Pat. No. 4,447,626, issued May 8, 1984 to Terahara et al.; U.S. Pat. No. 4,448,979, issued May 15, 1984 to Terahara et al.; U.S. Pat. No. 4,490,546, issued Dec. 25, 1984 to Kuo; U.S. Pat. No. 4,503,072, issued Mar. 5, 1985 to Hoffmnan et al.; U.S. Pat. No. 4,517,373, issued May 14, 1985 to Terahara et al.; U.S. Pat. No. 4,537,859, issued Aug. 27, 1985 to Terahara et al.; U.S. Pat. No. 4,604,472, issued Aug. 5, 1986 to Ide et al.; U.S. Pat. No. 4,661,483, issued Apr. 28, 1987 to Hoffmnan et al.; U.S. Pat. No. 4,668,699, issued May 26, 1987 to Hoffmnan et al.; U.S. Pat. No. 4,678,806, issued Jul. 7, 1987 to Baldwin et al.; U.S. Pat. No. 4,719,229, issued Jan. 12, 1988 to Reamer et al.; U.S. Pat. No. 4,733,003, issued Mar. 22, 1988 to Ide et al.; U.S. Pat. No. 4,736,064, issued Apr. 5, 1988 to Baldwin et al.; U.S. Pat. No. 4,738,982, issued Apr. 19, 1988 to Arison et al., U.S. Pat. No. 4,766,145, issued Aug. 23, 1988 to Lee et al.; U.S. Pat. No. 4,771,071, issued Sep. 13, 1988 to Hoffmnan et al.; U.S. Pat. No. 4,782,084, issued Nov. 1, 1988 to Vyas et al.; U.S. Pat. No. 4,795,811, issued Jan. 3, 1989 to Graham et al.; U.S. Pat. No. 4,837,205, issued Jun. 6, 1989 to Halczenko et al.; U.S. Pat. No. 4,851,436, issued Jul. 25, 1989 to Hoffmnan et al.; U.S. Pat. No. 4,855,456, issued Aug. 8, 1989 to Lee et al; U.S. Pat. No. 4,855,481, issued Aug. 8, 1989 to Guindon, et al.; U.S. Pat. No. 4,857,546, issued Aug. 15, 1989 to Duggan et al.; U.S. 4,864,035, issued Sep. 5, 1989 to DeCamp et al.; U.S. Pat. No. 4,864,038, issued Sep. 5, 1989 to Hoffmnan et al.; U.S. Pat. No. 4,866,068, issued Sep. 12, 1989 to Rooney; U.S. Pat. No. 4,866,090, issued Sep. 12, 1989 to Hoffinan et al.; U.S. Pat. No. 4,866,186, issued Sep. 12, 1989 to Thompson et al.;

U.S. Pat. No. 4,873,345, issued Oct. 10, 1989 to Duggan; U.S. Pat. No. 4,874,870, issued Oct. 17, 1989 to Graham et al.; U.S. Pat. No. 4,876,279, issued Oct. 24, 1989 to Lee et al.; U.S. Pat. No. 4,885,314, issued Dec. 5, 1989 to Vyas et al.; U.S. Pat. No. 4,894,465, issued Jan. 16, 1990 to Lee et al.; U.S. Pat. No. 4,894,466, issued Jan. 16, 1990 to Lee et al.; U.S. Pat. No. 4,897,402, issued Jan. 30, 1990 to Duggan et al.; U.S. Pat. No. 4,902,709, issued Feb. 20, 1990 to Stokker; U.S. Pat. No. 4,916,162, issued Apr. 10, 1990 to Hoffmman et al.; U.S. Pat. No. 4,916,239, issued Apr. 10, 1990 to Treiber; U.S. Pat. No. 4,921,974, issued May 1, 1990 to Duggan; U.S. Pat. No. 4,937,259, issued Jun. 26, 1990 to Lee; U.S. Pat. No. 4,937,264, issued Jun. 26, 1990 to Hoffman et al.; U.S. Pat. No. 4,940,727, issued Jul. 10, 1990 to Inamine et al.; U.S. Pat. No. 4,943,588, issued Jul. 24, 1990 to Halczenko et al.; U.S. Pat. No. 4,950,775, issued Aug. 21, 1990 to Heathcock et al.; U.S. Pat. No. 4,963,538, issued Oct. 16, 1990 to Duggan et al.; U.S. Pat. No. 4,946,864, issued Aug. 7, 1990 to Prugh et al.; U.S. Pat. No. 4,965,200, issued Oct. 23, 1990 to Chen et al.; U.S. Pat. No. 4,970,231, issued Nov. 13, 1990 to Lee et al.; U.S. Pat. No. 4,997,755, issued Mar. 5, 1991 to Williamson et al.; U.S. Pat. No. 4,997,848, issued Mar. 5, 1991 to Kurabayashi et al.; U.S. Pat. No. 4,997,849, issued Mar. 5, 1991 to Petuch et al.; U.S. Pat. No. 5,001,148, issued Mar. 19, 1991 to Saunders et al.; U.S. Pat. No. 5,010,105, issued Apr. 23, 1991 to Lee; U.S. Pat. No. 5,041,562, issued Aug. 20, 1991 to Stokker et al.; U.S. Pat. No. 5,049,696, issued Sep. 17, 1991 to Lee et al.; U.S. Pat. No. 5,053,525, issued Oct. 1, 1991 to Hoffinan et al.; U.S. Pat. No. 5,059,696, issued Oct. 22, 1991 to Anderson et al.; U.S. Pat. No. 5,089,523, issued Feb. 18, 1992 to Varma et al.; U.S. Pat. No. 5,098,931, issued Mar. 24, 1992 to Duggan et al.; U.S. Pat. No. 5,099,035, issued Mar. 24, 1992 to Saunders et al.; U.S. Pat. No. 5,102,911, issued Apr. 7, 1992 to Lee et al.; U.S. Pat. No. 5,112,857, issued May 12, 1992 to Vickers; U.S. Pat. No. 5,116,870, issued May 26, 1992 to Smith, et al.; U.S. Pat. No. 5,130,306, issued Jul. 14, 1992 to Duggan et al.; U.S. Pat. No. 5,151,365, issued Sep. 29, 1992 to Dombrowski et al.; U.S. Pat. No. 5,153,124, issued Oct. 6, 1992 to Furuya et al.; U.S. Pat. No. 5,159,104, issued Oct. 27, 1992 to Dabora et al.; U.S. Pat. No. 5,166,364, issued Nov. 24, 1992 to Saunders et al; U.S. Pat. No. 5,173,487, issued Dec. 22, 1992 to Saunders et al.; U.S. Pat. No. 5,177,104, issued Jan. 5, 1993 to Varma et al.; U.S. Pat. No. 5,189,180, issued Feb. 23, 1993 to Karanewsky; U.S. Pat. No. 5,208,258, issued May 4, 1993 to Heathcock et al.; U.S. Pat. No. 5,210,228, issued May 11, 1993 to Todd et al.; U.S. Pat. No. 5,223,415, issued Jun. 29, 1993 to Conder et al.; U.S. Pat. No. 5,244,795, issued Sep. 14, 1993 to Dombrowski et al.; U.S. Pat. No. 5,250,435, issued Oct. 5, 1993 to Cover et al.; U.S. Pat. No. 5,245,050, issued Sep. 14, 1993 to Endo et al.; U.S. Pat. No. 5,256,811, issued Oct. 26, 1993 to Todd et al.; U.S. Pat. No. 5,264,455, issued Nov. 23, 1993 to Varma et al.; U.S. Pat. No. 5,272,174, issued Dec. 21, 1993 to FuruY$^a$ et al.; U.S. Pat. No. 5,276,154, issued Jan. 4, 1994 to Hiyama et al.; U.S. Pat. No. 5,286,746, issued Feb. 15, 1994 to Poss; U.S. Pat. No. 5,308,864, issued May 3, 1994 to Lewis et al.; U.S. Pat. No. 5,369,123, issued Nov. 29, 1994 to Santafianos et al.; U.S. Pat. No. 5,385,932, issued Jan. 31, 1995 to Vickers; U.S. Pat. No. 5,409,820, issued Apr. 25, 1995 to Gerson et al.; U.S. Pat. No. 5,420,024, issued May 30, 1995 to Carta et al.; U.S. Pat. No. 5,451,688, issued Sep. 19, 1995 to Kogen et al.; U.S. Pat. No. 5,491,167, issued Feb. 13, 1996 to Ishihara et al.; U.S. Pat. No. 5,604,256, issued Feb. 18, 1997 to Kogen et al.; U.S. Pat. No. 5,620,876, issued Apr. 15, 1997 to Davis et al.; U.S. Pat. No. 5,658,942, issued Aug. 19, 1997 to Kurabayashi et al.; U.S. Pat. No. 5,763,646, issued Jun. 9, 1998 to Kumar et al.; U.S. Pat. No. 5,763,653, issued Jun. 9, 1998 to Khanna et al.; EP 0 251 625 B1, published Jan. 7, 1988 to Inamine et al.; EP 0 323 867 A1, published Dec. 7, 1989 to Hoffman et al.; and WO 94/29292, published Dec. 22, 1994 to Hajko et al. Each of these patents and publications is incorporated herein by reference in its entirety to the same extent as if each individual patent or publication was specifically and individually indicated to be incorporated by reference in its entirety.

A second group of preferred ligands for use in this invention are those ligands having formula IB:

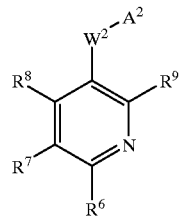

IB wherein $A^2$, $R^6$, $R^7$, $R^8$, $R^9$ and $W^2$ are as defined herein. Such ligands include, but are not limited to, derivatives of cerivastatin and the like.

Ligands of formula IB (and the precursors thereof) are also well-known in the art and can be readily prepared using art-recognized starting materials, reagents and reaction conditions. For example, the following patents and publications disclose compounds, intermediates and procedures useful in the preparation of ligands of formula IB or related compounds suitable for use as ligands in this invention: U.S. Pat. No. 5,402,746, issued Mar. 28, 1995 to Angerbauer et al.; U.S. Pat. No. 5, 409,910, issued Apr. 25, 1995 to Angerbauer et al.; U.S. Pat. No. 5,691,322, issued Nov. 25, 1997 to Robl; J. A. Robl et al., *J. Med. Chem.*, 1991, 34, 2804–2815. Each of these patents and publications is incorporated herein by reference in its entirety to the same extent as if each individual patent or publication was specifically and individually indicated to be incorporated by reference in its entirety.

A third group of preferred ligands for use in this invention are those ligands having formula IC:

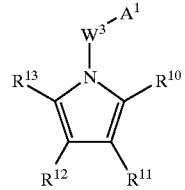

IC wherein $A^1$, $R^{10}$, $R^{11}$, $R^{12}$, $R^{13}$ and $W^3$ are as defined herein. Such ligands include, but are not limited to, derivatives of atorvastatin and the like.

Ligands of formula IC (and the precursors thereof) are also well-known in the art and can be readily prepared using art-recognized starting materials, reagents and reaction conditions. By way of illustration, compounds, intermediates and procedures useful in the preparation of ligands of formula IC or related compounds suitable for use as ligands in this invention are disclosed in the following patents and publications: U.S. Pat. No. 4,647,576, issued Mar. 3, 1987 to Hoefle et al.; U.S. Pat. No. 4,681,893, issued Jul. 21, 1987 to Roth; U.S. Pat. No. 5,055,484, issued Oct. 8, 1991; U.S. Pat. No. 5,128,366, issued Jul. 7, 1992 to Hirai et al.; U.S. Pat. No. 5,385,929, issued Jan. 31, 1995 to Bjorge et al.; U.S. Pat. No. 5,397,792, issued Mar. 14, 1995 to Butler et al.; U.S. Pat. No. 5,446,054, issued Aug. 29, 1995 to Butler et al.; B. D. Roth et al., *J. Med. Chem.*, 1991, 34, 357–366; K. L. Baumann et al., *Tetrahedron Lett.*, 1992, 33, 2283–2284; P. L. Brower et al., *Tetrahedron Lett.*, 1992, 33, 2279–2282. Each of these patents and publications is incorporated herein by reference in its entirety to the same extent as if each individual patent or publication was specifically and individually indicated to be incorporated by reference in its entirety.

A fourth group of preferred ligands for use in this invention are those ligands having formula ID:

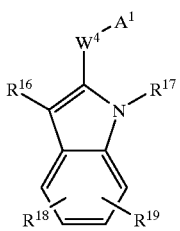

ID wherein $A^1$, $R^{16}$, $R^{17}$, $R^{18}$, $R^{19}$ and $W^4$ are as defined herein. Such ligands include, but are not limited to, derivatives of fluvastatin and the like.

Ligands of formula ID (and the precursors thereof) are also well-known in the art and can be readily prepared using art-recognized starting materials, reagents and reaction conditions. For example, compounds, intermediates and procedures useful in the preparation of ligands of formula ID or related compounds suitable for use as ligands in this invention are disclosed in the following patents and publications: U.S. Pat. No. 4,739,073, issued Apr. 19, 1988 to Kathawala; U.S. Pat. No. 5,118,853, issued Jun. 2, 1992 to Lee et al.; U.S. Pat. No. 5,164,400, issued Nov. 17, 1992 to Matsuo et al.; U.S. Pat. No. 5,290,946; issued Mar. 1, 1994 to Lee et al.; and U.S. Pat. No. 5,354,772, issued Oct. 11, 1994 to Kathawala. Each of these patents is incorporated herein by reference in its entirety to the same extent as if each individual patent or publication was specifically and individually indicated to be incorporated by reference in its entirety.

In addition to the ligands of formula IA–D, other ligands and intermediates thereof suitable for use in this invention are disclosed in U.S. Pat. No. 4,308,378, issued Dec. 29, 1981 to Stokker; U.S. Pat. No. 4,322,563, issued Mar. 30, 1982 to Hoffman; U.S. Pat. No. 4,567,289, issued Jan. 28, 1986 to Willard, et al.; U.S. Pat. No. 4,622,338, issued Nov. 11, 1986 to Baran et al.; U.S. Pat. No. 4,645,858, issued Feb. 24, 1987 to Lowrie, et al.; U.S. Pat. No. 4,654,363, issued Mar. 31, 1987 to Prugh; U.S. Pat. No. 4,772,626, issued Sep. 20, 1988 to Smith et al.; U.S. Pat. No. 4,782,084, issued Nov. 1, 1988 to Vyas et al.; U.S. Pat. No. 4,789,682, issued Dec. 6, 1988 to Stokker; U.S. Pat. No. 4,792,614, issued Dec. 20, 1988 to Fobare et al.; U.S. Pat. No. 4,855,321, issued Aug. 8, 1989 to Smith et al.; U.S. Pat. No. 4,863,957, issued Sep. 5, 1989 to Neuenschwander et al.;U.S. 4,892, 884, issued Jan. 9, 1990 to Neuenschwander et al.; U.S. Pat. No. 4,895,973, issued Jan. 23, 1990 to Baran et al.; U.S. Pat. No. 4,897,490, issued Jan. 30, 1990 to Sit et al.; U.S. Pat. No. 4,898,868, issued Feb. 6, 1990 to Bergmann et al.; U.S. Pat. No. 4,898,949, issued Feb. 6, 1990 to Wright et al.; U.S. Pat. No. 4,898,950, issued Feb. 6, 1990 to Han et al.; U.S. Pat. No. 4,900,754, issued Feb. 13, 1990 to Regan et al.; U.S. Pat. No. 4,904,646, issued Feb. 27, 1990 to Karanewsky, et al.; U.S. Pat. No. 4,904,691, issued Feb. 27, 1990 to Neuenschwander et al.; U.S. Pat. No. 4,904,692, issued Feb. 27, 1990 to Regan et al.; U.S. Pat. No. 4,914, 127, issued Apr. 3, 1990 to Beck et al.; U.S. Pat. No. 4,925,852, issued May 15, 1990 to Kesseler et al.; U.S. Pat. No. 4,939,143, issued Jul. 3, 1990 to Regan et al.; U.S. Pat. No. 4,940,800, issued Jul. 10, 1990 to Bertolini et al.; U.S. Pat. No. 4,946,841, issued Aug. 7, 1990 to Baader et al.; U.S. Pat. No. 4,946,852, issued Aug. 7, 1990 to Jendralla et al.; U.S. Pat. No. 4,946,860, issued Aug. 7, 1990 to Morris, et al.; U.S. Pat. No. 4,965,373, issued Oct. 23, 1990 to Baran et al.; U.S. Pat. No. 4,970,077, issued Nov. 13, 1990 to Dreclkmann et al.; U.S. Pat. No. 4,970,221, issued Nov. 13, 1990 to Magnin et al.; U.S. Pat. No. 4,992,429, issued Feb. 12, 1991 to Ullrich et al.; U.S. Pat. No. 4,994,494, issued Feb. 19, 1991 to Regan et al.; U.S. Pat. No. 4,996,234, issued Feb. 26, 1991 to Regan et al.; U.S. Pat. No. 4,499, 289, issued Feb. 12, 1985 to Baran et al.; U.S. Pat. No. 5,001,128, issued Mar. 19, 1991 to Neuenschwander et al.; U.S. Pat. No. 5,001,144, issued Mar. 19, 1991 to Regan et al.; U.S. Pat. No. 5,010,205, issued Apr. 23, 1991 to Sit et al.; U.S. Pat. No. 5,013,749, issued May 7, 1991 to Watson, et al.; U.S. Pat. No. 5,017,716, issued May 21, 1991 to Karanewsky et al.; U.S. Pat. No. 5,025,017, issued Jun. 18, 1991 to Karanewsky; U.S. Pat. No. 5,041,694, issued Aug. 20, 1991 to Baran et al.; U.S. Pat. No. 5,049,577, issued Sep. 17, 1991 to Varma et al.; U.S. Pat. No. 5,049, issued Sep. 17, 1991 to Varma et al.; U.S. Pat. No. 5,081,136, issued Jan. 14, 1992 to Bertolini, et al.; U.S. Pat. No. 5,082,859, issued Jan. 21, 1992 to Festal et al.; U.S. Pat. No. 5,091,378, issued Feb. 25, 1992 to Karanewsky et al.; U.S. Pat. No. 5,091,386, issued Feb. 25, 1992 to Kesseler et al.; U.S. Pat. No. 5,106,992, issued Apr. 21, 1992 to Magnin et al.; U.S. Pat. No. 5,110,825, issued May 5, 1992 to Ogata et al.; U.S. Pat. No. 5,110,940, issued May 5, 1992 to Sit et al.; U.S. Pat. No. 5,112,819, issued May 12, 1992 to Ross et al.; U.S. Pat. No. 5,114,964, issued May 19, 1992 to Barton; U.S. Pat. No. 5,120,782, issued Jun. 9, 1992 to Hubsch et al.; U.S. Pat. No. 5,120,848, issued Jun. 9, 1992 to Watson et al.; U.S. Pat. No. 5,132,312, issued Jul. 21, 1992 to Regan et al.; U.S. Pat. No. 5,137,881, issued Aug. 11, 1992 to Hubsch et al.; U.S. Pat. No. 5,157,134, issued Oct. 20, 1992 to Karanewsky; U.S. Pat. No. 5,166,171, issued Nov. 24, 1992 to Jendralla et al.; U.S. Pat. No. 5,183,924, issued Feb. 2, 1993 to Festal et al.; U.S. Pat. No. 5,194,634, issued Mar. 16, 1993 to Karanewsky; U.S. Pat. No. 5,196,440, issued Mar. 23, 1993 to Bertolini et al.; U.S. Pat. No. 5,202,327, issued Apr. 13, 1993 to Robl; U.S. Pat. No. 5,248,830, issued Sep. 28, 1983 to Ullrich et al.; U.S. Pat. No. 5,250,561, issued Oct. 5, 1993 to Connolly et al.; U.S. Pat. No. 5,256,692, issued Oct. 26, 1993 to Gordon et al.; U.S. Pat. No. 5,260,440, issued Nov. 9, 1993 to Hirai et al.; U.S. Pat. No. 5,276,021, issued Jan. 4, 1994 to Karanewsky et al.; U.S. Pat. No. 5,369,109, issued Nov. 29, 1994 to Hiyama et al.; U.S. Pat. No. 5,523,460, issued Jun. 4, 1996 to Matsumoto et al.; EP 0 216 127 A2, published Apr. 1, 1987 to Wess et al.; EP 0 344 602 A1, published Dec. 6, 1989 to Dreckmann et al.; EP 0 355 846 A2, published Feb. 28, 1990 to Sit et al.; EP 0 435 322 A2, published July 3, 1991 to Ogata et al.; G. Beck et al., *J. Med. Chem.*, 1990, 33, 52–60; C. Chan et al., *J. Med. Chem.*, 1993, 36, 3646–3657; C. Taillefumier et al., *Bioorganic & Medicinal Chem. Let.*; 1996, 6, 615–618. Each of these patents and publications is incorporated herein by reference in its entirety to the same extent as if each individual patent or publication was specifically and individually indicated to be incorporated by reference in its entirety.

Additionally, the following patents and publications disclosed processes or intermediates which may be useful in this invention: U.S. Pat. No. 4,440,927, issued Apr. 3, 1984 to Prugh; U.S. Pat. No. 4,474,971, issued Oct. 2, 1984 to Wareing; U.S. Pat. No. 4,582,914, issued Apr. 15, 1986 to Volante et al.; U.S. Pat. No. 4,582,915, issued Apr. 15, 1986 to Sleteinger et al.; U.S. Pat. No. 4,588,820, issued May 13, 1986 to Stokker; U.S. Pat. No. 4,611,067, issued Sep. 9, 1986 to Volante et al.; U.S. Pat. No. 4,611,068, issued Sep. 9, 1986 to Guindon et al.; U.S. Pat. No. 4,611,081, issued Sep. 9, 1986 to Lynch et al.; U.S. Pat. No. 4,645,854, issued Feb. 24, 1987 to Verhoeven et al.; U.S. Pat. No. 5,650,523, issued Jul. 22, 1997 to DeCamp et al.; U.S. Pat. No. 4,683,314, issued Jul. 28, 1987 to Prugh; U.S. Pat. No. 5,072,023, issued Dec. 10, 1991 to Robl; U.S. Pat. No. 5,149,835, issued Sep. 22, 1992 to Morrow et al.; U.S. Pat. No. 5,258,544, issued Nov. 2, 1993 to Reilly, Jr. et al.; U.S. Pat. No. 5,274,155, issued Dec. 28, 1993 to Thottathil et al.; U.S. Pat. No. 5,278,313, issued Jan. 11, 1994 to Thottathil et al.; U.S. Pat. No. 5,286,883, issued Feb. 15, 1994 to Sakurai et al.; U.S. Pat. No. 5,298,625, issued Mar. 29, 1994 to Thottathil et al.; U.S. Pat. No. 5,349,069, issued Sep. 20, 1994 to Thottathil et al.; U.S. Pat. No. 5,354,879, issued Oct. 11, 1994 to Konoike et al.; U.S. Pat. No. 5,481,009, issued Jan. 2, 1996 to Matsumoto et al.; U.S. Pat. No. 5,449,793, issued Sep. 12, 1995 to Miyazawa et al.; U.S. Pat. No. 5,594,153, issued Jan. 14, 1997 to Thottathil et al.; U.S. Pat. No. 5,599,952, issued Feb. 4, 1997 to Matsumoto et al.; U.S. Pat. No. 5,599,954, issued Feb. 4, 1997 to Mitsuhashi et al. Each of these patents or publications is incorporated herein by reference in its entirety to the same extent as if each individual patent or publication was specifically and individually indicated to be incorporated by reference in its entirety.

Figure 14:
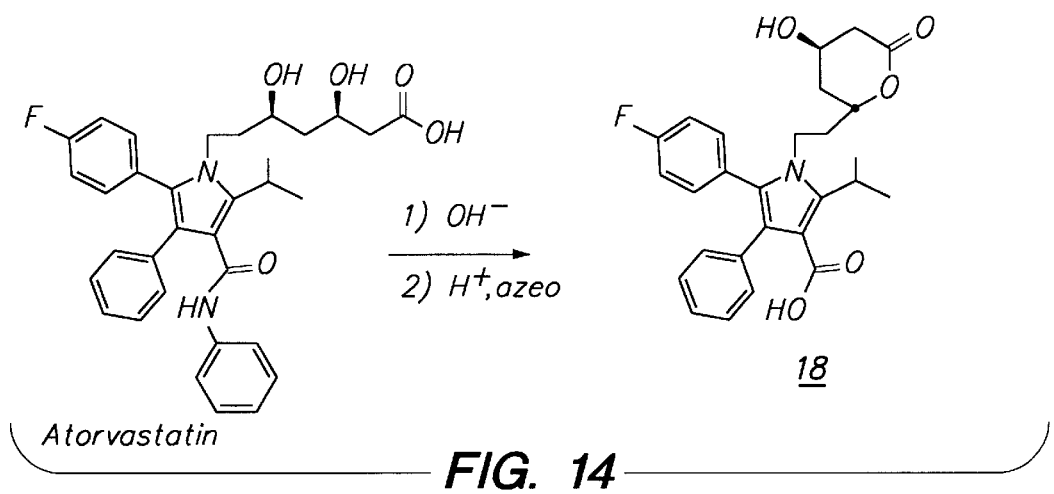
FIG. 14 illustrates a representative synthesis of a ligand precursor having a carboxyl attachment site.
Figure 11:
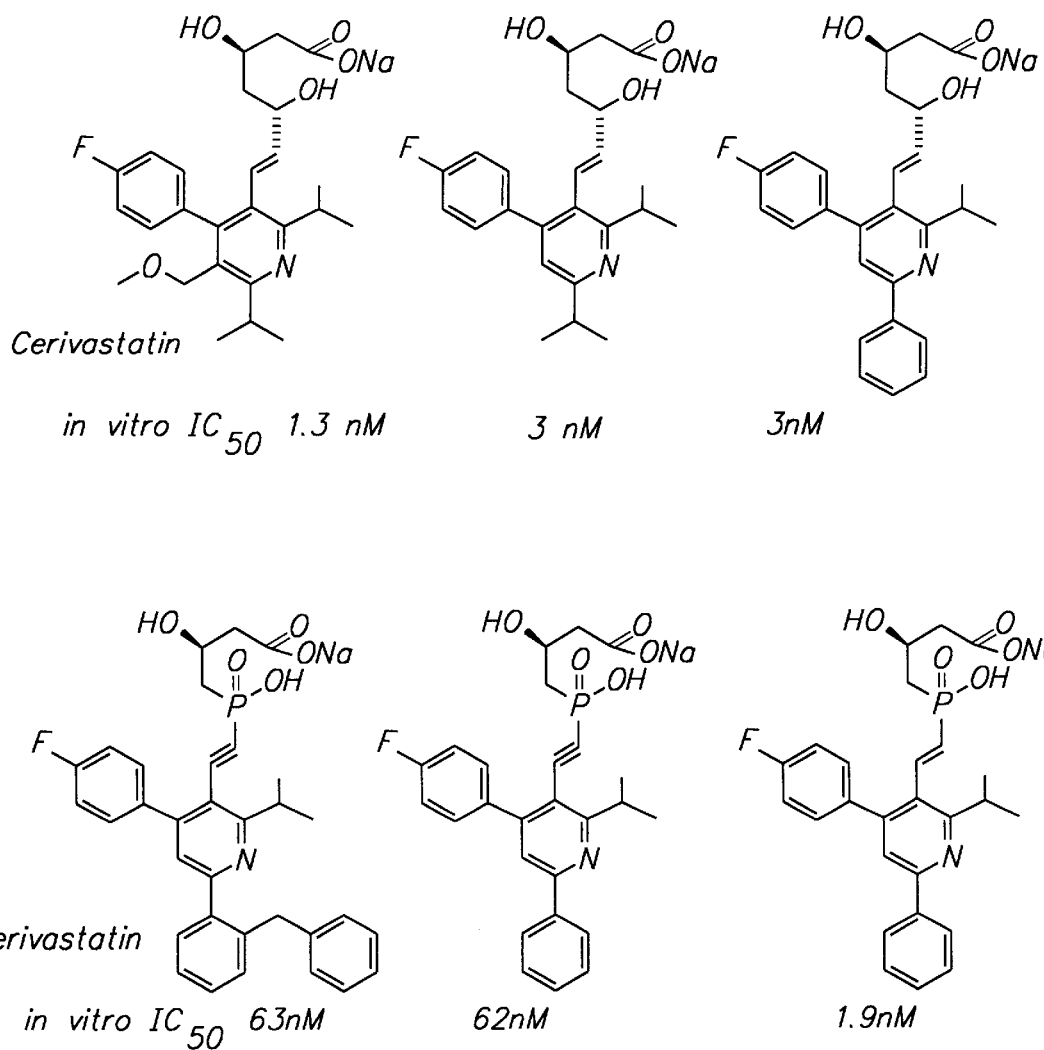
FIG. 11 shows various cerivastatin analogs having bulky substitutents in the "southern" binding domain and their in vitro activity.
Figure 12:
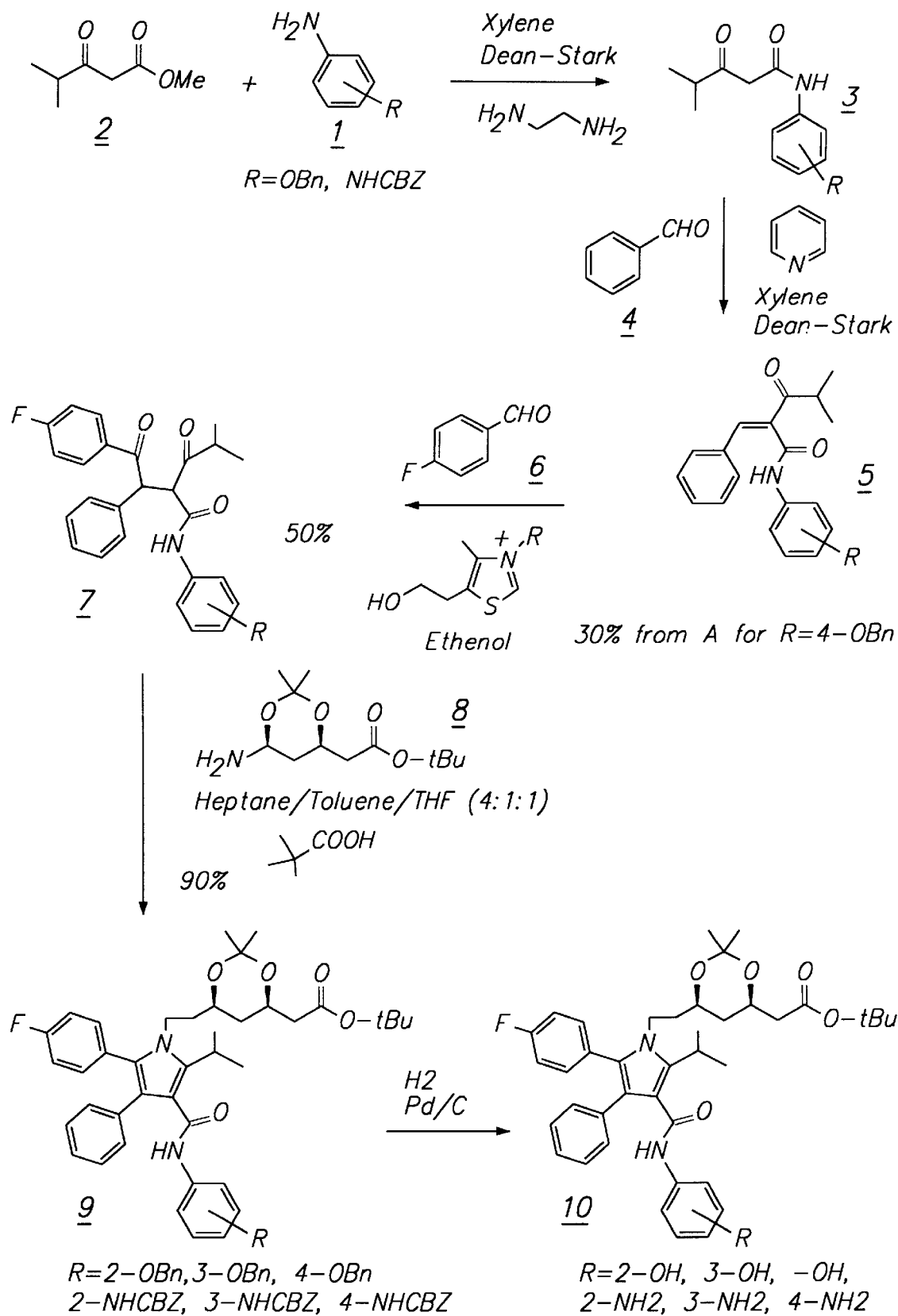
FIGS. 12 and 13 illustrate representative syntheses of ligand precursors having an amino or hydroxyl attachment site.
Figure 13:
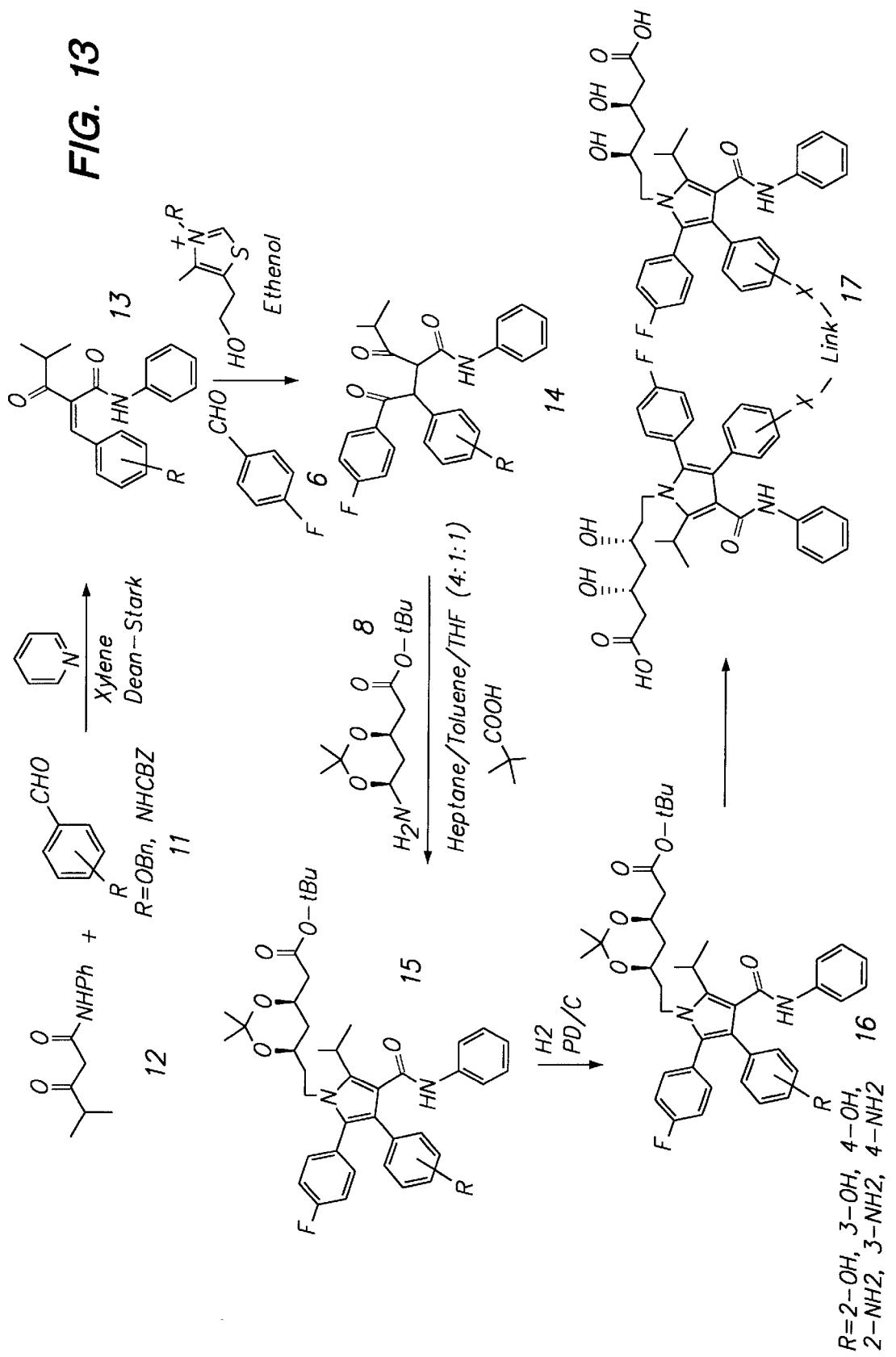

Representative syntheses of ligand precursors are illustrated in FIGS. 12–14. It will be understood by those skilled in the art that the following methods may be used to prepare other multibinding compounds of this invention. FIG. 12 illustrates the synthesis of ligand precursors having an amino or hydroxyl attachment site. As shown in FIG. 12, a substituted phenyl amine, 1, having a protected amino or hydroxyl group is first reacted with methyl isobutyryl acetate, 2, in the presence of 1,2-ethylene diamine to form the corresponding amide, 3. This reaction is typically conducted for about 16 hours in refluxing xylenes. Amide 3 is typically not isolated, but is reacted in situ with benzaldehyde, 4, to provide the keto amide intermediate 5. This reaction is typically conducted in refluxing xylenes, again using a Dean-Stark trap to remove the water produced during the condensation reaction. The condensation product 5 is typically isolated using conventional techniques, such as recrystallization or chromatography.

Intermediate 5 is then reacted with 4-fluorobenzaldehyde, 6, in ethanol in the presence of triethylamine and a catalytic amount of 3-ethyl-5-(2-hydroxyethyl)-4-methylthiazolium bromide to afford diketone amide intermediate 7. This reaction is typically conducted at about 90° C. for about 12 hours. The diketone amide intermediate 7 is then readily condensed with (4R-cis)-1,1-dimethylethyl-6-(2-aminoethyl)-2,2-dimethyl-1,3-dioxane-4-acetate, 8, (prepared as described in U.S. Pat. No. 5,216,174 and EPO 330172A2, which references are incorporated herein by reference in their entirety) to provide pyrrole 9. This reaction is typically conducted by heating the 7 and 8 in the presence of pivalic acid in an inert diluent comprising heptane/ toluene/tetrahydrofurnan (4:1:1, v/v/v) for about 48 hours. These reaction are described in more detail in U.S. Pat. No. 5,385,929 and Tet. Lett. 1992, 33, 2279, the disclosures of which are incorporated herein by reference in their entirety.

The protecting group is then removed from pyrrole 9 using conventional de-blocking reagents and conditions to afford ligand precursor 10. For example, a benzyl protecting group (Bn) can be removed from a blocked hydroxyl group by hydrogenolysis in the presence of a catalysis, such as palladium on carbon. Similar conditions are employed to remove a benzyloxycarbonyl protecting group (CBZ) from a blocked amino group to form the free amine.

FIG. 13 illustrates an alternative synthesis which provides a ligand precursor having an amino or hydroxyl attachment site at a different position of the ligand precursor. As shown in FIG. 13, a substituted benzaldehyde, 11, is first condensed with amide 12 to afford keto amide 13. Subsequent condensation with 4-fluorobenzaldehyde, 6, affords 14, which is then condensed with amine 8 to provide pyrrole 15. Deprotection of 15 under standard conditions then affords ligand precursor 16. The conditions for these reactions are essentially the same as those described above.

By way of further illustration, FIG. 14 shows the facile synthesis of a ligand precursor having a carboxyl attachment site by hydrolysis of the N-phenyl amide moiety of atorvastatin, followed by acidification to form the corresponding lactone 18. This reaction is typically conducted by reacting atorvastatin (prepared, for example, by the procedures described in U.S. Pat. Nos. 5,397,792 and 5,446,054, the disclosures of which are incorporated herein by reference in their entirety) with an excess of an alkali or alkaline earth metal hydroxide, such as sodium or lithium hydroxide, in an inert diluent, such as ethanol. After completion of the hydrolysis reaction, the hydrolysis product is acidified to form the corresponding lactone 18.

Figure 15:
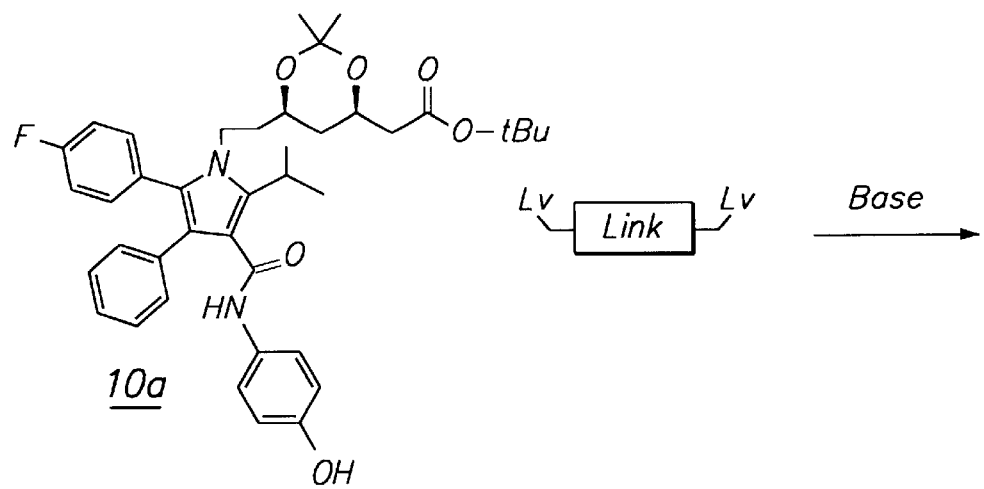
FIG. 15 illustrates dimer formation by alkylation of a hydroxyl-containing intermediate with a bis-electrophile.
Figure 15:
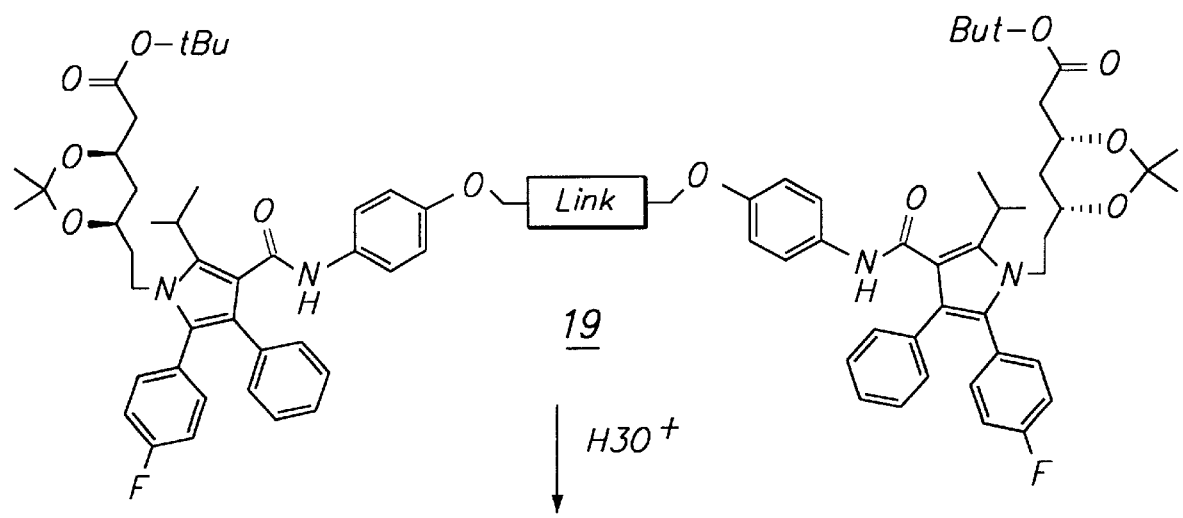
Figure 15:
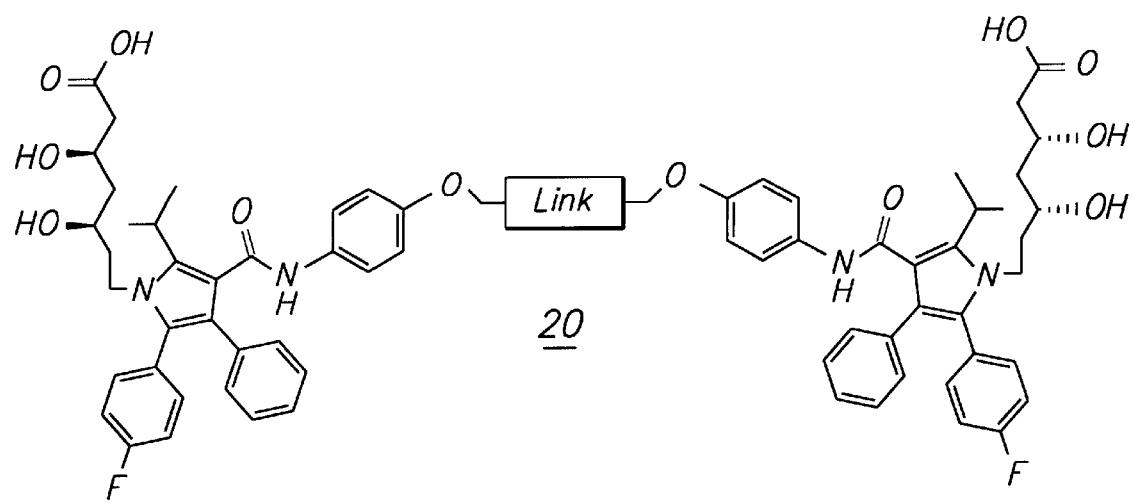

The ligand precursors prepared as described above can then be covalently linked to a linker using conventional reagents and conditions. For example, two equivalents of ligand precursor 10a, i.e., wherein R is a 4-hydroxy group, can be readily coupled to a linker precursor to form a dimer as illustrated in FIG. 15. As shown in FIG. 15, ligand precursor 10a is reacted with a linker precursor having at least two leaving groups (i.e., as shown in FIG. 15 where "Lv" is a leaving group and "Link" is the non-reactive portion of the linker precursor) in the presence of base to form protected dimer 19. The leaving group employed in this reaction may be any conventional leaving group including, by way of example, a halogen such as chloro, bromo or iodo, or a sulfonate group such as tosyl, mesyl and the like. Any base which effectively deprotonates the phenolic hydroxyl group may be used in this reaction including, by way of illustration, potassium carbonate, sodium hydride, sodium hydroxide and the like. Subsequent deblocking of protected dimer 19 under standard conditions affords dimer 20.

Figure 16:
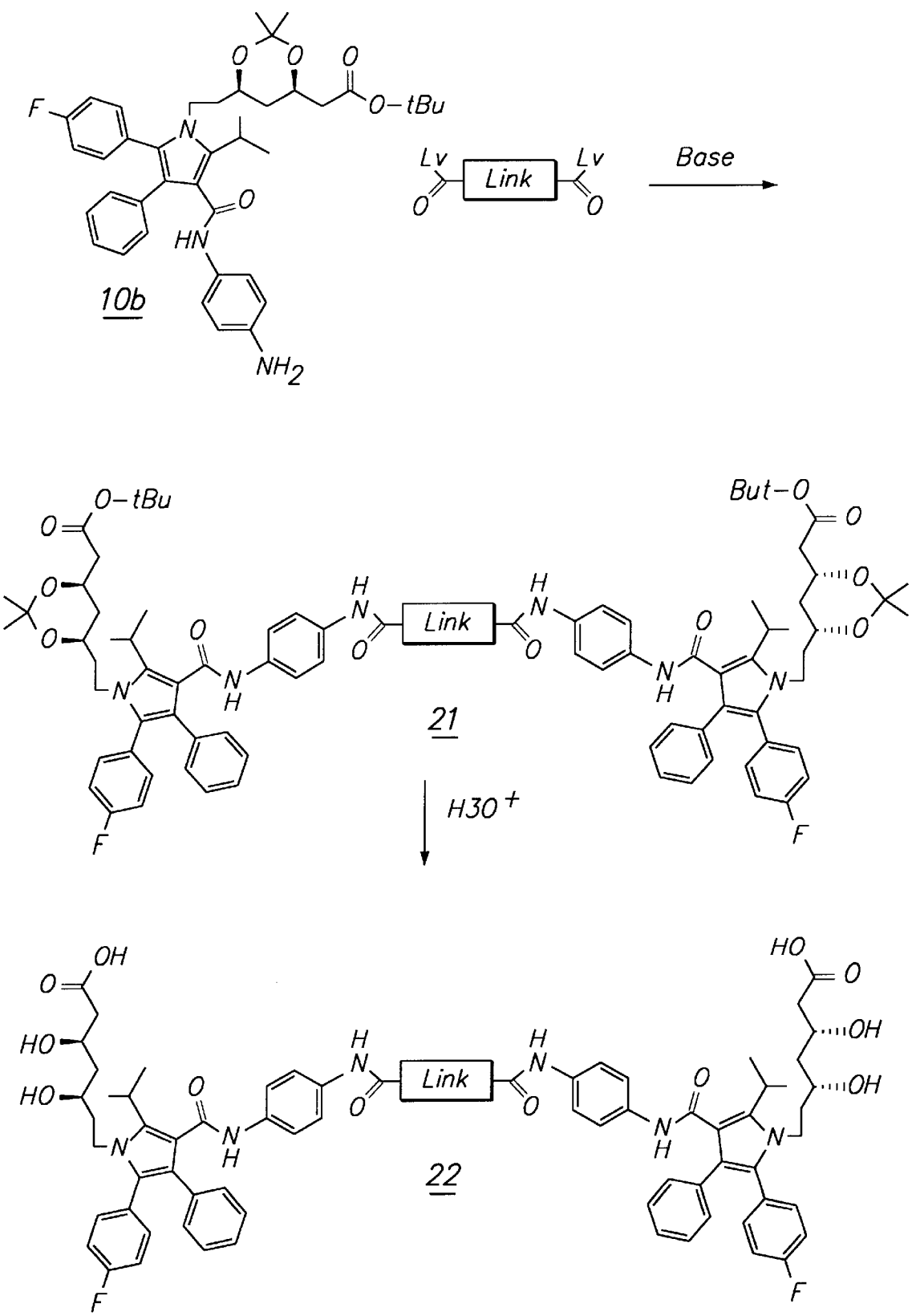
FIG. 16 illustrates dimer formation by acylation of an amino-containing intermediate with a bis-electrophile.

Similarly, two equivalents of ligand precursor 10b, i.e., wherein R is a 4-amino group, can be readily coupled to a linker precursor to form a dimer as illustrated in FIG. 16. As shown in FIG. 16, ligand precursor SOb is reacted with a linker precursor having at least two acylating groups (—C (O)Lv) to form protected dimer 21. Linker precursors containing any conventional acylating groups may be employed in this reaction including, by way of illustration, linker precursors having acyl halide groups such as acyl chorides or acyl bromides, or anhydrides.

When an acyl halide is employed in this reaction, amine 10b is typically reacted with the acyl halide in the presence of a suitable base to scavenge the acid generated during the reaction. Suitable bases include, by way of example, triethylamine, diisopropylethylamine, N-methylmorpholine and the like.

Alternatively, a linker precursor having at least two carboxylic acid groups may be employed in this reaction. When amine 10b is coupled to a linker precursor having carboxylic acid groups, a conventional peptide coupling reagent is employed using conventional coupling reaction conditions, typically in the presence of a trialkylamine, such as ethyldiisopropylamine. Suitable coupling reagents for use in this reaction include, by way of example, carbodiimides, such as ethyl-3-(3-dimethylamino)propylcarboiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris(dimethylatnino)phosphonium hexafluorophosphate (BOP) and the like. Optionally, well-known coupling promoters, such N-hydroxysuccinimide, 1-hydroxybenzotriazole and the like, may be employed in this reaction. Typically, this coupling reaction is conducted at a temperature ranging from about 0° C. to about 60° C. for about 1 to about 72 hours in an inert diluent, such as THF, to afford the protected intermediate 21. Subsequent deblocking of protected dimer 21 using standard reagents and conditions then affords dimer 22.

Figure 17:
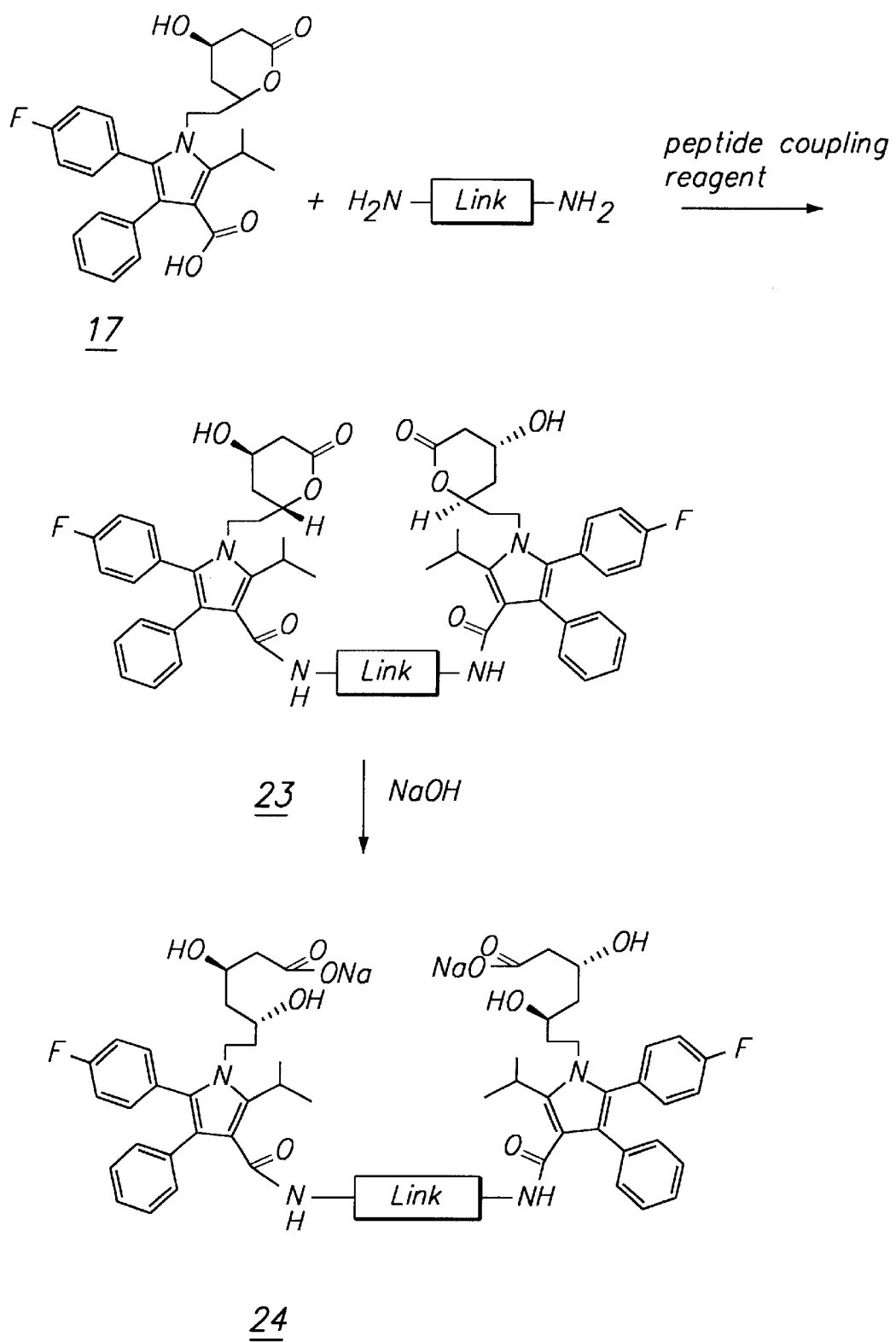
FIG. 17 illustrates dimer formation by reaction of a carboxyl-containing intermediate with a bis-amine.

In a similar manner, ligand precursor 17 can be coupled to a bis-amine as shown in FIG. 17 to afford dimer 23. Optionally, the lactone ring of dimer 23 can be hydrolyzed using conventional reagents and conditions to provide dimer 24.

As will be readily apparent to those of ordinary skill in the art, the synthetic procedures described herein or those known in the art may be readily modified to afford a wide variety of compounds within the scope of this invention.

Combinatorial Libraries

The methods described herein lend themselves to combinatorial approaches for identifying multimeric compounds which possess multibinding properties.

Specifically, factors such as the proper juxtaposition of the individual ligands of a multibinding compound with respect to the relevant array of binding sites on a target or targets is important in optimizing the interaction of the multibinding compound with its target(s) and to maximize the biological advantage through multivalency. One approach is to identify a library of candidate multibinding compounds with properties spanning the multibinding parameters that are relevant for a particular target. These parameters include: (1) the identity of ligand(s), (2) the orientation of ligands, (3) the valency of the construct, (4) linker length, (5) linker geometry, (6) linker physical properties, and (7) linker chemical functional groups.

Libraries of multimeric compounds potentially possessing multibinding properties (i.e., candidate multibinding compounds) and comprising a multiplicity of such variables are prepared and these libraries are then evaluated via conventional assays corresponding to the ligand selected and the multibinding parameters desired. Considerations relevant to each of these variables are set forth below:

Selection of Ligand(s)

A single ligand or set of ligands is (are) selected for incorporation into the libraries of candidate multibinding compounds which library is directed against a particular biological target or targets, i.e., inhibition of HMG-CoA reductase. The only requirement for the ligands chosen is that they are capable of interacting with the selected target (s). Thus, ligands may be known drugs, modified forms of known drugs, substructures of known drugs or substrates of modified forms of known drugs (which are competent to interact with the target), or other compounds. Ligands are preferably chosen based on known favorable properties that may be projected to be carried over to or amplified in multibinding forms. Favorable properties include demonstrated safety and efficacy in human patients, appropriate PK/ADME profiles, synthetic accessibility, and desirable physical properties such as solubility, logP, etc. However, it is crucial to note that ligands which display an unfavorable property from among the previous list may obtain a more favorable property through the process of multibinding compound formation; i.e., ligands should not necessarily be excluded on such a basis. For example, a ligand that is not sufficiently potent at a particular target so as to be efficacious in a human patient may become highly potent and efficacious when presented in multibinding form. A ligand that is potent and efficacious but not of utility because of a non-mechanism-related toxic side effect may have increased therapeutic index (increased potency relative to toxicity) as a multibinding compound. Compounds that exhibit short in vivo half-lives may have extended half-lives as multibinding compounds. Physical properties of ligands that limit their usefulness (e.g. poor bioavailability due to low solubility, hydrophobicity, hydrophilicity) may be rationally modulated in multibinding forms, providing compounds with physical properties consistent with the desired utility.

Orientation: Selection of Ligand Attachment Points and Linking Chemistry

Several points are chosen on each ligand at which to attach the ligand to the linker. The selected points on the ligand/linker for attachment are functionalized to contain complementary reactive functional groups. This permits probing the effects of presenting the ligands to their target binding site(s) in multiple relative orientations, an important multibinding design parameter. The only requirement for choosing attachment points is that attaching to at least one of these points does not abrogate activity of the ligand. Such points for attachment can be identified by structural information when available. For example, inspection of a co-crystal structure of a ligand bound to its target allows one to identify one or more sites where linker attachment will not preclude the ligand/target interaction. Alternatively, evaluation of ligand/target binding by nuclear magnetic resonance will permit the identification of sites non-essential for ligand/target binding. See, for example, Fesik, et al., U.S. Pat. No. 5,891,643, the disclosure of which is incorporated herein by reference in its entirety. When such structural information is not available, utilization of structure-activity relationships (SAR) for ligands will suggest positions where substantial structural variations are and are not allowed. In the absence of both structural and SAR information, a library is merely selected with multiple points of attachment to allow presentation of the ligand in multiple distinct orientations. Subsequent evaluation of this library will indicate what positions are suitable for attachment.

It is important to emphasize that positions of attachment that do abrogate the activity of the monomeric ligand may also be advantageously included in candidate multibinding compounds in the library provided that such compounds bear at least one ligand attached in a manner which does not abrogate intrinsic activity. This selection derives from, for example, heterobivalent interactions within the context of a single target molecule. For example, consider a ligand bound to its target, and then consider modifying this ligand by attaching to it a second copy of the same ligand with a linker which allows the second ligand to interact with the same target at sites proximal to the first binding site, which include elements of the target that are not part of the formal ligand binding site and/or elements of the matrix surrounding the formal binding site, such as the membrane. Here, the most favorable orientation for interaction of the second ligand molecule may be achieved by attaching it to the linker at a position which abrogates activity of the ligand at the first binding site. Another way to consider this is that the SAR of individual ligands within the context of a multibinding structure is often different from the SAR of those same ligands in momomeric form.

The foregoing discussion focused on bivalent interactions of dimeric compounds bearing two copies of the same ligand joined to a single linker through different attachment points, one of which may abrogate the binding/activity of the monomeric ligand. It should also be understood that bivalent advantage may also be attained with heterodimeric constructs bearing two different ligands that bind to common or different targets.

Once the ligand attachment points have been chosen, one identifies the types of chemical linkages that are possible at those points. The most preferred types of chemical linkages are those that are compatible with the overall structure of the ligand (or protected forms of the ligand) readily and generally formed, stable and intrinsically innocuous under typical chemical and physiological conditions, and compatible with a large number of available linkers. Amide bonds, ethers, amines, carbamates, ureas, and sulfonamides are but a few examples of preferred linkages.

Linker Selection

In the library of linkers employed to generate the library of candidate multibinding compounds, the selection of linkers employed in this library of linkers takes into consideration the following factors:

Valency: In most instances the library of linkers is initiated with divalent linkers. The choice of ligands and proper juxtaposition of two ligands relative to their binding sites permits such molecules to exhibit target binding affinities and specificities more than sufficient to confer biological advantage. Furthermore, divalent linkers or constructs are also typically of modest size such that they retain the desirable biodistribution properties of small molecules.

Linker Length: Linkers are chosen in a range of lengths to allow the spanning of a range of inter-ligand distances that encompass the distance preferable for a given divalent interaction. In some instances the preferred distance can be estimated rather precisely from high-resolution structural information of targets. In other instances where high-resolution structural information is not available, one can make use of simple models to estimate the maximum distance between binding sites either on adjacent receptors or at different locations on the same receptor. In situations where two binding sites are present on the same target (or target subunit for multisubunit targets), preferred linker distances are 10–100 Å, with more preferred linker distances of 50–100 Å. In situations where two binding sites reside on separate target sites, preferred linker distances are 50–100 Å, with more preferred distances of 60–100 Å.

Linker Geometry and Rigidity: The combination of ligand attachment site, linker length, linker geometry, and linker rigidity determine the possible ways in which the ligands of candidate multibinding compounds may be displayed in three dimensions and thereby presented to their binding sites. Linker geometry and rigidity are nominally determined by chemical composition and bonding pattern, which may be controlled and are systematically varied as another spanning function in a multibinding array. For example, linker geometry is varied by attaching two ligands to the ortho, meta, and para positions of a benzene ring, or in cis- or trans-arrangements at the 1,1- vs. 1,2- vs. 1,3- vs. 1,4-positions around a cyclohexane core or in cis- or trans-arrangements at a point of ethylene unsaturation. Linker rigidity is varied by controlling the number and relative energies of different conformational states possible for the linker. For example, a divalent compound bearing two ligands joined by 1,8-octyl linker has many more degrees of freedom, and is therefore less rigid than a compound in which the two ligands are attached to the 4,4' positions of a biphenyl linker.

Linker Physical Properties: The physical properties of linkers are nominally determined by the chemical constitution and bonding patterns of the linker, and linker physical properties impact the overall physical properties of the candidate multibinding compounds in which they are included. A range of linker compositions is typically selected to provide a range of physical properties (hydrophobicity, hydrophilicity, amphiphilicity, polarization, acidity, and basicity) in the candidate multibinding compounds. The particular choice of linker physical properties is made within the context of the physical properties of the ligands they join and preferably the goal is to generate molecules with favorable PK/ADME properties. For example, linkers can be selected to avoid those that are too hydrophilic or too hydrophobic to be readily absorbed and/or distributed in vivo.

Linker Chemical Functional Groups: Linker chemical functional groups are selected to be compatible with the chemistry chosen to connect linkers to the ligands and to impart the range of physical properties sufficient to span initial examination of this parameter.

Combinatorial Synthesis

Having chosen a set of n ligands (n being determined by the sum of the number of different attachment points for each ligand chosen) and m linkers by the process outlined above, a library of (n!)m candidate divalent multibinding compounds is prepared which spans the relevant multibinding design parameters for a particular target. For example, an array generated from two ligands, one which has two attachment points (A1, A2) and one which has three attachment points (B1, B2, B3) joined in all possible combinations provide for at least 15 possible combinations of multibinding compounds:

A1-A1 A1-A2 A1-B1 A1-B2 A1-B3 A2-A2 A2-B1 A2-B2 A2-B3 B1-B1 B1-B2 B1-B3 B2-B2 B2-B3 B3-B3

When each of these combinations is joined by 10 different linkers, a library of 150 candidate multibinding compounds results.

Given the combinatorial nature of the library, common chemistries are preferably used to join the reactive functionaries on the ligands with complementary reactive functionalities on the linkers. The library therefore lends itself to efficient parallel synthetic methods. The combinatorial library can employ solid phase chemistries well known in the art wherein the ligand and/or linker is attached to a solid support. Alternatively and preferably, the combinatorial libary is prepared in the solution phase. After synthesis, candidate multibinding compounds are optionally purified before assaying for activity by, for example, chromatographic methods (e.g., HPLC).

Analysis of the Library

Various methods are used to characterize the properties and activities of the candidate multibinding compounds in the library to determine which compounds possess multibinding properties. Physical constants such as solubility under various solvent conditions and logD/clogD values are determined. A combination of NMR spectroscopy and computational methods is used to determine low-energy conformations of the candidate multibinding compounds in fluid media. The ability of the members of the library to bind to the desired target and other targets is determined by various standard methods, which include radioligand displacement assays for receptor and ion channel targets, and kinetic inhibition analysis for many enzyme targets. In vitro efficacy, such as for receptor agonists and antagonists, ion channel blockers, and antimicrobial activity, are also determined. Pharmacological data, including oral absorption, everted gut penetration, other pharmacokinetic parameters and efficacy data are determined in appropriate models. In this way, key structure-activity relationships are obtained for multibinding design parameters which are then used to direct future work.

The members of the library which exhibit multibinding properties, as defined herein, can be readily determined by conventional methods. First those members which exhibit multibinding properties are identified by conventional methods as described above including conventional assays (both in vitro and in vivo).

Second, ascertaining the structure of those compounds which exhibit multibinding properties can be accomplished via art recognized procedures. For example, each member of the library can be encrypted or tagged with appropriate information allowing determination of the structure of relevant members at a later time. See, for example, Dower, et al., International Patent Application Publication No. WO 93/06121; Brenner, et al., Proc. Natl. Acad. Sci., USA, 89:5181 (1992); Gallop, et al., U.S. Pat. No. 5,846,839; each of which are incorporated herein by reference in its entirety. Alternatively, the structure of relevant multivalent compounds can also be determined from soluble and untagged libaries of candidate multivalent compounds by methods known in the art such as those described by Hindsgaul, et al., Canadian Patent Application No. 2,240,325 which was published on Jul. 11, 1998. Such methods couple frontal affinity chromatography with mass spectroscopy to determine both the structure and relative binding affinities of candidate multibinding compounds to receptors.

The process set forth above for dimeric candidate multibinding compounds can, of course, be extended to trimeric candidate compounds and higher analogs thereof.

Follow-up Synthesis and Analysis of Additional Libraries

Based on the information obtained through analysis of the initial library, an optional component of the process is to ascertain one or more promising multibinding "lead" compounds as defined by particular relative ligand orientations, linker lengths, linker geometries, etc. Additional libraries can then be generated around these leads to provide for further information regarding structure to activity relationships. These arrays typically bear more focused variations in linker structure in an effort to further optimize target affinity and/or activity at the target (antagonism, partial agonism, etc.), and/or alter physical properties. By iterative redesign/analysis using the novel principles of multibinding design along with classical medicinal chemistry, biochemistry, and pharmacology approaches, one is able to prepare and identify optimal multibinding compounds that exhibit biological advantage towards their targets and as therapeutic agents.

To further elaborate upon this procedure, suitable divalent linkers include, by way of example only, those derived from dicarboxylic acids, disulfonylhalides, dialdehydes, diketones, dihalides, diisocyanates, diamines, diols, mixtures of carboxylic acids, sulfonylhalides, aldehydes, ketones, halides, isocyanates, amines and diols. In each case, the carboxylic acid, sulfonylhalide, aldehyde, ketone, halide, isocyanate, amine and diol functional group is reacted with a complementary functionality on the ligand to form a covalent linkage. Such complementary functionality is well known in the art as illustrated in the following table:

| Representative Complementary Binding Chemisties | | |
|---|---|---|
| First Reactive Group | Second Reactive Group | Linkage |
| hydroxyl | isocyanate | carbamate |
| amine | epoxide | β-hydroxyamine |
| sulfonyl halide | amine | sulfonamide |
| carboxyl acid | amine | amide |
| hydroxyl | alkyl/aryl halide | ether |
| aldehyde | amine(+reducing agent) | amine |
| ketone | amine(+reducing agent) | amine |
| amine | isocyanate | urea |

Exemplary linkers include the following linkers identified as X-1 through X-418 as set forth below:

Diacids

X-1

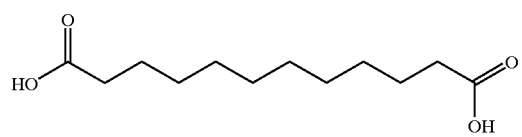

X-2

-continued
| Diacids | |
|---|---|
| 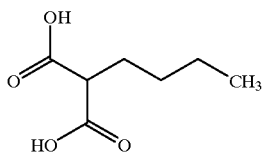 | X-3 |
| 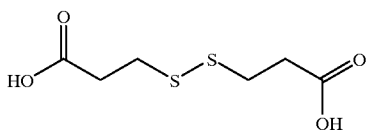 | X-4 |
| 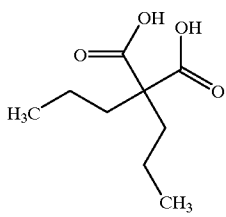 | X-5 |
| 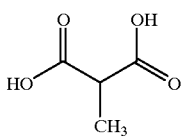 | X-6 |
| 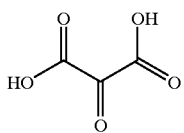 | X-7 |
| 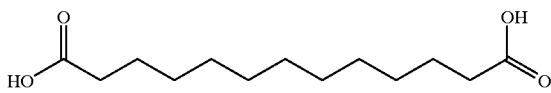 | X-8 |
| 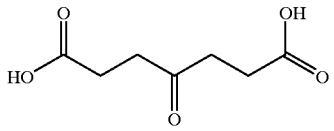 | X-9 |
| 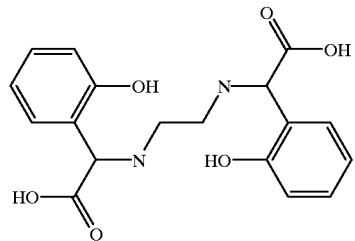 | X-10 |

-continued
| Diacids | |
|---|---|
| 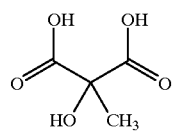 | X-11 |
| 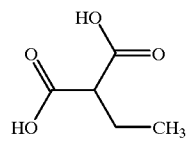 | X-12 |
| 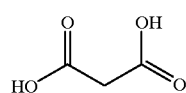 | X-13 |
| 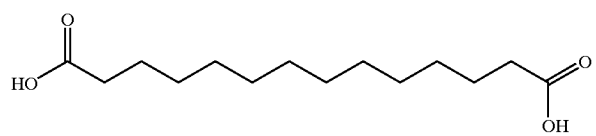 | X-14 |
| 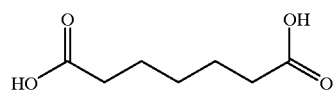 | X-15 |
| 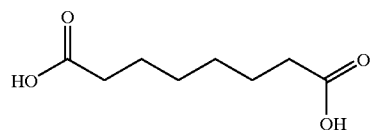 | X-16 |
| 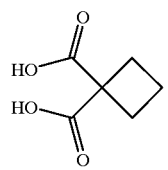 | X-17 |
| 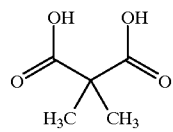 | X-18 |
| 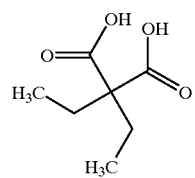 | X-19 |

-continued
Diacids
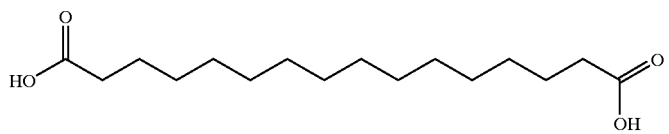
X-20
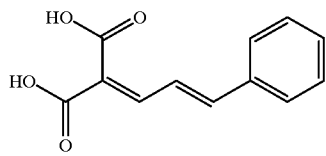
X-21
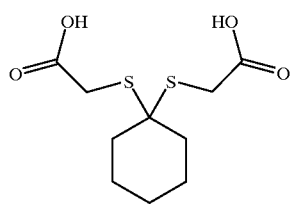
X-22
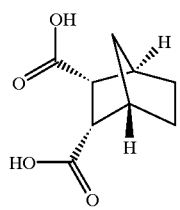
X-23
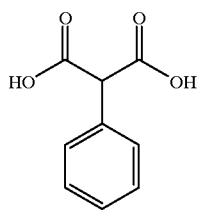
X-24
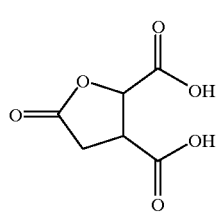
X-25
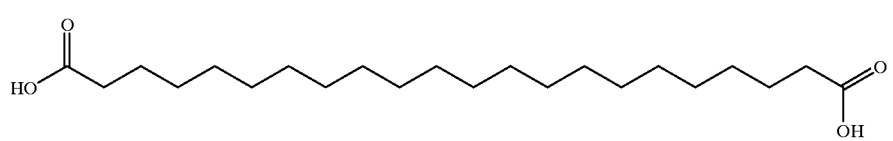
X-26

-continued
Diacids
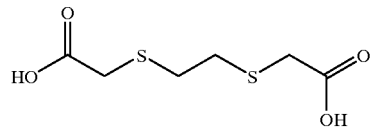
X-27
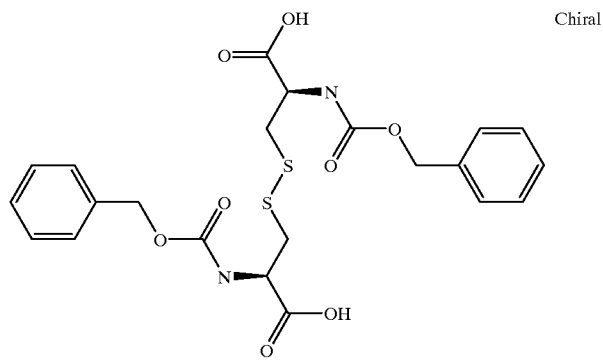
X-28
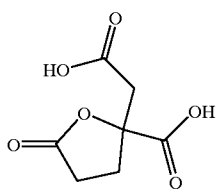
X-29
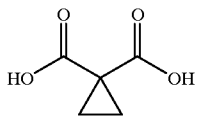
X-30
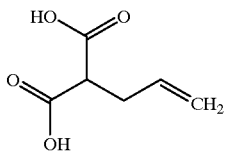
X-31
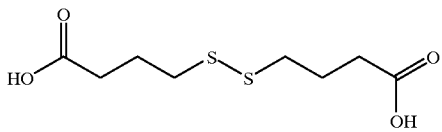
X-32

-continued
Diacids
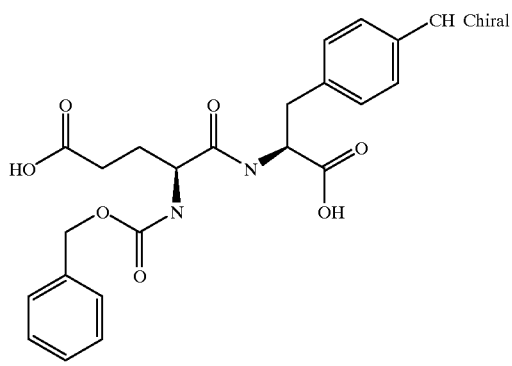
X-33
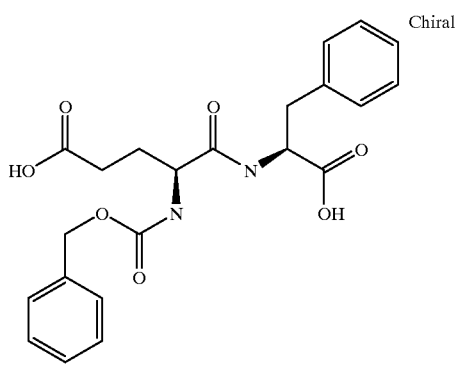
X-34
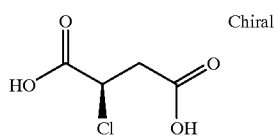
X-35
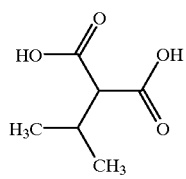
X-36
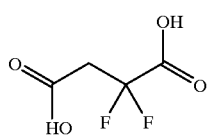
X-37
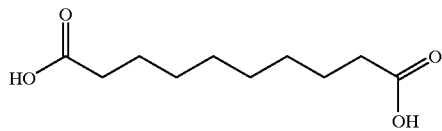
X-38

| -continued |
|---|
| Diacids |
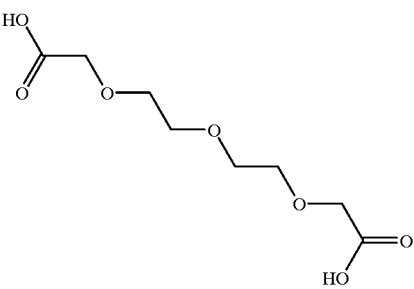
X-39
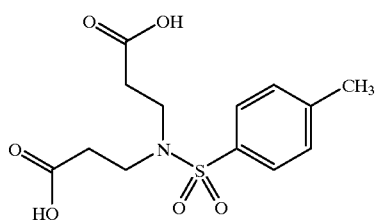
X-40
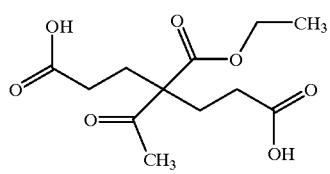
X-41
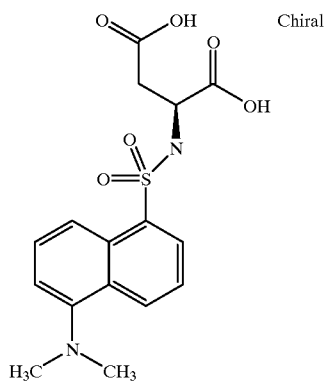
X-42
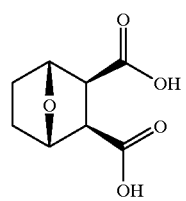
X-43
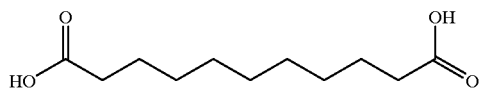
X-44

-continued
| Diacids | |
|---|---|
| 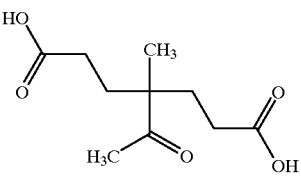 | X-45 |
| 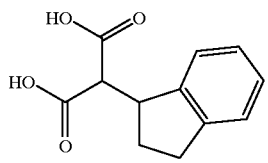 | X-46 |
| 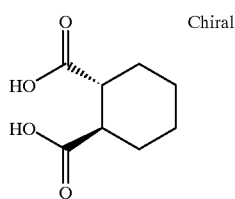 Chiral | X-47 |
| 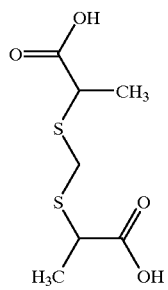 | X-48 |
| 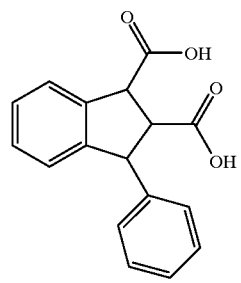 | X-49 |
| 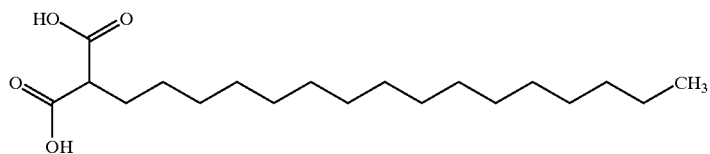 | X-50 |

| Diacids | |
|---|---|
| 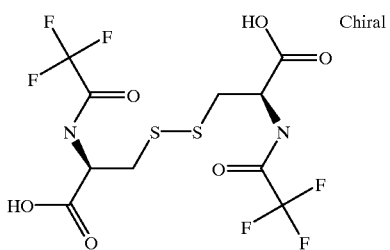 | X-51 |
| 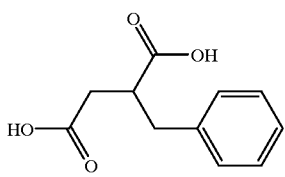 | X-52 |
| 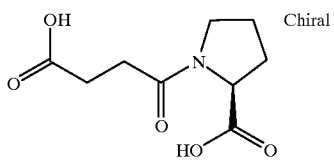 | X-53 |
| 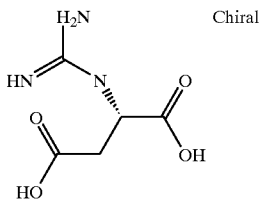 | X-54 |
| 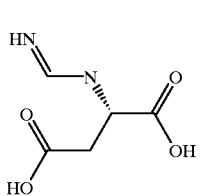 | X-55 |
| 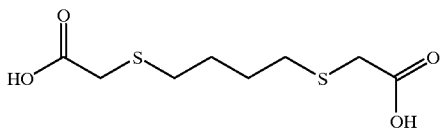 | X-56 |
| 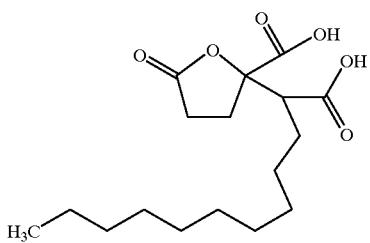 | |

-continued
Diacids
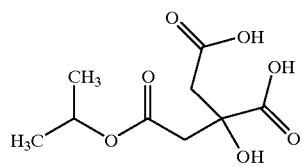 X-57
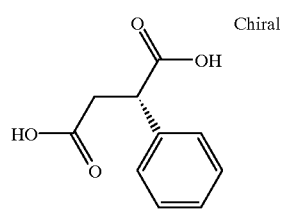 X-58
Chiral
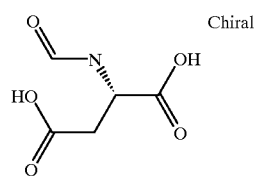 X-59
Chiral
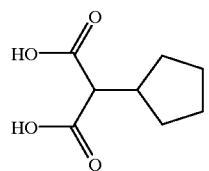 X-60
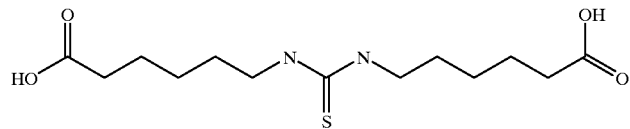 X-61
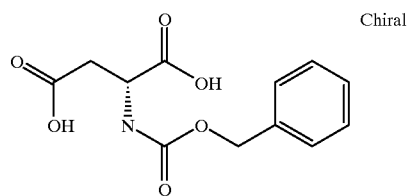 X-62
Chiral
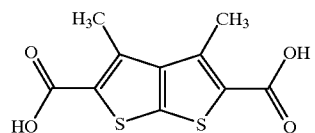 X-63
X-64

-continued
Diacids
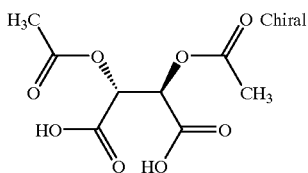
X-65
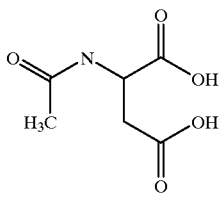
X-66
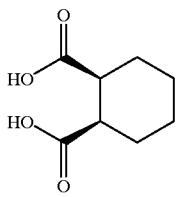
X-67
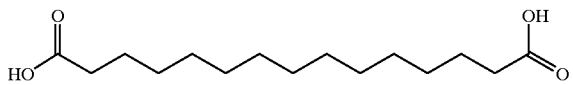
X-68
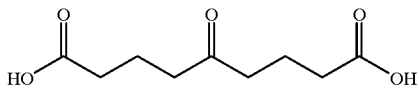
X-69
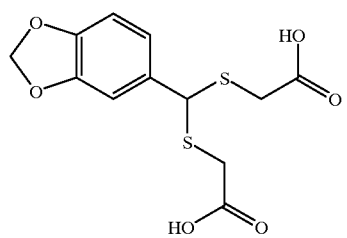
X-70
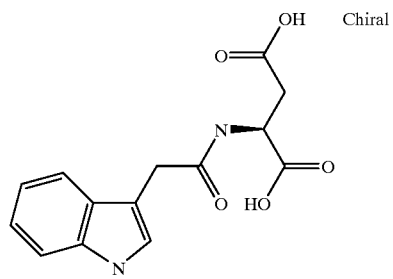
X-71

| -continued |
|---|
| Diacids |
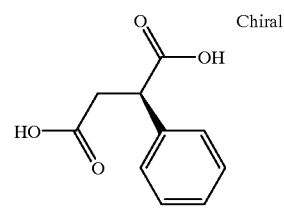
X-72
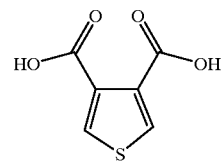
X-73
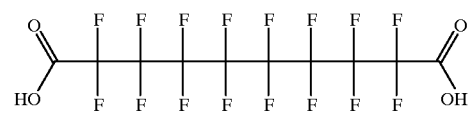
X-74
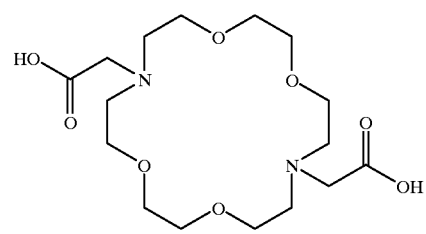
X-75
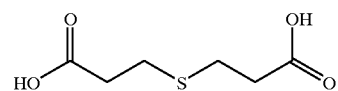
X-76
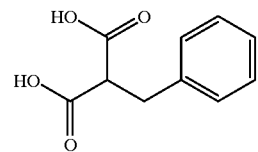
X-77
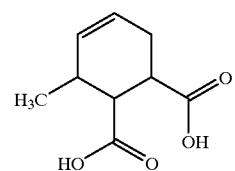
X-78
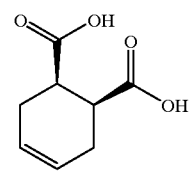

-continued
Diacids
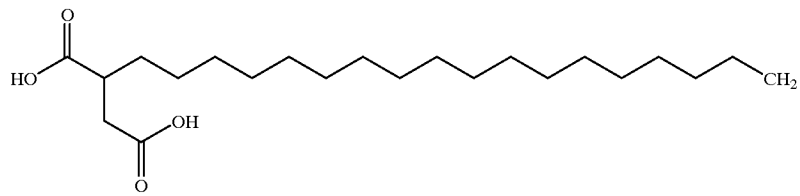
X-79
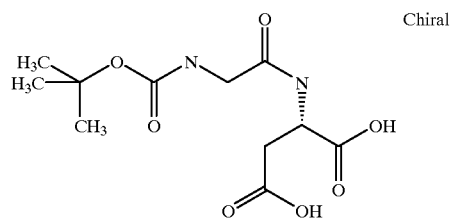
X-80
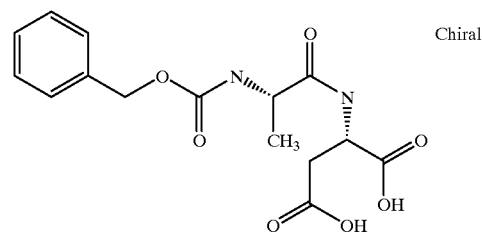
X-81
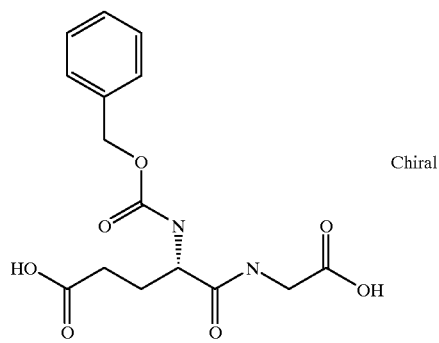
X-82
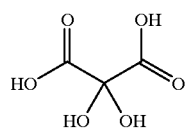
X-83
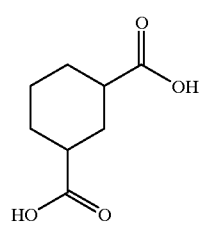
X-84

-continued
Diacids
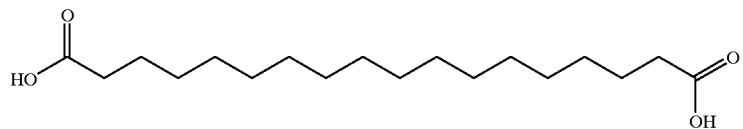
X-85
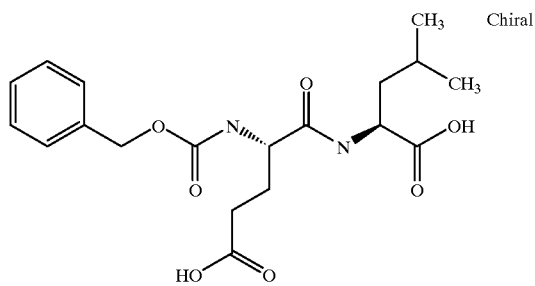
X-86
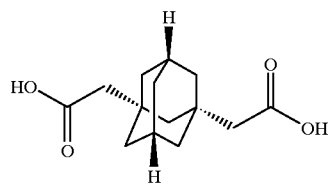
X-87
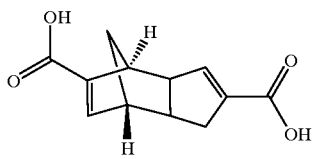
X-88
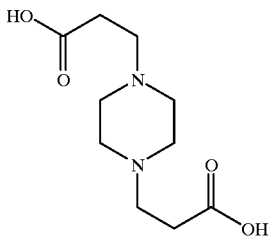
X-89
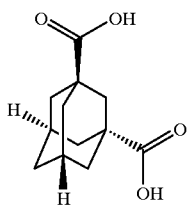
X-90
X-91

| Diacids | |
|---|---|
| 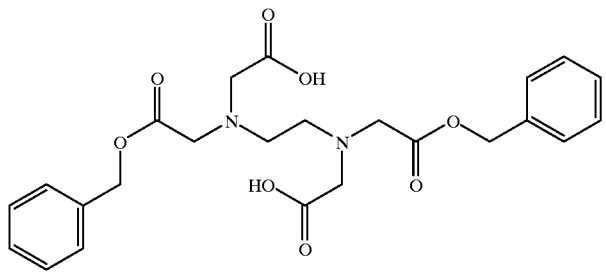 | X-92 |
| 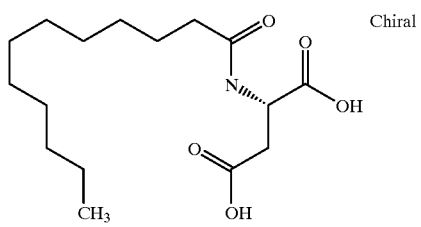 | X-93 |
| 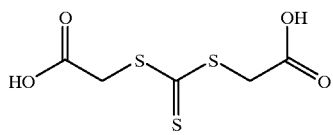 | X-94 |
| 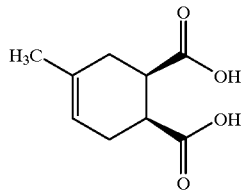 | X-95 |
| 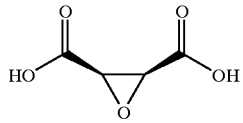 | X-96 |
| 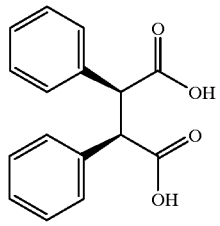 | X-97 |
| 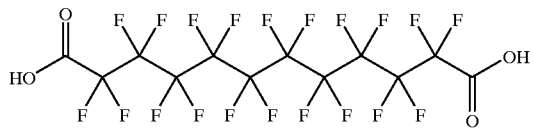 | X-98 |

-continued
Diacids
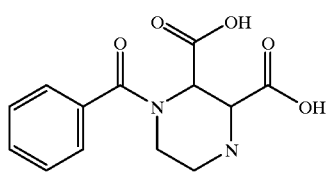
X-99
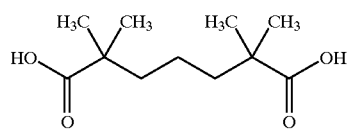
X-100
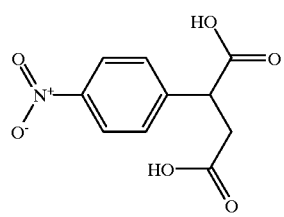
X-101
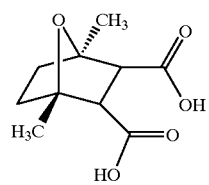
X-102
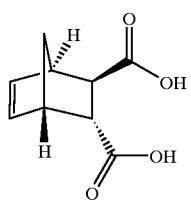
X-103
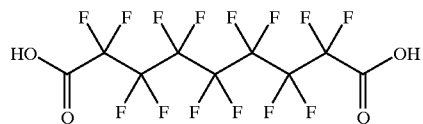
X-104
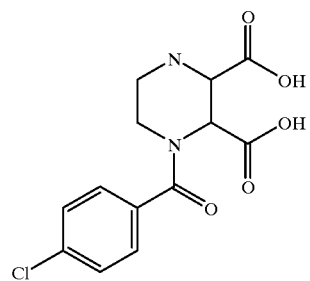
X-105

-continued
Diacids
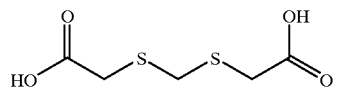
X-106
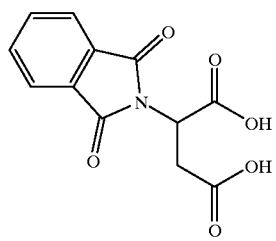
X-107
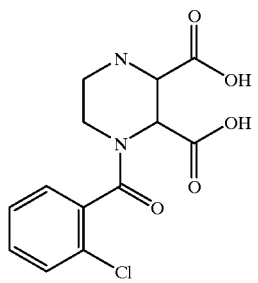
X-108
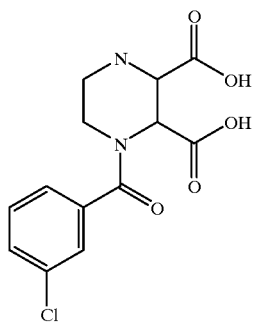
X-109
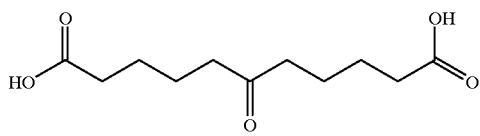
X-110
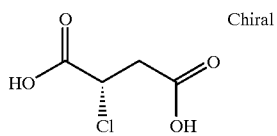
X-111

-continued
Diacids
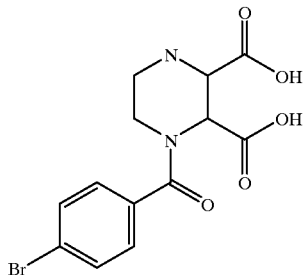
X-112
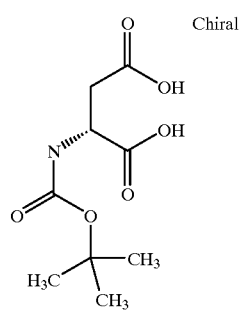
X-113
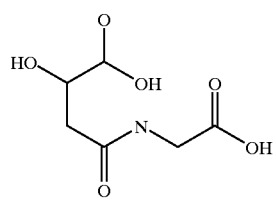
X-114
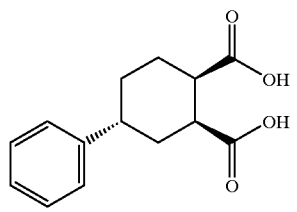
X-115
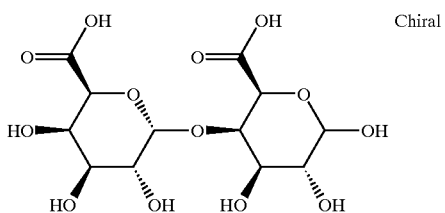
X-116

-continued
Diacids
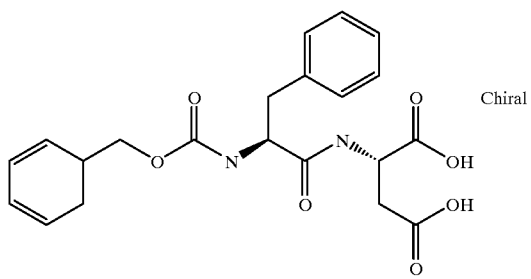
X-117
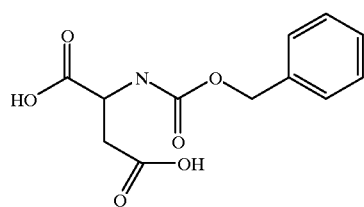
X-118
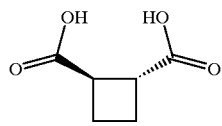
X-119
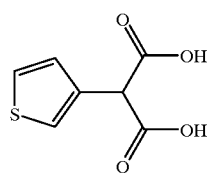
X-120
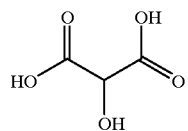
X-121
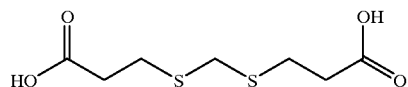
X-122
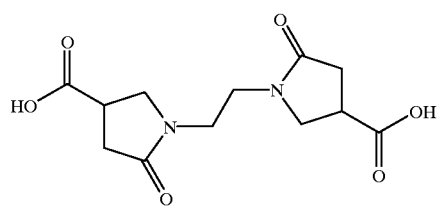
X-123

-continued
Diacids
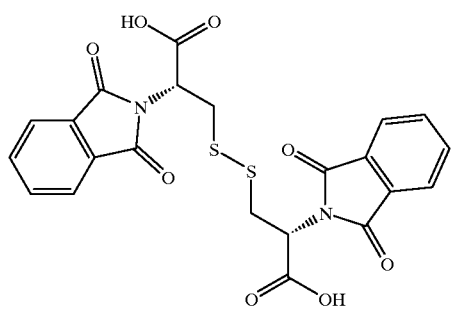
X-124
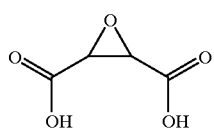
X-125
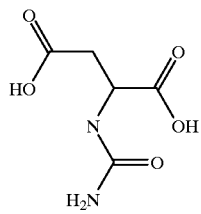
X-126
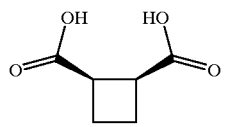
X-127
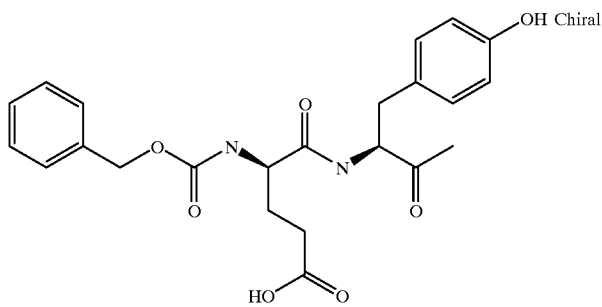
X-128
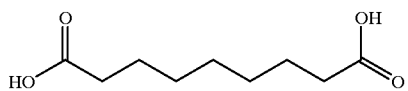
X-129
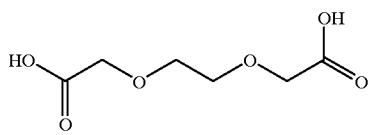
X-130

| -continued |  |
|---|---|
| Diacids | |
| 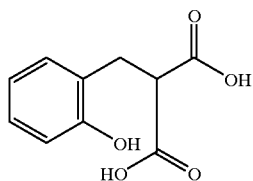 | X-131 |
| 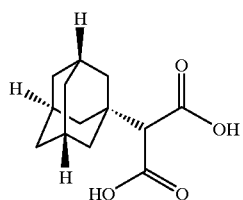 | X-132 |
| 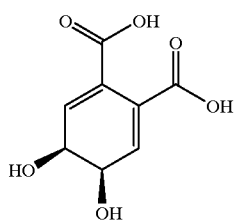 | X-133 |
| 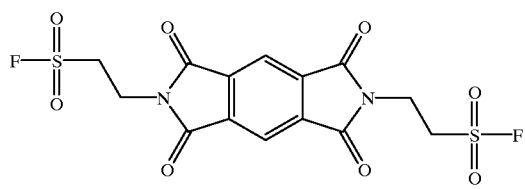 | X-134 |
| 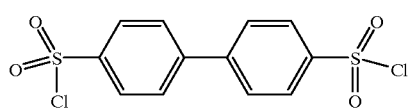 | X-135 |
| 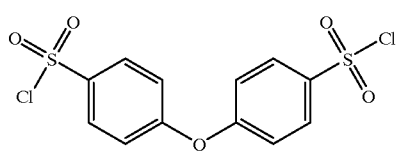 | X-136 |
| 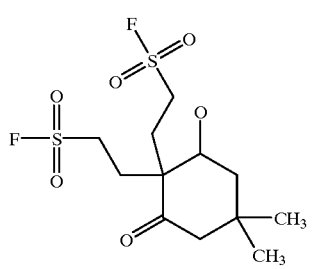 | X-137 |

-continued
Diacids
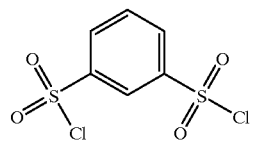
X-138
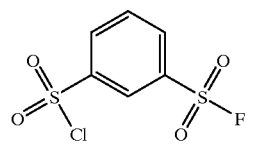
X-139
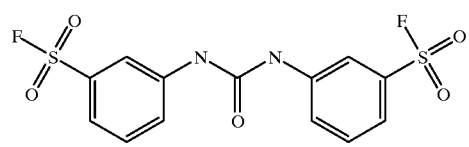
X-140
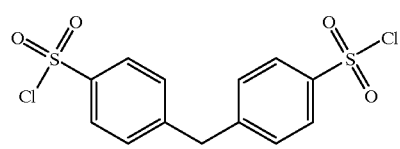
X-141
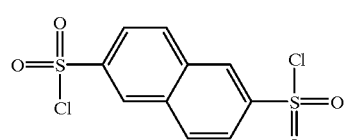
X-142
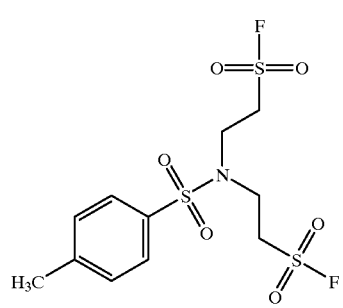
X-143
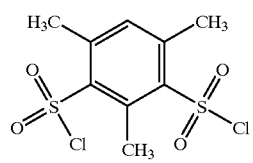
X-144

-continued
Diacids
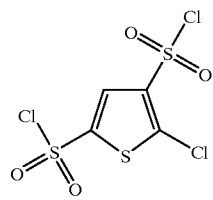
X-145
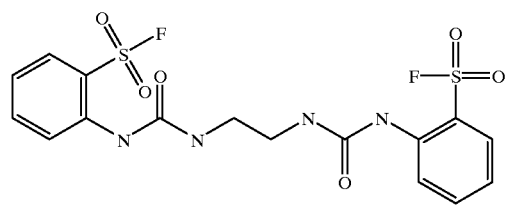
X-146
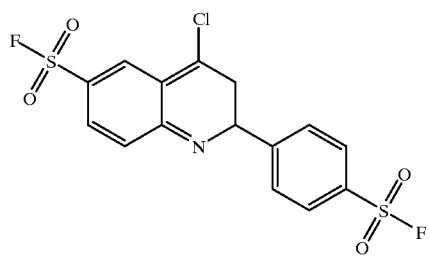
X-147
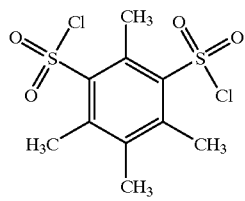
X-148
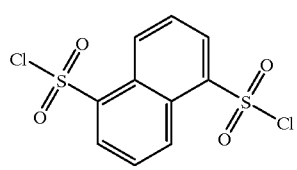
X-149
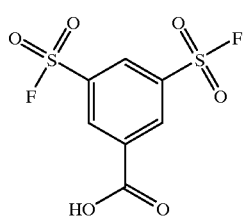
X-150

-continued
| Diacids | |
|---|---|
| 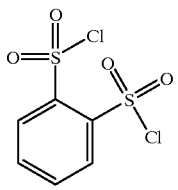 | X-151 |
| 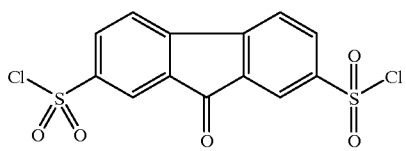 | X-152 |
| 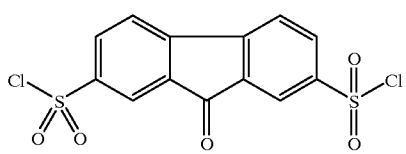 | X-153 |
| 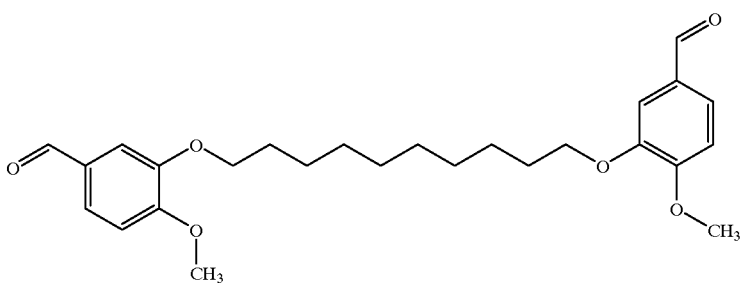 | X-154 |
| 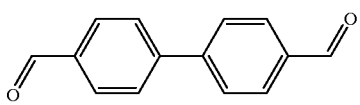 | X-155 |
| 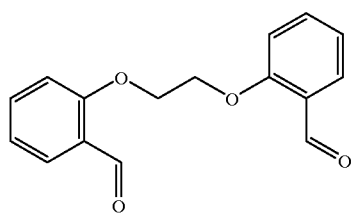 | X-156 |
| 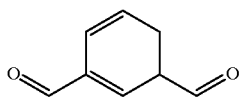 | X-157 |

-continued
| Diacids | |
|---|---|
| 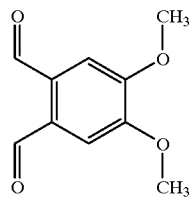 | X-158 |
| 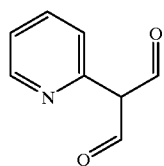 | X-159 |
| 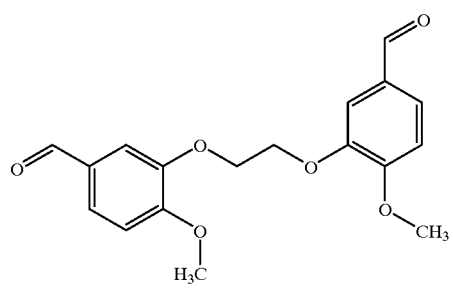 | X-160 |
| 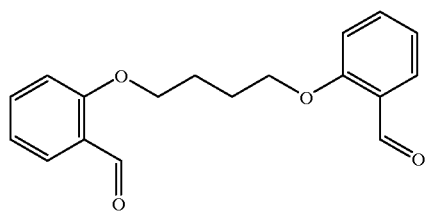 | X-161 |
| 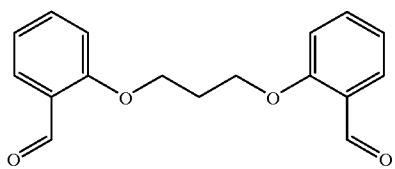 | X-162 |
| 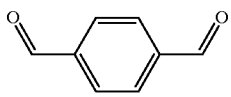 | X-163 |

| Diacids |
|---|
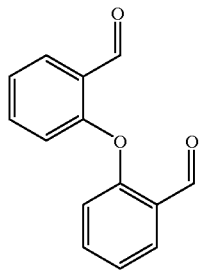
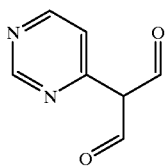
X-164
X-165
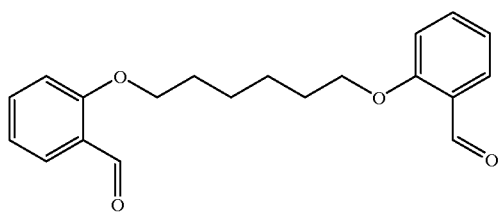
X-166
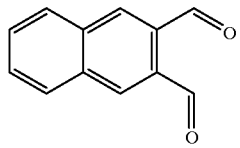
X-167
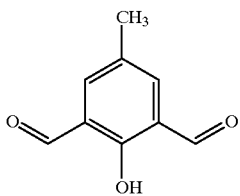
X-168
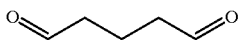
X-169
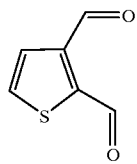
X-170

-continued
Diacids
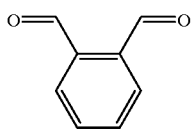
X-171
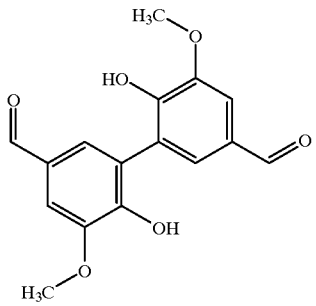
X-172
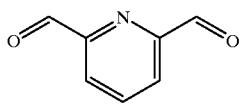
X-173
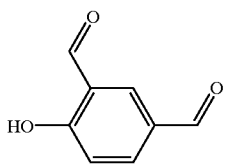
X-174
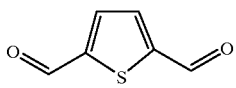
X-175
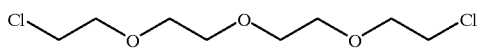
X-176
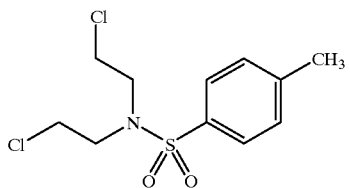
X-177
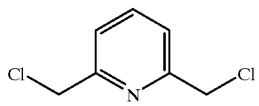
X-178
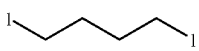
X-179

-continued
Diacids
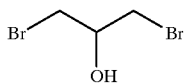
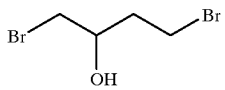
X-180
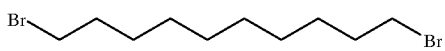
X-181
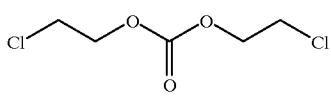
X-182
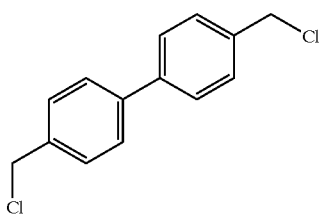
X-183
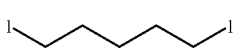
X-184
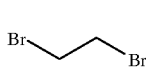
X-185
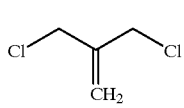
X-186
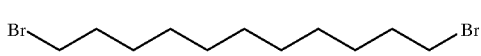
X-187
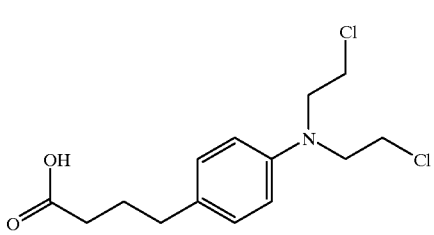
X-188
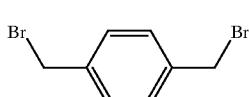
X-189
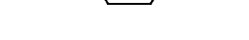
X-190

-continued
Diacids
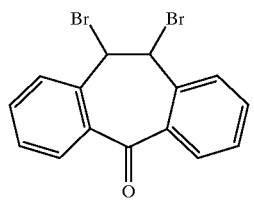
X-191
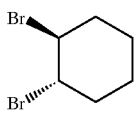
X-192
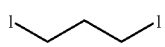
X-193
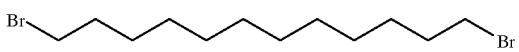
X-194
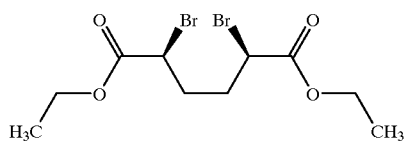
X-195
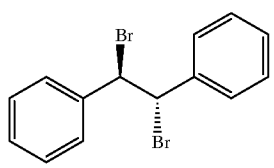
X-196
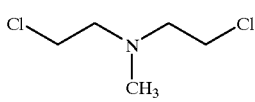
X-197
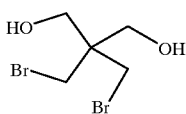
X-198
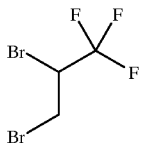
X-199
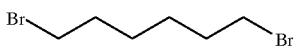
X-200
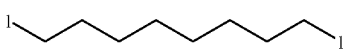

-continued
Diacids
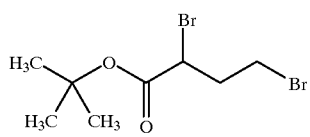
X-201
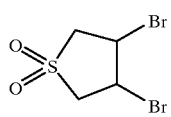
X-202
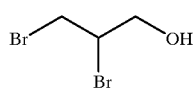
X-203
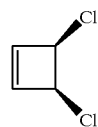
X-204
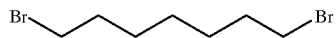
X-205
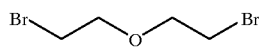
X-206
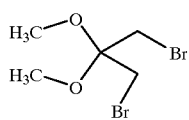
X-207
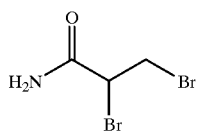
X-208
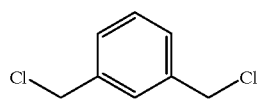
X-209
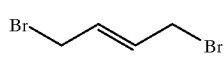
X-210
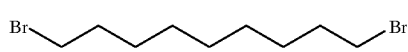
X-211
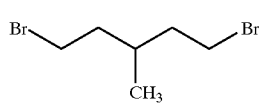
X-212

| -continued |  |
|---|---|
| Diacids | |
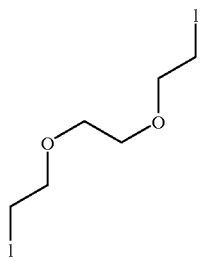
X-213
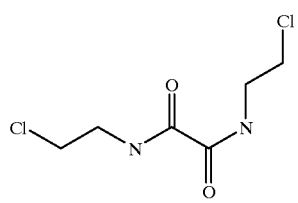
X-214
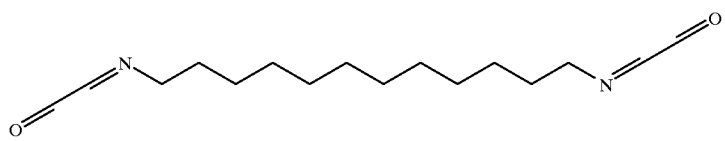
X-215
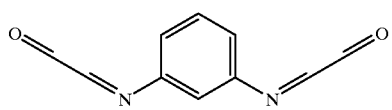
X-216
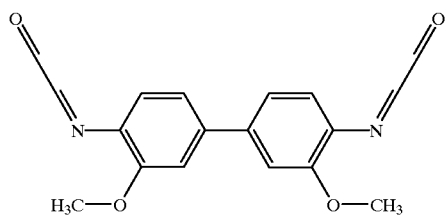
X-217
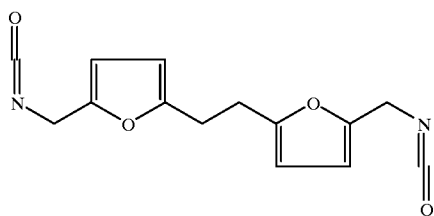
X-218
X-219

-continued
Diacids
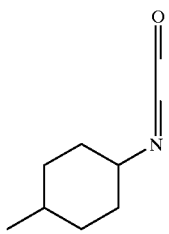
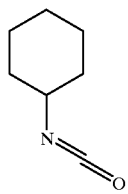
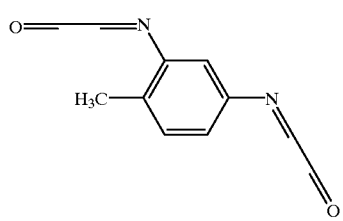
X-220
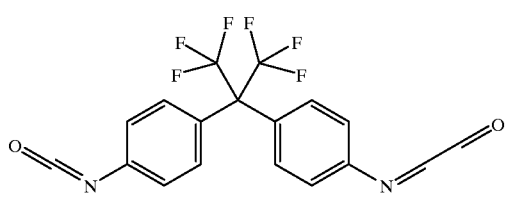
X-221
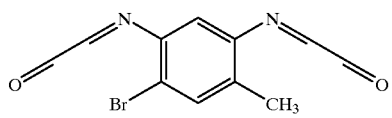
X-222
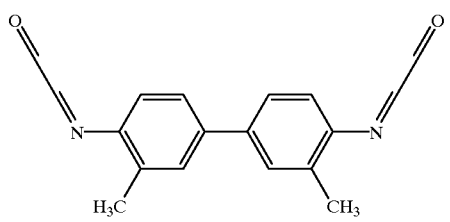
X-223
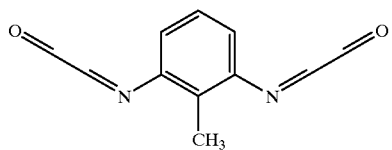
X-224
X-225

-continued
Diacids
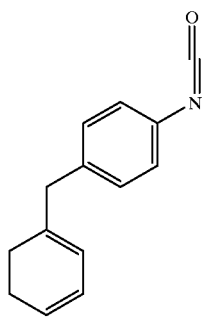
X-226
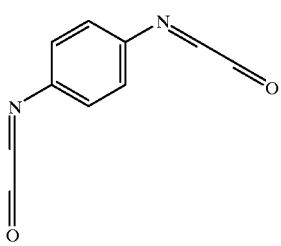
X-227
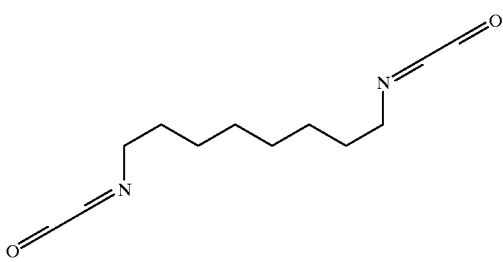
X-228
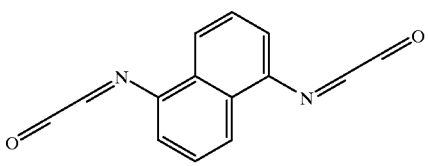
X-229
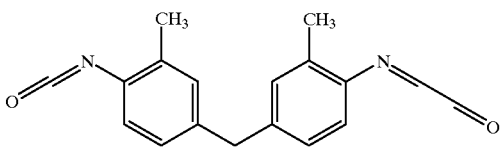
X-230
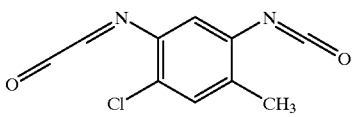
X-231

-continued
Diacids
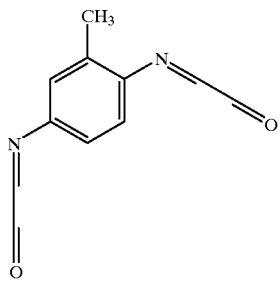 X-232
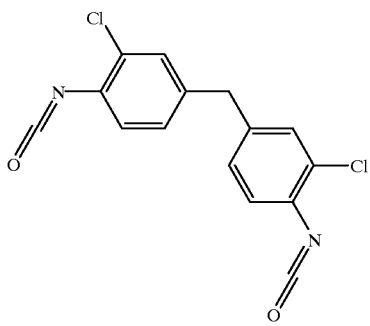 X-233
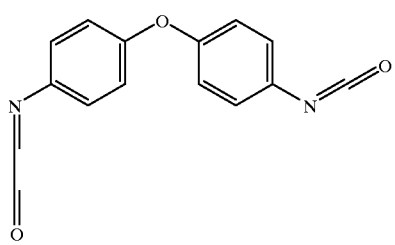 X-234
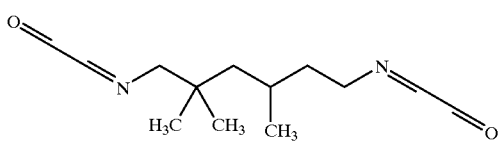 X-235
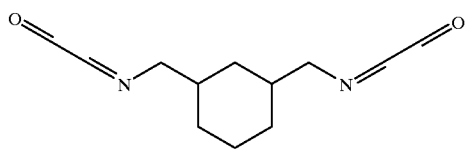 X-236
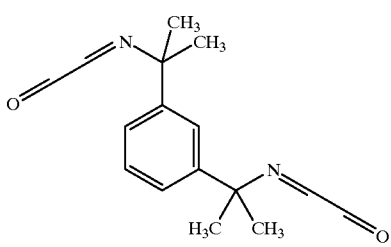

-continued
Diacids
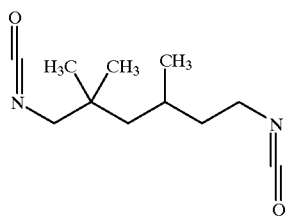
X-237
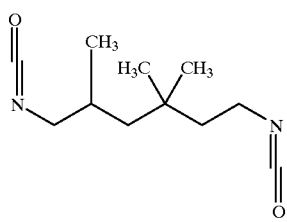
X-238
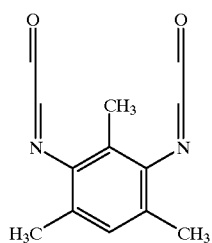
X-239
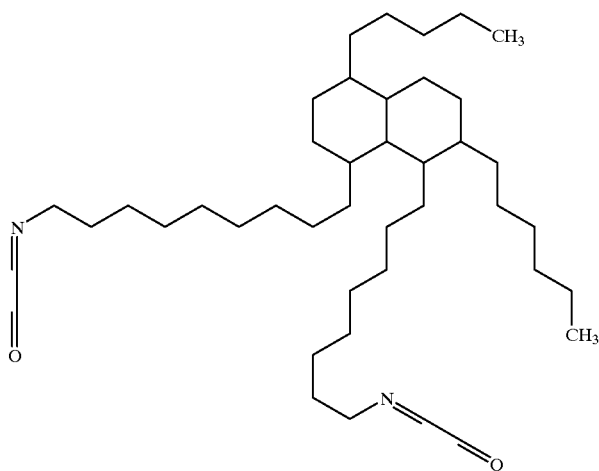
X-240
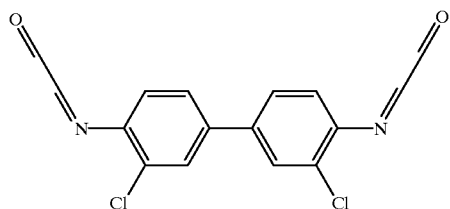
X-241

-continued
Diacids
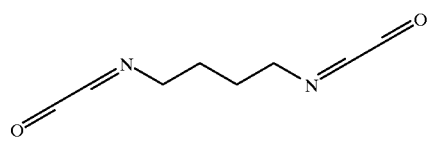
X-242
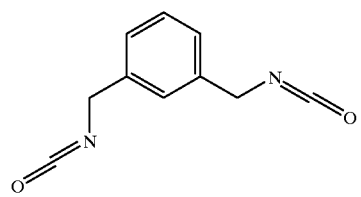
X-243
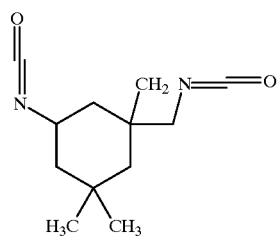
X-244
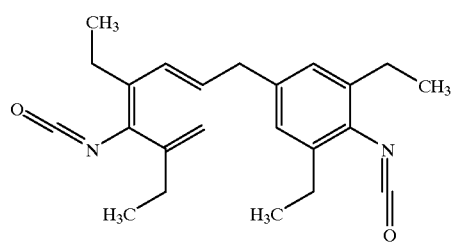
X-245
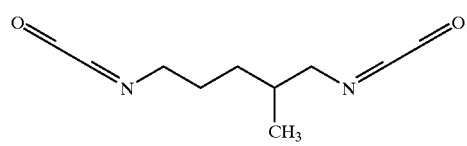
X-246
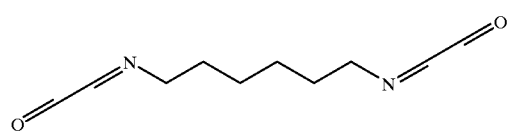
X-247
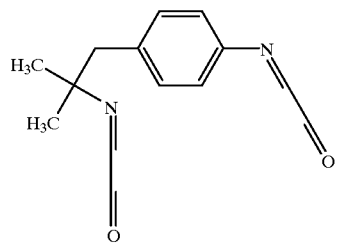

-continued
Diacids
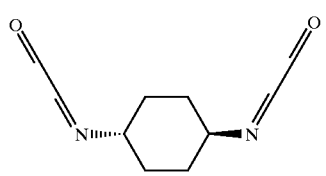
X-248
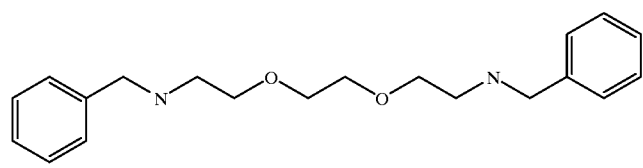
X-249
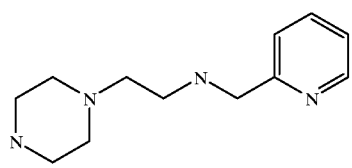
X-250
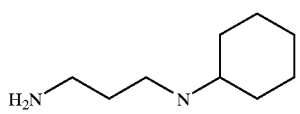
X-251
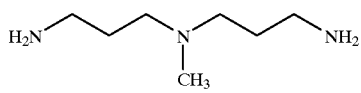
X-252
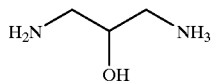
X-253
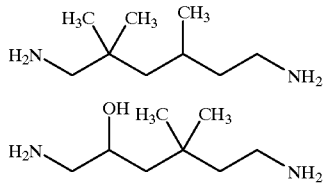
X-254
X-255
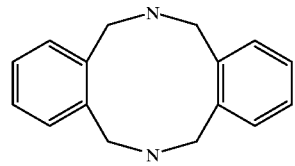
X-256
X-257

| -continued |
|---|
| Diacids |
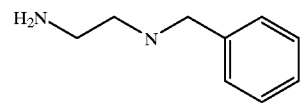
X-258
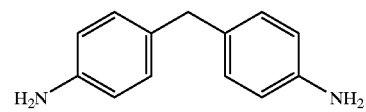
X-259
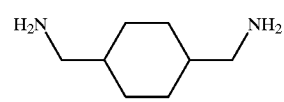
X-260
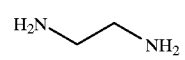
X-261
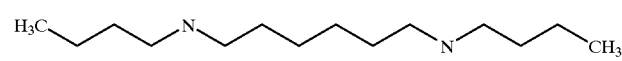
X-262
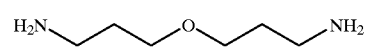
X-263
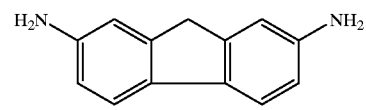
X-264
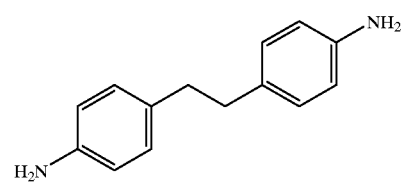
X-265
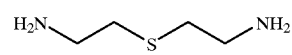
X-266
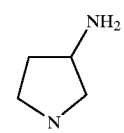
X-267
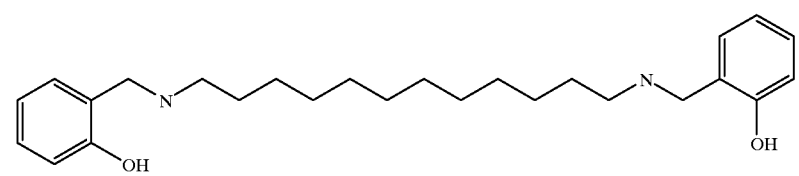
X-268

-continued
Diacids
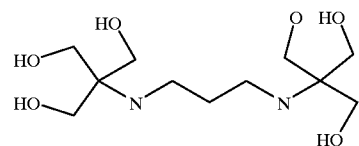
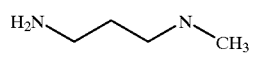
X-269
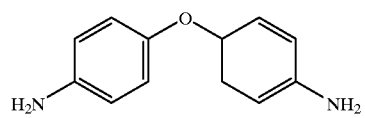
X-270
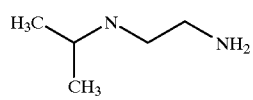
X-271
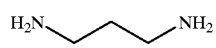
X-272
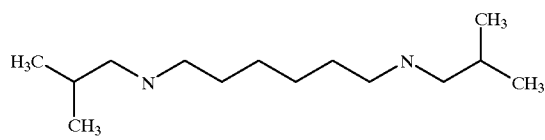
X-273
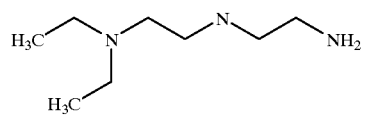
X-274
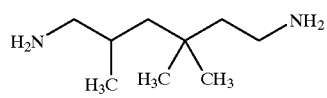
X-275
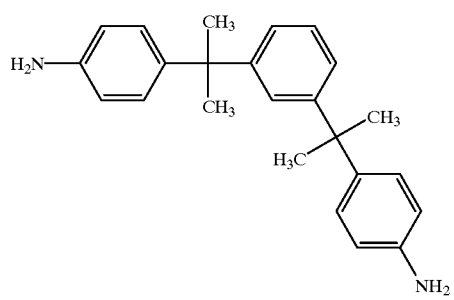
X-276
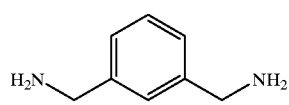
X-277

-continued
Diacids
X-278
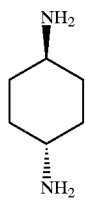
X-279
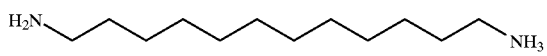
X-280
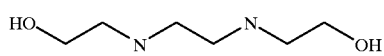
X-281
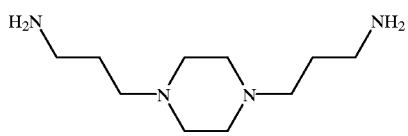
X-282
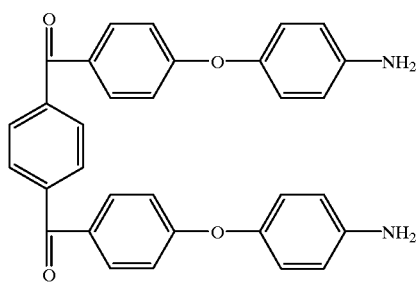
X-283
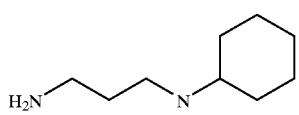
X-284
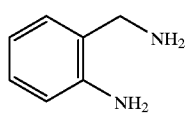
X-285
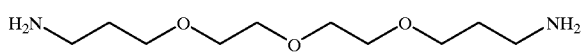
X-286
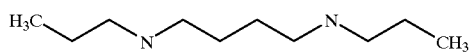
X-287
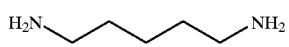
X-288

-continued
Diacids
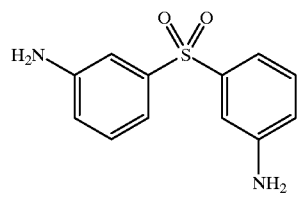
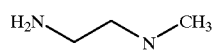
X-289
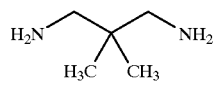
X-290
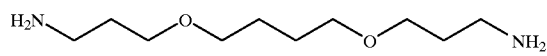
X-291
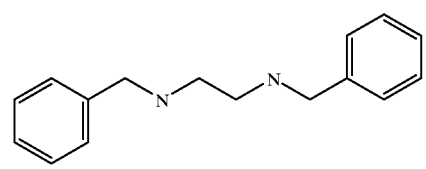
X-292
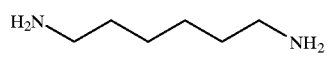
X-293
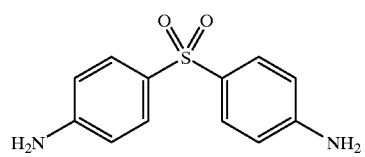
X-294
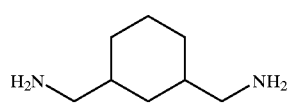
X-295
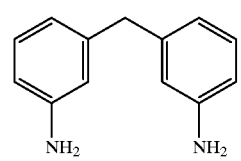
X-296
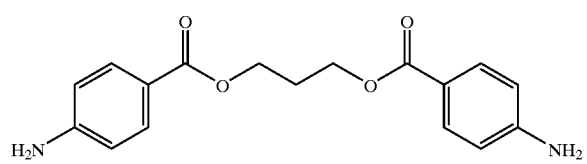
X-297
X-298

-continued
| Diacids | |
|---|---|
| 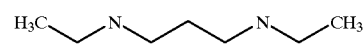 | X-299 |
| 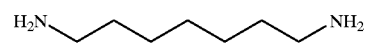 | X-300 |
| 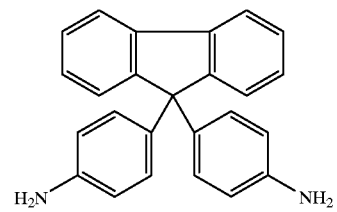 | X-301 |
| 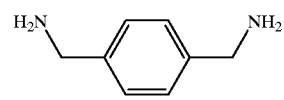 | X-302 |
| 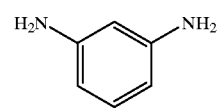 | X-303 |
| 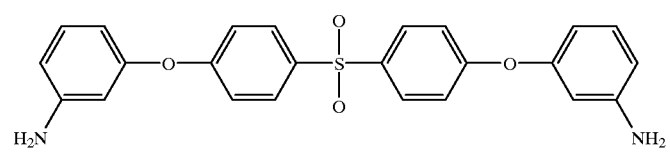 | X-304 |
| 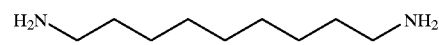 | X-305 |
| 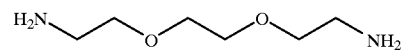 | X-306 |
| 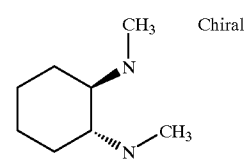 | X-307 |
| 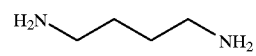 | X-308 |
| 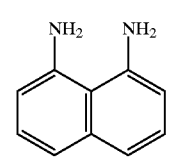 | X-309 |

-continued
Diacids
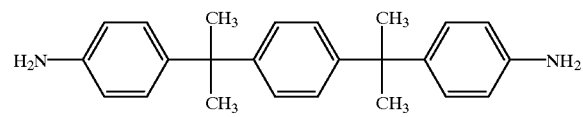
X-310
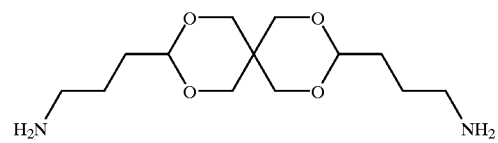
X-311
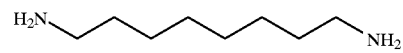
X-312
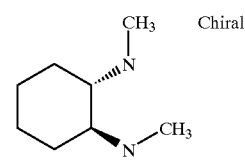
X-313
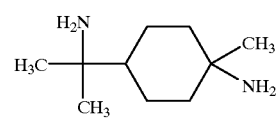
X-314
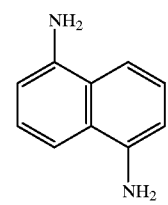
X-315
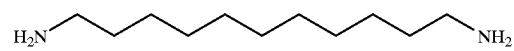
X-316
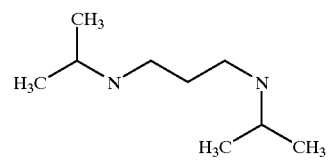
X-317
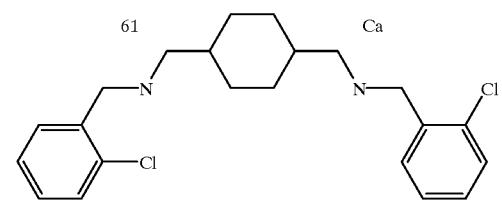
X-318

-continued
Diacids
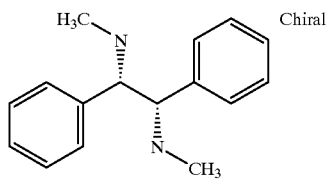
X-319
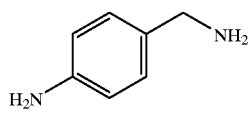
X-320
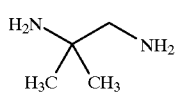
X-321
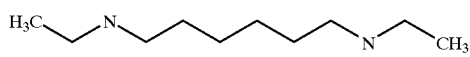
X-322
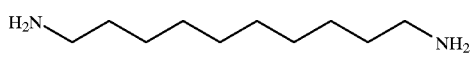
X-323
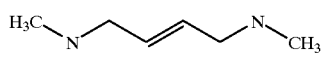
X-324
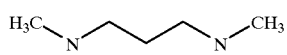
X-325
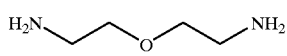
X-326
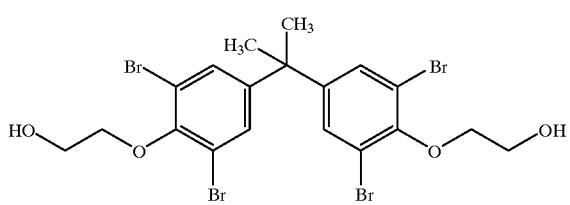
X-327
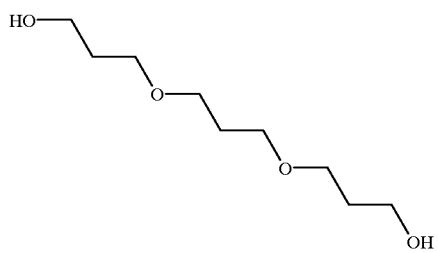
X-328

| -continued |
|---|
| Diacids |
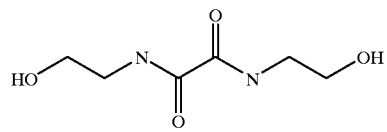
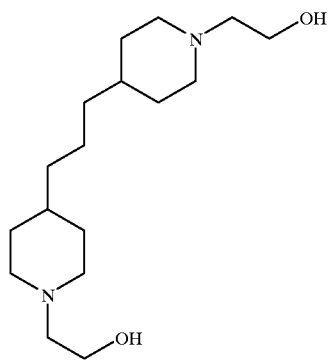
X-329
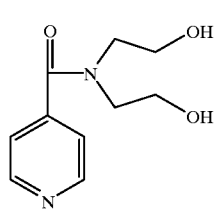
X-330
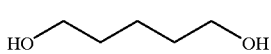
X-331
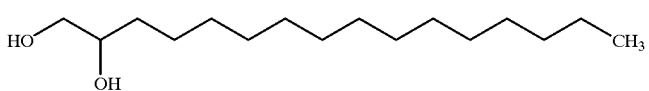
X-332
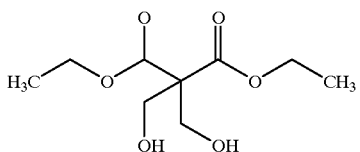
X-333
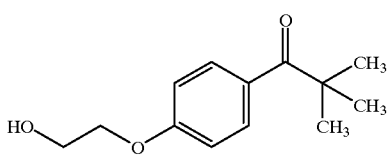
X-334
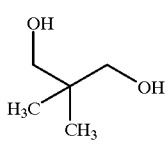
X-335
X-336

| Diacids | |
|---|---|
| 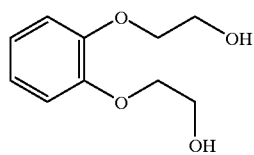 | X-337 |
| 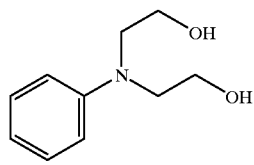 | X-338 |
| 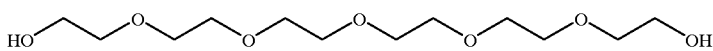 | X-339 |
| 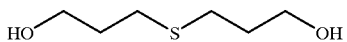 | X-340 |
| 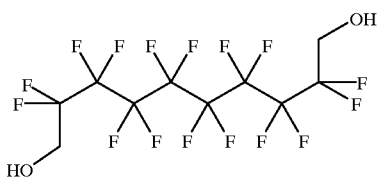 | X-341 |
| 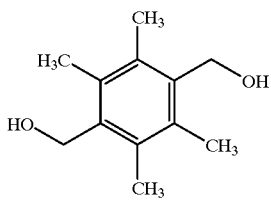 | X-342 |
| 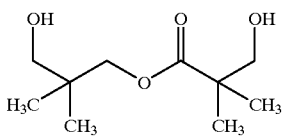 | X-343 |
| 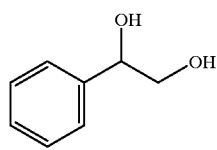 | X-344 |
| 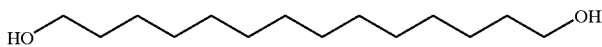 | X-345 |
| 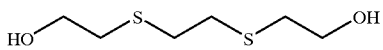 | X-346 |

| -continued |  |
|---|---|
| Diacids |  |
| 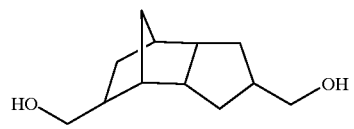 | X-347 |
| 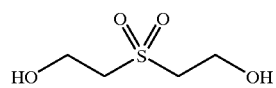 | X-348 |
| 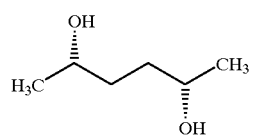 | X-349 |
| 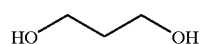 | X-350 |
| 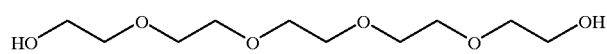 | X-351 |
| 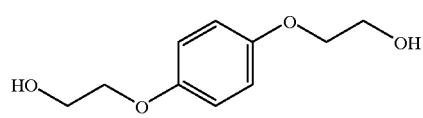 | X-352 |
| 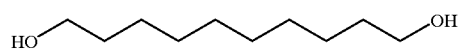 | X-353 |
| 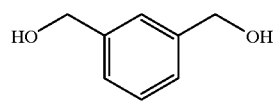 | X-354 |
| 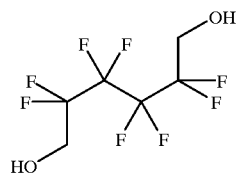 | X-355 |
| 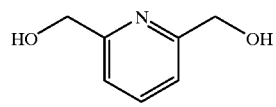 | X-356 |

-continued
Diacids
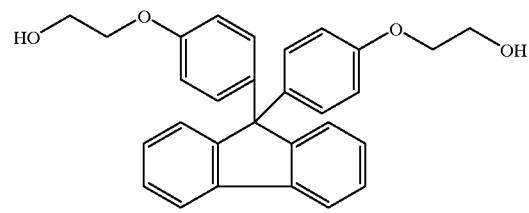
X-357
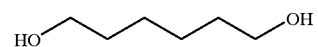
X-358
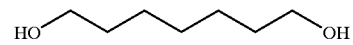
X-359
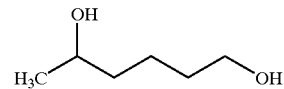
X-360
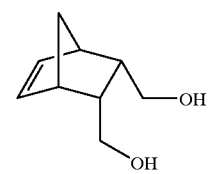
X-361
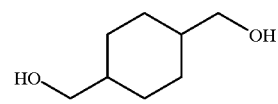
X-362
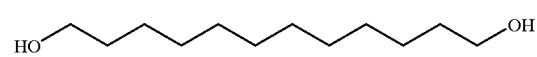
X-363
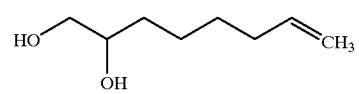
X-364
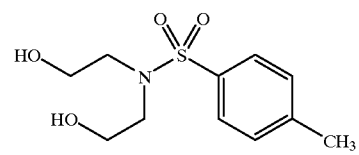
X-365
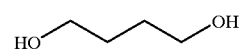
X-366
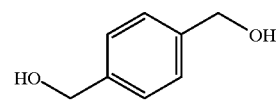
X-367

-continued
| Diacids | |
|---|---|
| 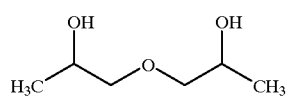 | X-368 |
| 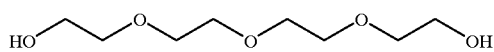 | X-369 |
| 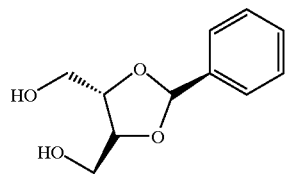 | X-370 |
| 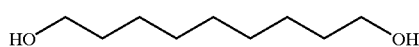 | X-371 |
| 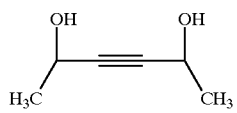 | X-372 |
| 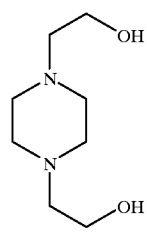 | X-373 |
| 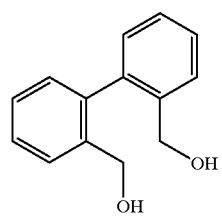 | X-374 |
| 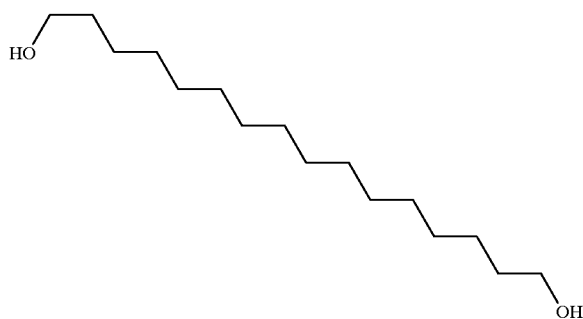 | X-375 |

-continued
Diacids
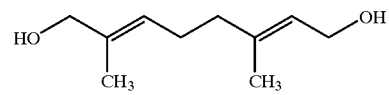
X-376
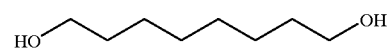
X-377
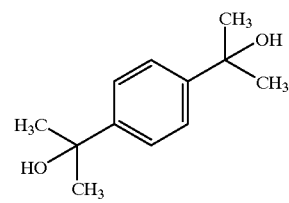
X-378
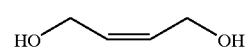
X-379
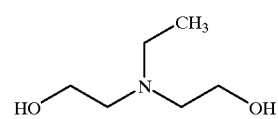
X-380
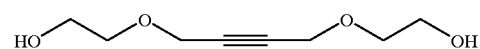
X-381
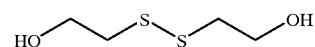
X-382
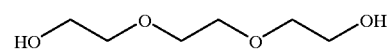
X-383
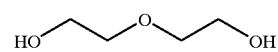
X-384
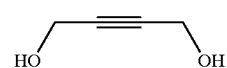
X-385
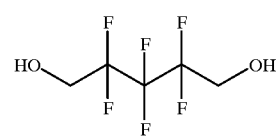
X-386
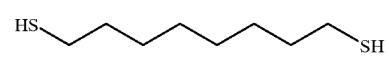
X-387
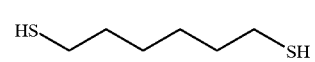
X-388

-continued
Diacids
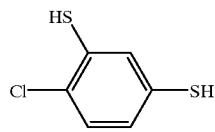
X-389
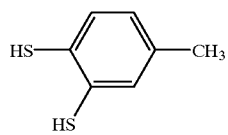
X-390
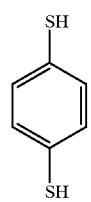
X-391
X-392
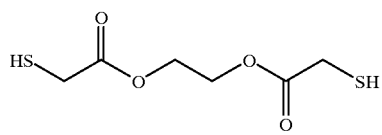
X-393
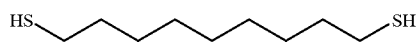
X-394
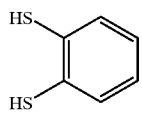
X-395
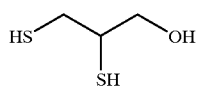
X-396
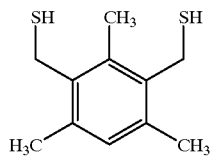
X-397

-continued
Diacids
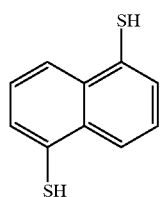
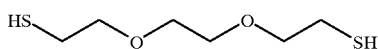
X-398
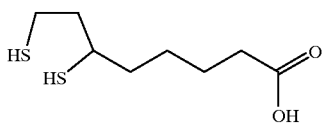
X-399
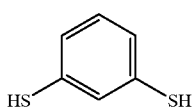
X-400
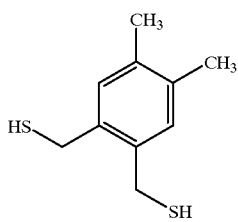
X-401
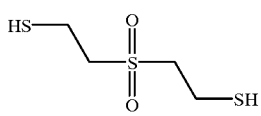
X-402
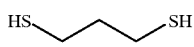
X-403
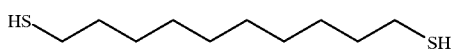
X-404
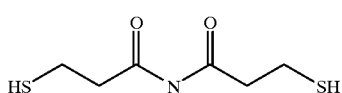
X-405
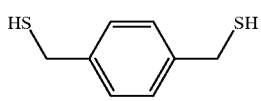
X-406
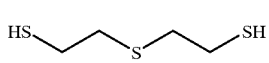
X-407
X-408

-continued
Diacids
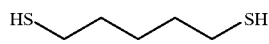
X-409
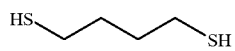
X-410
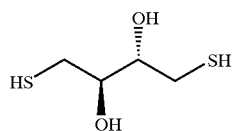
X-411
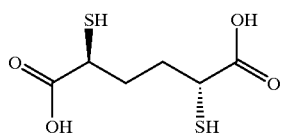
X-412
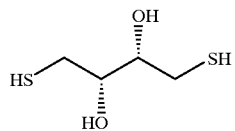
X-413
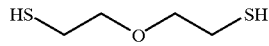
X-414
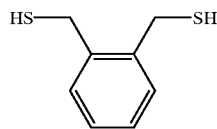
X-415
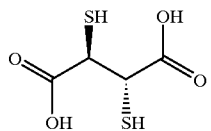
X-416
Chiral
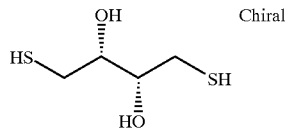
X-417
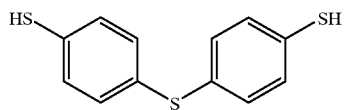
X-418
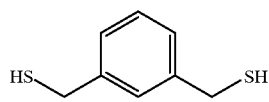

Representative ligands for use in this invention include, by way of example, ligands of formula IA–ID and IIA–IID as defined herein.

Combinations of ligands (L) and linkers (X) per this invention include, by way example only, homo- and heterodimers wherein a first ligand is selected from formula IA through ID above and the second ligand and linker is selected from the following:

| | | | | | |
|---|---|---|---|---|---|
| IA/X-1- | IA/X-2- | IA/X-3- | IA/X-4- | IA/X-5- | IA/X-6- |
| IA/X-7- | IA/X-8- | IA/X-9- | IA/X-10- | IA/X-11- | IA/X-12- |
| IA/X-13- | IA/X-14- | IA/X-15- | IA/X-16- | IA/X-17- | IA/X-18- |
| IA/X-19- | IA/X-20- | IA/X-21- | IA/X-22- | IA/X-23- | IA/X-24- |
| IA/X-25- | IA/X-26- | IA/X-27- | IA/X-28- | IA/X-29- | IA/X-30- |
| IA/X-31- | IA/X-32- | IA/X-33- | IA/X-34- | IA/X-35- | IA/X-36- |
| IA/X-37- | IA/X-38- | IA/X-39- | IA/X-40- | IA/X-41- | IA/X-42- |
| IA/X-43- | IA/X-44- | IA/X-45- | IA/X-46- | IA/X-47- | IA/X-48- |
| IA/X-49- | IA/X-50- | IA/X-51- | IA/X-52- | IA/X-53- | IA/X-54- |
| IA/X-55- | IA/X-56- | IA/X-57- | IA/X-58- | IA/X-59- | IA/X-60- |
| IA/X-61- | IA/X-62- | IA/X-63- | IA/X-64- | IA/X-65- | IA/X-66- |
| IA/X-67- | IA/X-68- | IA/X-69- | IA/X-70- | IA/X-71- | IA/X-72- |
| IA/X-73- | IA/X-74- | IA/X-75- | IA/X-76- | IA/X-77- | IA/X-78- |
| IA/X-79- | IA/X-80- | IA/X-81- | IA/X-82- | IA/X-83- | IA/X-84- |
| IA/X-85- | IA/X-86- | IA/X-87- | IA/X-88- | IA/X-89- | IA/X-90- |
| IA/X-91- | IA/X-92- | IA/X-93- | IA/X-94- | IA/X-95- | IA/X-96- |
| IA/X-97- | IA/X-98- | IA/X-99- | IA/X-100- | IA/X-101- | IA/X-102- |
| IA/X-103- | IA/X-104- | IA/X-105- | IA/X-106- | IA/X-107- | IA/X-108- |
| IA/X-109- | IA/X-110- | IA/X-111- | IA/X-112- | IA/X-113- | IA/X-114- |
| IA/X-115- | IA/X-116- | IA/X-117- | IA/X-118- | IA/X-119- | IA/X-120- |
| IA/X-121- | IA/X-122- | IA/X-123- | IA/X-124- | IA/X-125- | IA/X-126- |
| IA/X-127- | IA/X-128- | IA/X-129- | IA/X-130- | IA/X-131- | IA/X-132- |
| IA/X-133- | IA/X-134- | IA/X-135- | IA/X-136- | IA/X-137- | IA/X-138- |
| IA/X-139- | IA/X-140- | IA/X-141- | IA/X-142- | IA/X-143- | IA/X-144- |
| IA/X-145- | IA/X-146- | IA/X-147- | IA/X-148- | IA/X-149- | IA/X-150- |
| IA/X-151- | IA/X-152- | IA/X-153- | IA/X-154- | IA/X-155- | IA/X-156- |
| IA/X-157- | IA/X-158- | IA/X-159- | IA/X-160- | IA/X-161- | IA/X-162- |
| IA/X-163- | IA/X-164- | IA/X-165- | IA/X-166- | IA/X-167- | IA/X-168- |
| IA/X-169- | IA/X-170- | IA/X-171- | IA/X-172- | | |
| IA/X-173- | IA/X-174- | IA/X-175- | IA/X-176- | IA/X-177- | IA/X-178- |
| IA/X-179- | IA/X-180- | IA/X-181- | IA/X-182- | IA/X-183- | IA/X-184- |
| IA/X-185- | IA/X-186- | IA/X-187- | IA/X-188- | IA/X-189- | IA/X-190- |
| IA/X-191- | IA/X-192- | IA/X-193- | IA/X-194- | IA/X-195- | IA/X-196- |
| IA/X-197- | IA/X-198- | IA/X-199- | IA/X-200- | IA/X-201- | IA/X-202- |
| IA/X-203- | IA/X-204- | IA/X-205- | IA/X-206- | IA/X-207- | IA/X-208- |
| IA/X-209- | IA/X-210- | IA/X-211- | IA/X-212- | IA/X-213- | IA/X-214- |
| IA/X-215- | IA/X-216- | IA/X-217- | IA/X-218- | IA/X-219- | IA/X-220- |
| IA/X-221- | IA/X-222- | IA/X-223- | IA/X-224- | IA/X-225- | IA/X-226- |
| IA/X-227- | IA/X-228- | IA/X-229- | IA/X-230- | IA/X-231- | IA/X-232- |
| IA/X-233- | IA/X-234- | IA/X-235- | IA/X-236- | IA/X-237- | IA/X-238- |
| IA/X-239- | IA/X-240- | IA/X-241- | IA/X-242- | IA/X-243- | IA/X-244- |
| IA/X-245- | IA/X-246- | IA/X-247- | IA/X-248- | IA/X-249- | IA/X-250- |
| IA/X-251- | IA/X-252- | IA/X-253- | IA/X-254- | IA/X-255- | IA/X-256- |
| IA/X-257- | IA/X-258- | IA/X-259- | IA/X-260- | IA/X-261- | IA/X-262- |
| IA/X-263- | IA/X-264- | IA/X-265- | IA/X-266- | IA/X-267- | IA/X-268- |
| IA/X-269- | IA/X-270- | IA/X-271- | IA/X-272- | IA/X-273- | IA/X-274- |
| IA/X-275- | IA/X-276- | IA/X-277- | IA/X-278- | IA/X-279- | IA/X-280- |
| IA/X-281- | IA/X-282- | IA/X-283- | IA/X-284- | IA/X-285- | IA/X-286- |
| IA/X-287- | IA/X-288- | IA/X-289- | IA/X-290- | IA/X-291- | IA/X-292- |
| IA/X-293- | IA/X-294- | IA/X-295- | IA/X-296- | IA/X-297- | IA/X-298- |
| IA/X-299- | IA/X-300- | IA/X-301- | IA/X-302- | IA/X-303- | IA/X-304- |
| IA/X-305- | IA/X-306- | IA/X-307- | IA/X-308- | IA/X-309- | IA/X-310- |
| IA/X-311- | IA/X-312- | IA/X-313- | IA/X-314- | IA/X-315- | IA/X-316- |
| IA/X-317- | IA/X-318- | IA/X-319- | IA/X-320- | IA/X-321- | IA/X-322- |
| IA/X-323- | IA/X-324- | IA/X-325- | IA/X-326- | IA/X-327- | IA/X-328- |
| IA/X-329- | IA/X-330- | IA/X-331- | IA/X-332- | IA/X-333- | IA/X-334- |
| IA/X-335- | IA/X-336- | IA/X-337- | IA/X-338- | IA/X-339- | IA/X-340- |
| IA/X-341- | IA/X-342- | IA/X-343- | IA/X-344- | IA/X-345- | IA/X-346- |
| IA/X-347- | IA/X-348- | IA/X-349- | IA/X-350- | IA/X-351- | IA/X-352- |
| IA/X-353- | IA/X-354- | IA/X-355- | IA/X-356- | IA/X-357- | IA/X-358- |
| IA/X-359- | IA/X-360- | IA/X-361- | IA/X-362- | IA/X-363- | IA/X-364- |
| IA/X-365- | IA/X-366- | IA/X-367- | IA/X-368- | IA/X-369- | IA/X-370- |
| IA/X-371- | IA/X-372- | IA/X-373- | IA/X-374- | IA/X-375- | IA/X-376- |
| IA/X-377- | IA/X-378- | IA/X-379- | IA/X-380- | IA/X-381- | IA/X-382- |
| IA/X-383- | IA/X-384- | IA/X-385- | IA/X-386- | IA/X-387- | IA/X-388- |
| IA/X-389- | IA/X-390- | IA/X-391- | IA/X-392- | IA/X-393- | IA/X-394- |
| IA/X-395- | IA/X-396- | IA/X-397- | IA/X-398- | IA/X-399- | IA/X-400- |
| IA/X-401- | IA/X-402- | IA/X-403- | IA/X-404- | IA/X-405- | IA/X-406- |

-continued

| | | | | | |
|---|---|---|---|---|---|
| IA/X-407- | IA/X-408- | IA/X-409- | IA/X-410- | IA/X-411- | IA/X-412- |
| IA/X-413- | IA/X-414- | IA/X-415- | IA/X-416- | IA/X-417- | IA/X-418- |
| IB/X-1- | IB/X-2- | IB/X-3- | IB/X-4- | IB/X-5- | IB/X-6- |
| IB/X-7- | IB/X-8- | IB/X-9- | IB/X-10- | IB/X-11- | IB/X-12- |
| IB/X-13- | IB/X-14- | IB/X-15- | IB/X-16- | IB/X-17- | IB/X-18- |
| IB/X-19- | IB/X-20- | IB/X-21- | IB/X-22- | IB/X-23- | IB/X-24- |
| IB/X-25- | IB/X-26- | IB/X-27- | IB/X-28- | IB/X-29- | IB/X-30- |
| IB/X-31- | IB/X-32- | IB/X-33- | IB/X-34- | IB/X-35- | IB/X-36- |
| IB/X-37- | IB/X-38- | IB/X-39- | IB/X-40- | IB/X-41- | IB/X-42- |
| IB/X-43- | IB/X-44- | IB/X-45- | IB/X-46- | IB/X-47- | IB/X-48- |
| IB/X-49- | IB/X-50- | IB/X-51- | IB/X-52- | IB/X-53- | IB/X-54- |
| IB/X-55- | IB/X-56- | IB/X-57- | IB/X-58- | IB/X-59- | IB/X-60- |
| IB/X-61- | IB/X-62- | IB/X-63- | IB/X-64- | IB/X-65- | IB/X-66- |
| IB/X-67- | IB/X-68- | IB/X-69- | IB/X-70- | IB/X-71- | IB/X-72- |
| IB/X-73- | IB/X-74- | IB/X-75- | IB/X-76- | IB/X-77- | IB/X-78- |
| IB/X-79- | IB/X-80- | IB/X-81- | IB/X-82- | IB/X-83- | IB/X-84- |
| IB/X-85- | IB/X-86- | IB/X-87- | IB/X-88- | IB/X-89- | IB/X-90- |
| IB/X-91- | IB/X-92- | IB/X-93- | IB/X-94- | IB/X-95- | IB/X-96- |
| IB/X-97- | IB/X-98- | IB/X-99- | IB/X-100- | IB/X-101- | IB/X-102- |
| IB/X-103- | IB/X-104- | IB/X-105- | IB/X-106- | IB/X-107- | IB/X-108- |
| IB/X-109- | IB/X-110- | IB/X-111- | IB/X-112- | IB/X-113- | IB/X-114- |
| IB/X-115- | IB/X-116- | IB/X-117- | IB/X-118- | IB/X-119- | IB/X-120- |
| IB/X-121- | IB/X-122- | IB/X-123- | IB/X-124- | IB/X-125- | IB/X-126- |
| IB/X-127- | IB/X-128- | IB/X-129- | IB/X-130- | IB/X-131- | IB/X-132- |
| IB/X-133- | IB/X-134- | IB/X-135- | IB/X-136- | IB/X-137- | IB/X-138- |
| IB/X-139- | IB/X-140- | IB/X-141- | IB/X-142- | IB/X-143- | IB/X-144- |
| IB/X-145- | IB/X-146- | IB/X-147- | IB/X-148- | IB/X-149- | IB/X-150- |
| IB/X-151- | IB/X-152- | IB/X-153- | IB/X-154- | IB/X-155- | IB/X-156- |
| IB/X-157- | IB/X-158- | IB/X-159- | IB/X-160- | IB/X-161- | IB/X-162- |
| IB/X-163- | IB/X-164- | IB/X-165- | IB/X-166- | IB/X-167- | IB/X-168- |
| IB/X-169- | IB/X-170- | IB/X-171- | IB/X-172- | | |
| IB/X-173- | IB/X-174- | IB/X-175- | IB/X-176- | IB/X-177- | IB/X-178- |
| IB/X-179- | IB/X-180- | IB/X-181- | IB/X-182- | IB/X-183- | IB/X-184- |
| IB/X-185- | IB/X-186- | IB/X-187- | IB/X-188- | IB/X-189- | IB/X-190- |
| IB/X-191- | IB/X-192- | IB/X-193- | IB/X-194- | IB/X-195- | IB/X-196- |
| IB/X-197- | IB/X-198- | IB/X-199- | IB/X-200- | IB/X-201- | IB/X-202- |
| IB/X-203- | IB/X-204- | IB/X-205- | IB/X-206- | IB/X-207- | IB/X-208- |
| IB/X-209- | IB/X-210- | IB/X-211- | IB/X-212- | IB/X-213- | IB/X-214- |
| IB/X-215- | IB/X-216- | IB/X-217- | IB/X-218- | IB/X-219- | IB/X-220- |
| IB/X-221- | IB/X-222- | IB/X-223- | IB/X-224- | IB/X-225- | IB/X-226- |
| IB/X-227- | IB/X-228- | IB/X-229- | IB/X-230- | IB/X-231- | IB/X-232- |
| IB/X-233- | IB/X-234- | IB/X-235- | IB/X-236- | IB/X-237- | IB/X-238- |
| IB/X-239- | IB/X-240- | IB/X-241- | IB/X-242- | IB/X-243- | IB/X-244- |
| IB/X-245- | IB/X-246- | IB/X-247- | IB/X-248- | IB/X-249- | IB/X-250- |
| IB/X-251- | IB/X-252- | IB/X-253- | IB/X-254- | IB/X-255- | IB/X-256- |
| IB/X-257- | IB/X-258- | IB/X-259- | IB/X-260- | IB/X-261- | IB/X-262- |
| IB/X-263- | IB/X-264- | IB/X-265- | IB/X-266- | IB/X-267- | IB/X-268- |
| IB/X-269- | IB/X-270- | IB/X-271- | IB/X-272- | IB/X-273- | IB/X-274- |
| IB/X-275- | IB/X-276- | IB/X-277- | IB/X-278- | IB/X-279- | IB/X-280- |
| IB/X-281- | IB/X-282- | IB/X-283- | IB/X-284- | IB/X-285- | IB/X-286- |
| IB/X-287- | IB/X-288- | IB/X-289- | IB/X-290- | IB/X-291- | IB/X-292- |
| IB/X-293- | IB/X-294- | IB/X-295- | IB/X-296- | IB/X-297- | IB/X-298- |
| IB/X-299- | IB/X-300- | IB/X-301- | IB/X-302- | IB/X-303- | IB/X-304- |
| IB/X-305- | IB/X-306- | IB/X-307- | IB/X-308- | IB/X-309- | IB/X-310- |
| IB/X-311- | IB/X-312- | IB/X-313- | IB/X-314- | IB/X-315- | IB/X-316- |
| IB/X-317- | IB/X-318- | IB/X-319- | IB/X-320- | IB/X-321- | IB/X-322- |
| IB/X-323- | IB/X-324- | IB/X-325- | IB/X-326- | IB/X-327- | IB/X-328- |
| IB/X-329- | IB/X-330- | IB/X-331- | IB/X-332- | IB/X-333- | IB/X-334- |
| IB/X-335- | IB/X-336- | IB/X-337- | IB/X-338- | IB/X-339- | IB/X-340- |
| IB/X-341- | IB/X-342- | IB/X-343- | IB/X-344- | IB/X-345- | IB/X-346- |
| IB/X-347- | IB/X-348- | IB/X-349- | IB/X-350- | IB/X-351- | IB/X-352- |
| IB/X-353- | IB/X-354- | IB/X-355- | IB/X-356- | IB/X-357- | IB/X-358- |
| IB/X-359- | IB/X-360- | IB/X-361- | IB/X-362- | IB/X-363- | IB/X-364- |
| IB/X-365- | IB/X-366- | IB/X-367- | IB/X-368- | IB/X-369- | IB/X-370- |
| IB/X-371- | IB/X-372- | IB/X-373- | IB/X-374- | IB/X-375- | IB/X-376- |
| IB/X-377- | IB/X-378- | IB/X-379- | IB/X-380- | IB/X-381- | IB/X-382- |
| IB/X-383- | IB/X-384- | IB/X-385- | IB/X-386- | IB/X-387- | IB/X-388- |
| IB/X-389- | IB/X-390- | IB/X-391- | IB/X-392- | IB/X-393- | IB/X-394- |
| IB/X-395- | IB/X-396- | IB/X-397- | IB/X-398- | IB/X-399- | IB/X-400- |
| IB/X-401- | IB/X-402- | IB/X-403- | IB/X-404- | IB/X-405- | IB/X-406- |
| IB/X-407- | IB/X-408- | IB/X-409- | IB/X-410- | IB/X-411- | IB/X-412- |
| IB/X-413- | IB/X-414- | IB/X-415- | IB/X-416- | IB/X-417- | IB/X-418- |
| IC/X-1- | IC/X-2- | IC/X-3- | IC/X-4- | IC/X-5- | IC/X-6- |
| IC/X-7- | IC/X-8- | IC/X-9- | IC/X-10- | IC/X-11- | IC/X-12- |
| IC/X-13- | IC/X-14- | IC/X-15- | IC/X-16- | IC/X-17- | IC/X-18- |
| IC/X-19- | IC/X-20- | IC/X-21- | IC/X-22- | IC/X-23- | IC/X-24- |
| IC/X-25- | IC/X-26- | IC/X-27- | IC/X-28- | IC/X-29- | IC/X-30- |
| IC/X-31- | IC/X-32- | IC/X-33- | IC/X-34- | IC/X-35- | IC/X-36- |
| IC/X-37- | IC/X-38- | IC/X-39- | IC/X-40- | IC/X-41- | IC/X-42- |

| | | | | | |
|---|---|---|---|---|---|
| IC/X-43- | IC/X-44- | IC/X-45- | IC/X-46- | IC/X-47- | IC/X-48- |
| IC/X-49- | IC/X-50- | IC/X-51- | IC/X-52- | IC/X-53- | IC/X-54- |
| IC/X-55- | IC/X-56- | IC/X-57- | IC/X-58- | IC/X-59- | IC/X-60- |
| IC/X-61- | IC/X-62- | IC/X-63- | IC/X-64- | IC/X-65- | IC/X-66- |
| IC/X-67- | IC/X-68- | IC/X-69- | IC/X-70- | IC/X-71- | IC/X-72- |
| IC/X-73- | IC/X-74- | IC/X-75- | IC/X-76- | IC/X-77- | IC/X-78- |
| IC/X-79- | IC/X-80- | IC/X-81- | IC/X-82- | IC/X-83- | IC/X-84- |
| IC/X-85- | IC/X-86- | IC/X-87- | IC/X-88- | IC/X-89- | IC/X-90- |
| IC/X-91- | IC/X-92- | IC/X-93- | IC/X-94- | IC/X-95- | IC/X-96- |
| IC/X-97- | IC/X-98- | IC/X-99- | IC/X-100- | IC/X-101- | IC/X-102- |
| IC/X-103- | IC/X-104- | IC/X-105- | IC/X-106- | IC/X-107- | IC/X-108- |
| IC/X-109- | IC/X-110- | IC/X-111- | IC/X-112- | IC/X-113- | IC/X-114- |
| IC/X-115- | IC/X-116- | IC/X-117- | IC/X-118- | IC/X-119- | IC/X-120- |
| IC/X-121- | IC/X-122- | IC/X-123- | IC/X-124- | IC/X-125- | IC/X-126- |
| IC/X-127- | IC/X-128- | IC/X-129- | IC/X-130- | IC/X-131- | IC/X-132- |
| IC/X-133- | IC/X-134- | IC/X-135- | IC/X-136- | IC/X-137- | IC/X-138- |
| IC/X-139- | IC/X-140- | IC/X-141- | IC/X-142- | IC/X-143- | IC/X-144- |
| IC/X-145- | IC/X-146- | IC/X-147- | IC/X-148- | IC/X-149- | IC/X-150- |
| IC/X-151- | IC/X-152- | IC/X-153- | IC/X-154- | IC/X-155- | IC/X-156- |
| IC/X-157- | IC/X-158- | IC/X-159- | IC/X-160- | IC/X-161- | IC/X-162- |
| IC/X-163- | IC/X-164- | IC/X-165- | IC/X-166- | IC/X-167- | IC/X-168- |
| IC/X-169- | IC/X-170- | IC/X-171- | IC/X-172- | | |
| IC/X-173- | IC/X-174- | IC/X-175- | IC/X-176- | IC/X-177- | IC/X-178- |
| IC/X-179- | IC/X-180- | IC/X-181- | IC/X-182- | IC/X-183- | IC/X-184- |
| IC/X-185- | IC/X-186- | IC/X-187- | IC/X-188- | IC/X-189- | IC/X-190- |
| IC/X-191- | IC/X-192- | IC/X-193- | IC/X-194- | IC/X-195- | IC/X-196- |
| IC/X-197- | IC/X-198- | IC/X-199- | IC/X-200- | IC/X-201- | IC/X-202- |
| IC/X-203- | IC/X-204- | IC/X-205- | IC/X-206- | IC/X-207- | IC/X-208- |
| IC/X-209- | IC/X-210- | IC/X-211- | IC/X-212- | IC/X-213- | IC/X-214- |
| IC/X-215- | IC/X-216- | IC/X-217- | IC/X-218- | IC/X-219- | IC/X-220- |
| IC/X-221- | IC/X-222- | IC/X-223- | IC/X-224- | IC/X-225- | IC/X-226- |
| IC/X-227- | IC/X-228- | IC/X-229- | IC/X-230- | IC/X-231- | IC/X-232- |
| IC/X-233- | IC/X-234- | IC/X-235- | IC/X-236- | IC/X-237- | IC/X-238- |
| IC/X-239- | IC/X-240- | IC/X-241- | IC/X-242- | IC/X-243- | IC/X-244- |
| IC/X-245- | IC/X-246- | IC/X-247- | IC/X-248- | IC/X-249- | IC/X-250- |
| IC/X-251- | IC/X-252- | IC/X-253- | IC/X-254- | IC/X-255- | IC/X-256- |
| IC/X-257- | IC/X-258- | IC/X-259- | IC/X-260- | IC/X-261- | IC/X-262- |
| IC/X-263- | IC/X-264- | IC/X-265- | IC/X-266- | IC/X-267- | IC/X-268- |
| IC/X-269- | IC/X-270- | IC/X-271- | IC/X-272- | IC/X-273- | IC/X-274- |
| IC/X-275- | IC/X-276- | IC/X-277- | IC/X-278- | IC/X-279- | IC/X-280- |
| IC/X-281- | IC/X-282- | IC/X-283- | IC/X-284- | IC/X-285- | IC/X-286- |
| IC/X-287- | IC/X-288- | IC/X-289- | IC/X-290- | IC/X-291- | IC/X-292- |
| IC/X-293- | IC/X-294- | IC/X-295- | IC/X-296- | IC/X-297- | IC/X-298- |
| IC/X-299- | IC/X-300- | IC/X-301- | IC/X-302- | IC/X-303- | IC/X-304- |
| IC/X-305- | IC/X-306- | IC/X-307- | IC/X-308- | IC/X-309- | IC/X-310- |
| IC/X-311- | IC/X-312- | IC/X-313- | IC/X-314- | IC/X-315- | IC/X-316- |
| IC/X-317- | IC/X-318- | IC/X-319- | IC/X-320- | IC/X-321- | IC/X-322- |
| IC/X-323- | IC/X-324- | IC/X-325- | IC/X-326- | IC/X-327- | IC/X-328- |
| IC/X-329- | IC/X-330- | IC/X-331- | IC/X-332- | IC/X-333- | IC/X-334- |
| IC/X-335- | IC/X-336- | IC/X-337- | IC/X-338- | IC/X-339- | IC/X-340- |
| IC/X-341- | IC/X-342- | IC/X-343- | IC/X-344- | IC/X-345- | IC/X-346- |
| IC/X-347- | IC/X-348- | IC/X-349- | IC/X-350- | IC/X-351- | IC/X-352- |
| IC/X-353- | IC/X-354- | IC/X-355- | IC/X-356- | IC/X-357- | IC/X-358- |
| IC/X-359- | IC/X-360- | IC/X-361- | IC/X-362- | IC/X-363- | IC/X-364- |
| IC/X-365- | IC/X-366- | IC/X-367- | IC/X-368- | IC/X-369- | IC/X-370- |
| IC/X-371- | IC/X-372- | IC/X-373- | IC/X-374- | IC/X-375- | IC/X-376- |
| IC/X-377- | IC/X-378- | IC/X-379- | IC/X-380- | IC/X-381- | IC/X-382- |
| IC/X-383- | IC/X-384- | IC/X-385- | IC/X-386- | IC/X-387- | IC/X-388- |
| IC/X-389- | IC/X-390- | IC/X-391- | IC/X-392- | IC/X-393- | IC/X-394- |
| IC/X-395- | IC/X-396- | IC/X-397- | IC/X-398- | IC/X-399- | IC/X-400- |
| IC/X-401- | IC/X-402- | IC/X-403- | IC/XA04- | IC/X-405- | IC/X-406- |
| IC/X-407- | IC/X-408- | IC/X-409- | IC/X-410- | IC/X-411- | IC/X-412- |
| IC/X-413- | IC/X-414- | IC/X-415- | IC/X-416- | IC/X-417- | IC/X-418- |
| ID/X-1- | ID/X-2- | ID/X-3- | ID/X-4- | ID/X-5- | ID/X-6- |
| ID/X-7- | ID/X-8- | ID/X-9- | ID/X-10- | ID/X-11- | ID/X-12- |
| ID/X-13- | ID/X-14- | ID/X-15- | ID/X-16- | ID/X-17- | ID/X-18- |
| ID/X-19- | ID/X-20- | ID/X-21- | ID/X-22- | ID/X-23- | ID/X-24- |
| ID/X-25- | ID/X-26- | ID/X-27- | ID/X-28- | ID/X-29- | ID/X-30- |
| ID/X-31- | ID/X-32- | ID/X-33- | ID/X-34- | ID/X-35- | ID/X-36- |
| ID/X-37- | ID/X-38- | ID/X-39- | ID/X-40- | ID/X-41- | 1D/X-42- |
| ID/X-43- | ID/X-44- | ID/X-45- | ID/X-46- | ID/X47- | ID/X-48- |
| ID/X-49- | ID/X-50- | ID/X-51- | ID/X-52- | ID/X-53- | ID/X-54- |
| ID/X-55- | ID/X-56- | ID/X-57- | ID/X-58- | ID/X-59- | ID/X-60- |
| ID/X-61- | ID/X-62- | ID/X-63- | ID/X-64- | ID/X-65- | ID/X-66- |
| ID/X-67- | ID/X-68- | ID/X-69- | ID/X-70- | ID/X-71- | ID/X-72- |
| ID/X-73- | ID/X-74- | ID/X-75- | ID/X-76- | ID/X-77- | ID/X-78- |
| ID/X-79- | ID/X-80- | ID/X-81- | ID/X-82- | ID/X-83- | ID/X-84- |
| ID/X-85- | ID/X-86- | ID/X-87- | ID/X-88- | ID/X-89- | ID/X-90- |
| ID/X-91- | ID/X-92- | ID/X-93- | ID/X-94- | ID/X-95- | ID/X-96- |
| ID/X-97- | ID/X-98- | ID/X-99- | ID/X-100- | ID/X-101- | ID/X-102- |
| ID/X-103- | ID/X-104- | ID/X-105- | ID/X-106- | ID/X-107- | ID/X-108- |
| ID/X-109- | ID/X-110- | ID/X-111- | ID/X-112- | ID/X-113- | ID/X-114- |
| ID/X-115- | ID/X-116- | ID/X-117- | ID/X-118- | ID/X-119- | ID/X-120- |
| ID/X-121- | ID/X-122- | ID/X-123- | ID/X-124- | ID/X-125- | ID/X-126- |
| ID/X-127- | ID/X-128- | ID/X-129- | ID/X-130- | ID/X-131- | ID/X-132- |
| ID/X-133- | ID/X-134- | ID/X-135- | ID/X-136- | ID/X-137- | ID/X-138- |
| ID/X-139- | ID/X-140- | ID/X-141- | ID/X-142- | ID/X-143- | ID/X-144- |
| ID/X-145- | ID/X-146- | ID/X-147- | ID/X-148- | ID/X-149- | ID/X-150- |
| ID/X-151- | ID/X-152- | ID/X-153- | ID/X-154- | ID/X-155- | ID/X-156- |
| ID/X-157- | ID/X-158- | ID/X-159- | ID/X-160- | ID/X-161- | ID/X-162- |
| ID/X-163- | ID/X-164- | ID/X-165- | ID/X-166- | ID/X-167- | ID/X-168- |
| ID/X-169- | ID/X-170- | ID/X-171- | ID/X-172- | | |
| ID/X-173- | ID/X-174- | ID/X-175- | ID/X-176- | ID/X-177- | ID/X-178- |
| ID/X-179- | ID/X-180- | ID/X-181- | ID/X-182- | ID/X-183- | ID/X-184- |
| ID/X-185- | ID/X-186- | ID/X-187- | ID/X-188- | ID/X-189- | ID/X-190- |
| ID/X-191- | ID/X-192- | ID/X-193- | ID/X-194- | ID/X-195- | ID/X-196- |
| ID/X-197- | ID/X-198- | ID/X-199- | ID/X-200- | ID/X-201- | ID/X-202- |
| ID/X-203- | ID/X-204- | ID/X-205- | ID/X-206- | ID/X-207- | ID/X-208- |
| ID/X-209- | ID/X-210- | ID/X-211- | ID/X-212- | ID/X-213- | ID/X-214- |
| ID/X-215- | ID/X-216- | ID/X-217- | ID/X-218- | ID/X-219- | ID/X-220- |
| ID/X-221- | ID/X-222- | ID/X-223- | ID/X-224- | ID/X-225- | ID/X-226- |
| ID/X-227- | ID/X-228- | ID/X-229- | ID/X-230- | ID/X-231- | ID/X-232- |
| ID/X-233- | ID/X-234- | ID/X-235- | ID/X-236- | ID/X-237- | ID/X-238- |
| ID/X-239- | ID/X-240- | ID/X-241- | ID/X-242- | ID/X-243- | ID/X-244- |
| ID/X-245- | ID/X-246- | ID/X-247- | ID/X-248- | ID/X-249- | ID/X-250- |
| ID/X-251- | ID/X-252- | ID/X-253- | ID/X-254- | ID/X-255- | ID/X-256- |
| ID/X-257- | ID/X-258- | ID/X-259- | ID/X-260- | ID/X-261- | ID/X-262- |
| ID/X-263- | ID/X-264- | ID/X-265- | ID/X-266- | ID/X-267- | ID/X-268- |
| ID/X-269- | ID/X-270- | ID/X-271- | ID/X-272- | ID/X-273- | ID/X-274- |
| ID/X-275- | ID/X-276- | ID/X-277- | ID/X-278- | ID/X-279- | ID/X-280- |
| ID/X-281- | ID/X-282- | ID/X-283- | ID/X-284- | ID/X-285- | ID/X-286- |
| ID/X-287- | ID/X-288- | ID/X-289- | ID/X-290- | ID/X-291- | ID/X-292- |
| ID/X-293- | ID/X-294- | ID/X-295- | ID/X-296- | ID/X-297- | ID/X-298- |
| ID/X-299- | ID/X-300- | ID/X-301- | ID/X-302- | ID/X-303- | ID/X-304- |
| ID/X-305- | ID/X-306- | ID/X-307- | ID/X-308- | ID/X-309- | ID/X-310- |
| ID/X-311- | ID/X-312- | ID/X-313- | ID/X-314- | ID/X-315- | ID/X-316- |
| ID/X-317- | ID/X-318- | ID/X-319- | ID/X-320- | ID/X-321- | ID/X-322- |
| ID/X-323- | ID/X-324- | ID/X-325- | ID/X-326- | ID/X-327- | ID/X-328- |
| ID/X-329- | ID/X-330- | ID/X-331- | ID/X-332- | ID/X-333- | ID/X-334- |
| ID/X-335- | ID/X-336- | ID/X-337- | ID/X-338- | ID/X-339- | ID/X-340- |
| ID/X-341- | ID/X-342- | ID/X-343- | ID/X-344- | ID/X-345- | ID/X-346- |
| ID/X-347- | ID/X-348- | ID/X-349- | ID/X-350- | ID/X-351- | ID/X-352- |
| ID/X-353- | ID/X-354- | ID/X-355- | ID/X-356- | ID/X-357- | ID/X-358- |
| ID/X-359- | ID/X-360- | ID/X-361- | ID/X-362- | ID/X-363- | ID/X-364- |
| ID/X-365- | ID/X-366- | ID/X-367- | ID/X-368- | ID/X-369- | ID/X-370- |
| ID/X-371- | ID/X-372- | ID/X-373- | ID/X-374- | ID/X-375- | ID/X-376- |
| ID/X-377- | ID/X-378- | ID/X-379- | ID/X-380- | ID/X-381- | ID/X-382- |
| ID/X-383- | ID/X-384- | ID/X-385- | ID/X-386- | ID/X-387- | ID/X-388- |
| ID/X-389- | ID/X-390- | ID/X-391- | ID/X-392- | ID/X-393- | ID/X-394- |
| ID/X-395- | ID/X-396- | ID/X-397- | ID/X-398- | ID/X-399- | ID/X-400- |
| ID/X-401- | ID/X-402- | ID/X-403- | ID/X-404- | ID/X-405- | ID/X-406- |
| ID/X-407- | ID/X-408- | ID/X-409- | ID/X-410- | ID/X-411- | ID/X-412- |
| ID/X-413- | ID/X-414- | ID/X-415- | ID/X-416- | ID/X-417- | ID/X-418- |

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds described herein associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.001 to about 1 g, more usually about 1 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

A formulation may be prepared as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

| A formulation may be prepared as follows: | |
|---|---|
| Ingredient | Quantity |
| Active Ingredient | 5.0 mg |
| Corn Oil | 1.0 mL |

FORMULATION EXAMPLE 10

| A topical formulation may be prepared as follows: | |
|---|---|
| Ingredient | Quantity |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Other suitable formulations for use in the present invention can be found in *Remington's Pharmaceutical Sciences*, Mace Publishing Company, Philadelphia, Pa., 17th ed. (1985).

Utility

The multibinding compounds of this invention inhibit 3-hydroxy-3-methylglutaryl coenzyme A (HMG-CoA) reductase, the rate limiting enzyme in cholesterol biosynthesis. Accordingly, the multibinding compounds of this invention and pharmaceutical compositions comprising such compounds are useful in the treatment and prevention of hypercholesterolemia, hyperlipidemia, atherosclerosis and the like.

When used in treating or ameliorating such conditions, the compounds of this invention are typically delivered to a patient in need of such treatment by a pharmaceutical composition comprising a pharmaceutically acceptable diluent and an effective amount of at least one compound of this invention. The amount of compound administered to the patient will vary depending upon what compound and/or composition is being administered, the purpose of the administration, such as prophylaxis or therapy, the state of the patient, the manner of administration, and the like. In therapeutic applications, compositions are administered to a patient already suffering from, for example, hypercholesterolemia in an amount sufficient to at least partially reduce serum cholesterol levels. Amounts effective for this use will depend on the judgment of the attending clinician depending upon factors such as the degree or severity of the hypercholesterolemia in the patient, the age, weight and general condition of the patient, and the like. The pharmaceutical compositions of this invention may contain more than one compound of the present invention. As noted above, the compounds administered to a patient are in the form of pharmaceutical compositions described above which can be administered by a variety of routes including oral, rectal, transdermal, subcutaneous, intravenous, intramuscular, etc. These compounds are effective as both injectable and oral deliverable pharmaceutical compositions. Such compositions are prepared in a manner well known in the pharmaceutical art and comprise at least one active compound.

The multibinding compounds of this invention can also be administered in the form of pro-drugs, i.e., as derivatives which are converted into a biologically active compound in vivo. Such pro-drugs will typically include compounds in which, for example, a carboxylic acid group, a hydroxyl group or a thiol group is converted to a biologically liable group, such as an ester, lactone or thioester group which will hydrolyze in vivo to reinstate the respective group. In particular, the compounds of this invention in which $A^1$ is in the lactone form are believed to be pro-drugs, i.e., the lactone is believed to be hydrolyzed to the active dihydroxy acid form in the liver.

The following synthetic and biological examples are offered to illustrate this invention and are not to be construed in any way as limiting the scope of this invention. These examples are illustrated in FIGS. 12–17 and the compound numbers employed in these examples refer to compounds illustrated in the figures. Unless otherwise stated, all temperatures are in degrees Celsius.

EXAMPLES

In the examples below, the following abbreviations have the following meanings. If an abbreviation is not defined, it has its generally accepted meaning.

| | | |
|---|---|---|
| Å | = | Angstroms |
| cm | = | centimeter |
| DCC | = | dicyclohexyl carbodiimide |
| DMF | = | N,N-dimethylformamide |
| DMSO | = | dimethylsulfoxide |
| EDTA | = | ethylenediaminetetraacetic acid |
| g | = | gram |
| HBSS | = | Hank's Balanced Salt Solution |
| HPLC | = | high performance liquid chromatography |
| MEM | = | minimal essential medium |
| mg | = | milligram |
| MIC | = | minimum inhibitory concentration |
| min | = | minute |
| mL | = | milliliter |
| mm | = | millimeter |
| mmol | = | millimol |
| N | = | normal |
| NADP | = | nicotinamide adenine dinucleotide phosphate |
| NADPH | = | nicotinamide adenine dinucleotide phosphate, reduced form |
| THF | = | tetrahydrofuran |
| μL | = | microliters |
| μm | = | microns |

In the following example, Examples A–D illustrate the synthesis of intermediates useful in preparing compounds of this invention; and Example 1–10 illustrate the preparation of compounds of formula I.

Example A

Synthesis of (4R-cis)-1,1-Dimethylethyl-6-[2-[(4-fluorophenyl)-5-(1-methylethyl)-3-phenyl-4-[(4-hydroxyphenylamino)carbonyl]-1H-pyrrol-1-yl]ethyl]-2,2-dimethyl-1,3-dioxane-4-acetate (Compound 10, R=4-OH)

(4R-cis)-1,1-Dimethylethyl-6-[2-[(4-fluorophenyl)-5-(1-methylethyl)-3-phenyl-4-[(4-benzyloxyphenyl)carbonyl]-1H-pyrrol-1-yl]ethyl]-2,2-dimethyl-1,3-dioxane-4-acetate, 9, (R=4-OBn) (the preparation of which is described in U.S. Pat. No. 5,383,929) (0.5 mmol) is dissolved in EtOAc (30 mL) and 5% Pd/C (25 mg) is added. The reaction is stirred in a hydrogenation apparatus until tlc monitoring indicates that the reaction is complete. The mixture is then filtered and added to water. The aqueous solution is extracted with $CH_2Cl_2$, and the extract is dried and evaporated. The residue is chromatographed to afford the title compound, 10, (R=4-OH).

In a similar manner, the compounds (4R-cis)-1,1-dimethylethyl-6-[2-[(4-fluorophenyl)-5-(1-methylethyl)-3-phenyl-4-[(2- or 3-benzyloxyphenylamino)carbonyl]-1H-pyrrol-1-yl]ethyl]-2,2-dimethyl- 1,3-dioxane-4-acetate (9, R=2-OBn or R=3-OBn) (the preparations of which are described in U.S. Pat. No. 5,393,929) are converted into compound 10 (R=2-OH and R=3-OH respectively) as shown in FIG. 12.

Example B

Synthesis of (4R-cis)-1,1-Dimethylethyl-6-[2-[(4-fluorophenyl)-5-(1-methylethyl)-3-phenyl-4-[(4-aminophenylamino)carbonyl]-1H-pyrrol-1-yl]ethyl]-2,2-dimethyl-1,3-dioxane-4-acetate (Compound 10, R=4-$NH_2$)

Step A—Methyl isobutyryl acetate (20 mmol), 4-benzyloxycarbonylaminoaniline (20 mmol) and ethylenediamine (1 mmol) are refluxed in xylene (100 mL) using a Dean-Stark trap to remove water. When the reaction is complete by tlc, the solution is cooled and benzaldehyde (20 mmol) and pyridine (0.2 mL) are added. The mixture is then heated to reflux until the reaction is complete by tlc. The solvent is removed under vacuum and the product, N-(4-benzyloxycarbonylamino)phenyl)-4-methyl-3-oxo-2-(phenyhmethylene)pentanamide, 5, (R=4-NHCbz) is obtained by chromatography.

In a similar manner, by employing 2- or 3-benzyloxycarbonylaminoaniline in place of 4-benzyloxycarbonylaminoaniline, compound 5 (R=2- or 3-NHCbz, respectively) are obtained.

Step B—N-(4-benzyloxycarbonylamino)phenyl)-4-methyl-3-oxo-2-(phenylmethylene)pentanamide (10 mmol), 3-ethyl-5-(2-hydroxyethyl)-4-methylthiazolium bromide (3 mmol), 4-fluorobenzaldehyde (10 mmol) and triethylamine (10 mmol) are heated at reflux in EtOH (150 mL). The progress of the reaction is monitored by tlc. When the reaction is complete, the mixture is cooled and added to water. The aqueous solution is extracted with EtOAc, and the extract is dried and evaporated. The residue is chromatographed to afford the product N-(4-benzyloxycarbonylaminophenyl)-4-methyl-3-oxo-2-[1-phenyl-2-(4-fluorophenyl)-2-oxoethyl]pentanamide 7 (R=4-NHCbz).

In a similar manner, by employing N-(2- or 3-benzyloxycarbonylamino)-phenyl)-4-methyl-3-oxo-2-(phenylmethylene)pentanamide in place of N-(4-benzyloxycarbonylamino)phenyl)-4-methyl-3-oxo-2-(phenylmethylene)-pentanamide in the above reaction, compound 7 (R=2- or 3-NHCbz, respectively) are obtained.

Step C—N-(4-Benzyloxycarbonylaminophenyl)-4-methyl-3-oxo-2-[1-phenyl-2-(4-fluorophenyl)-2-oxoethyl]pentanamide (5 mmol), (4R-cis)-1,1-dimethylethyl-6-(2-aminoethyl)-2,2-dimethyl-1,3-dioxane-4-acetate (8), prepared as described in U.S. Pat. No. 5,216,174, (5 mmol) and pivalic acid (5 mmol) are heated at reflux in 4:1:1 heptane/toluene/THF (30 mL). The progress of the reaction is monitored by tlc. When the reaction is complete, the mixture is cooled, added to water, and extracted with EtOAc. The extract is dried and evaporated, and the residue is chromatographed to afford (4R-cis)-1,1-dimethylethyl-6-[2-[(4-fluorophenyl)-5-(1-methylethyl)-3-phenyl-4-[(4-benzyloxycarbonyl-arninophenylamino)carbonyl]-1H-pyrrol-1-yl]ethyl]-2,2-dimethyl-1,3-dioxane-4-acetate, 9 (R=4-NHCbz).

In a similar manner, by employing 4-methyl-3-oxo-N-(2- or 3-benzyloxycarbonylaminophenyl)-2-[1-phenyl-2-(4-fluorophenyl)-2-oxoethyl]pentanamide in place of 4-methyl-3-oxo-N-(4-benzyloxycarbonylaminophenyl)-2-[1-phenyl-2-(4-fluorophenyl)-2-oxoethyl]pentanamide, compound 9 (R=2- or 3-NHCbz, respectively) are obtained.

Step D—(4R-cis)-1,1-Dimethylethyl-6-[2-[(4-fluorophenyl)-5-(1-methylethyl)-3-phenyl-4-[(4-benzyloxycarbonylaminophenylamino)carbonyl]-1H-pyrrol- 1-yl]ethyl]-2,2-dimethyl-1,3-dioxane-4-acetate (1 mmol) is dissolved in EtOH (20 mL), and 10% Pd/C (50 mg) and ammonium formate (2 mmol) are added. The reaction is stirred and monitored by tlc. When the reaction is complete, the solution is filtered and the residue is chromatographed to afford the title compound, 10 (R=4-$NH_2$).

In a similar manner, by employing (4R-cis)-1,1-dimethylethyl-6-[2-[(4-fluorophenyl)-5-(1-methylethyl)-3-phenyl-4-[(2- or 3-benzyloxycarbonylaminophenylarnino)carbonyl]-1H-pyrrol-1-yl]ethyl]-2,2-dimethyl-1,3-dioxane-4-acetate in place of (4R-cis)-1,1-dimethylethyl-6-[2-[(4-fluorophenyl)-5-(1-methylethyl)-3-phenyl-4-[(4-benzyloxycarbonylaminophenylamino)carbonyl]-1H-pyrrol-1-yl]ethyl]-2,2-dimethyl-1,3-dioxane-4-acetate in the above procedure, the products (4R-cis)-1,1-dimethylethyl-6-[2-[(4-fluorophenyl)-5-(1-methylethyl)-3-phenyl-4-[(2- or 3-aminophenylamino)carbonyl]-1H-pyrrol-1-yl]ethyl]-2,2-dimethyl-1,3-dioxane-4-acetate, 10 (R=2- or 3-$NH_2$, respectively) are obtained.

Example C

Syntheis of (4R-cis)-1,1-Dimethylethyl-6-[2-[(4-fluorophenyl)-5-(1-methylethyl)-3-(4-hydroxyphenyl-4-(phenylaminocarbonyl)-1H-pyrrol-1-yl]ethyl]-2,2-dimethyl-1,3-dioxane-4-acetate (Compound 16, R=4-OH)

Step A—A solution of 4-methyl-N-phenyl-3-oxopentanamide, 12, (5 mmol), 4-benzyloxybenzaldehyde (5 mmol) and pyridine (1 mL) in xylene (100 mL) is heated at reflux, with azeotropic removal of water. The progress of the reaction is monitored by tlc. When the reaction is complete, the solvent is removed under reduced pressure, and the residue is chromatographed to afford 2-(4-benzyloxyphenylmethylene)-4-methyl-3-oxopentanamide, 13, (R=4-benzyloxy).

In a similar manner, the use of 2- or 3-benzyloxybenzaldehyde in the above procedure affords, respectively, compound 13 (R=2- or 3-benzyloxy).

Additonally, the use of 2- 3- or 4-benzyloxycarbonylaminobenzaldehyde in the above procedure affords, respectively, compound 13 (R=2- 3- or 4-benzyloxycarbonylamino).

Step B—A solution of 3-ethyl-5-(2-hydroxyethyl)-4-methylthiazolium bromide (2 mmol), 2-(4-benzyloxyphenylmethylene)-4-methyl-3-oxopentanamide (8 mmol), 4-fluorobenzaldehyde (8 mmol) and triethylamine (1 mL) in EtOH (100 mL) is heated at reflux. The progress of the reaction is monitored by tlc. When the reaction is complete, the solvent is removed under reduced pressure and the residue is dissolved in EtOAc. The solution is washed with dilute HCl, then dried and evaporated. The residue is chromatographed to afford 2-[1-(4-benzyloxyphenyl)-2-(4-fluorophenyl)-2-oxoethyl]-4-methyl-3-oxo-N-phenylpentanamide, 14 (R=4-benzyloxy).

In a similar manner, the use of the 2- or 3-benzyloxy-substituted compounds 13, in the above procedure affords, respectively, compound 14 (R is 2- or 3-benzyloxy). Additionally, the use of the 2-, 3- or 4-benzyloxycarbonlyamino-substituted compound 13 affords, respectively, compound 14 (R is 2- or 4-benzyloxycarbonylamino).

Step C—A mixture of (4R-cis)-1,1-dimethylethyl-6-(2-aminoethyl)-2,2-dimethyl-1,3-dioxane-4-acetate, 8, (2 mmol) and 2-[1-(4-benzyloxyphenyl)-2-(4-fluorophenyl)-2-oxoethyl]-4-methyl-3-oxo-N-phenylpentanamide, 14 (R=4-benzyloxy) (1 mmol) and pivalic acid (1 mmol) in 4:1:1 heptane/toluene/THF (40 mL) is heated at reflux. The reaction is monitored by tlc. When the reaction is complete, the solution is washed with aqueous $NaHCO_3$, then dried and evaporated. The residue is chromatographed to afford (4R-cis)-1,1-dimethylethyl-6-[2-[3-( 4-benzyloxyphenyl)-2-(4-fluorophenyl)-5-(1-methylethyl)-)-4-(phenylaininocarbonyl)-1H-pyrrol-1-yl]ethyl]-2,2-dimethyl-1,3-dioxane-4-acetate, 15 (R=4-benzyloxy).

In a similar manner, the use of the 2- or 3-benzyloxy-substituted compound 14 (R=2- or 3-benzyloxy) affords, respectively, compound 15 (R=2- or 3-benzyloxy). Additionally, the use of the 2-, 3- or 4-benzyloxycarbonylamino-substituted compound 14 affords, respectively, compound 15 (R=2- 3- or 4-benzyloxycarbonylamino).

Step D—Compound 15 (R=4-benzyloxy) (0.5 mmol) is dissolved in EtOAc (30 mL) and 5% Pd/C (25 mg) is added. The reaction is stirred in a hydrogenation apparatus until tlc monitoring indicates that the reaction is complete. The mixture is filtered and added to water. The aqueous solution is extracted with $CH_2Cl_2$, and the extract is dried and evaporated. The residue is chromatographed to afford (4R-15 cis)-1,1-dimethylethyl-6-[2-[2-(4-fluorophenyl)-3-(4-hydroxyphenyl)-5-(1-methylethyl)-)-4-(phenylaminocarbonyl)-1H-pyrrol-1-yl]ethyl]-2,2-dimethyl-1,3-dioxane-4-acetate, 16 (R=4-OH).

In a similar manner, the use of compound 15 (R=2- or 3-benzyloxy) affords the products (4R-cis)-1,1-dimethylethyl-6-[2-[2-(4-fluorophenyl)-3-(2- or 3-hydroxyphenyl)-5-(1-methylethyl)-)-4-(phenylaminocarbonyl)-1H-pyrrol-1-yl]ethyl]-2,2-dimethyl-1,3-dioxane-4-acetate, 16 (R=2- or 3-OH).

Alternatively, (4R-cis)-1,1-Dimethylethyl-6-[2-[3-(4-benzyloxycarbonylaminophenyl)-2-(4-fluorophenyl)-5-(1-methylethyl)-)-4-(phenylaminocarbonyl)-1H-pyrrol-1-yl]ethyl]-2,2-dimethyl-1,3-dioxane-4-acetate, 15 (R=4-benzyloxycarbonylamino) (1 mmol) is dissolved in EtOH (20 mL), and 10% Pd/C (50 mg) and ammonium formate (2 mmol) are added. The mixture is stirred and the reaction is monitored by tlc. When the reaction is complete, the solution is filtered and the residue is chromatographed to afford (4R-cis)- 1,1-dimethylethyl-6-[2-[3-(4-aminophenyl)-2-(4-fluorophenyl)-5-(1-methylethyl)-)-4-(phenylaminocarbonyl)-1H-pyrrol-1-yl]ethyl]-2,2-dimethyl-1,3-dioxane-4-acetate, 16 (R=4-$NH_2$).

In a similar manner, the use of compound 15 (R=2- or 3-benzyloxycarbonylamino) affords (4R-cis)-1,1-dimethylethyl-6-[2-[2-(4-fluorophenyl)-3-(2- or 3-aminophenyl)-5-(1-methylethyl)-)-4-(phenylaminocarbonyl)-1H-pyrrol-1-yl]ethyl]-2,2-dimethyl-1,3-dioxane-4-acetate, 16 (R=2- or 3-$NH_2$).

Example D

Synthesis of (2R-trans)-5-(4-Fluorophenyl)-2-(1-methylethyl)-4-phenyl-1-[2-(tetrahydro-4-hydroxy-6-oxo-2H-pyran-2-yl)ethyl]-1H-pyrrole-3-carboxylic Acid (Compound 18)

A solution of atorvastatin (prepared as described in U.S. Pat. Nos. 5,397,792 and 5,446,054) (1 mmol) and NaOH (10 mmol) in THF (30 mL) and water (10 mL) is maintained at 50° C. The progress of the reaction is monitored by tlc. When the reaction is complete, the solution is acidified with dilute HCl and extracted with $CH_2Cl_2$. The extract is then dried and evaporated. The residue is dissolved in toluene (50 mL) and the solution is heated at reflux until tlc monitoring shows that formation of the lactone moiety is complete. The solvent is removed under reduced pressure and compound 18 is purified by chromatography.

Example 1

Synthesis of (3R,5R)-1,8-di-[4-[1-[6-carboxy-3,5-dihydroxyhexyl]-5-(4-fluorophenyl)-2-methylethyl)-3-phenylcarbonylamino]-1H-pyrrol-3-yl]phenoxyoctane (Compound 17, X=4-O— and Link=—$(CH_2)_8$—)

Step A—1,8-Di-(p-toluenesulfonyloxy)octane (0.5 mmol) is added to a mixture of compound 16 (R=4-OH) (1 mmol) and $K_2CO_3$ (1 g) in DMF (20 mL). The progress of the reaction is monitored by tlc. When the reaction is complete, the mixture is added to water and extracted with EtOAc. The extract is dried and evaporated and the residue is chromatographed to afford the coupled product, (4R,cis)-1,8-di-[4-[1-[2-[2,2-dimethyl-4-[1,1-dimethylethoxycarbonylmethyl]-1,3-dioxan-6-yl]ethyl]-5-(4-fluorophenyl)-2-(1-methylethyl)-3-phenylcarbonylamino]-1H-pyrrol-3-yl]phenoxyoctane.

Step B—The product from Step A (0.5 mmol) is dissolved in MeOH (10 mL) and 1N HCl (3 mL), and the solution is maintained at room temperature. The reaction is monitored by tlc. When the reaction is complete, the solvents are removed under reduced pressure and the residue is dissolved in 1:1 THF/MeOH (10 mL). To the solution is added 1N NaOH (3 mL). The progress of the reaction is monitored by tlc. When the reaction is complete, the pH is adjusted to 1 by addition of 1N HCl. The solution is then extracted with $CH_2Cl_2$ and the extract is dried and evaporated. The residue is chromatographed to afford compound, 17 (X=O and Link=—$(CH_2)_8$—).

In a similar manner, by employing compounds 16 (R=2- or 3-OH) in place of compound 16 (R=4-OH), the corresponding products (3R,5R)-1,8-di-[2- or 3-[1-[6-carboxy-3,5-dihydroxyhexyl]-5-(4-fluorophenyl)-2-(1-methylethyl)-3- phenylcarbonylamino]-1H-pyrrol-3-yl]phenoxyoctane, 17 (X=2- or 3-O— and Link=—(CH$_2$)$_8$—) are obtained. Other dialkylating agents may also be employed in these reactions.

Example 2

Synthesis of N,N'-Bis-[4-[1-[6-carboxy-3,5-dihydroxyhexyl]-5-(4-fluorophenyl)-2-(1-methylethyl)-3-phenylcarbonylamino]-1H-pyrrole-4-yl]phenyl-(3R,5R) 1,6-hexanediamide (Compound 17, X=4-NH and Link=—(CH)$_4$—)

Step A—(4R-cis)-1,1-Dimethylethyl-6-[2-[3-(4-aminophenyl)-2-(4-fluorophenyl)-5-(1-methylethyl)-)-4-(phenylaminocarbonyl)-1H-pyrrol-1-yl]ethyl]-2,2-dimethyl-1,3-dioxane-4-acetate, 16 (R=4-NH$_2$) (1 mmol), hexane-1,6-dioic acid (0.5 mmol) and dicyclohexylcarbodiimide (1 mmol) are dissolved in CH$_2$Cl$_2$ (20 mL). The progress of the reaction is monitored by tlc. When the reaction is complete, the solution is washed with dilute NaOH, dilute HCl, then dried and evaporated. The residue is chromatographed to afford the linked compound N,N'-bis[4-[1-[2-[2,2-dimethyl-4-[1,1-dimethylethoxycarbonylmethyl]-1,3-dioxan-6-yl]ethyl]-5-(4-fluorophenyl)-2-(1-methylethyl)-3-phenylcarbonylamino]-1H-pyrrol-3-yl]phenyl-(4R, cis)-hexane-1,6 diamide.

Step B—The product from Step A (0.5 mmol) is dissolved in MeOH (10 mL) and 1N HCl (3 mL), and the solution is maintained at room temperature. The reaction is monitored by tlc. When the reaction is complete, the solvents are removed under reduced pressure, and the residue is dissolved in 1:1 THF/MeOH (10 mL). To the solution is added 1N NaOH (3 mL). The progress of the reaction is monitored by tlc. When the reaction is complete, the pH is adjusted to 1 by addition of 1N HCl. The solution is extracted with CH$_2$Cl$_2$ and the extract is dried and evaporated. The residue is chromatographed to afford compound 17 (X=4-NH and Link=—(CH$_2$)$_4$—).

In a similar manner, by employing the compound 16 (X=2- or 3-NH$_2$), the corresponding compound 17 (X=2- or 3-NH— and Link is —(CH)$_4$—) are obtained. Other diacids may also be employed in these reactions.

Example 3

Synthesis of 1,6-Bis{4-[1-(3R,5R)-(6-carboxy-3,5-dihydroxyhex-1-yl)-5-(4-fluorophenyl)-2-isopropyl-4-phenyl-1H-pyrrole-3-carboxamido]phenoxy}hexane (Compound 20, Link=—(CH$_2$)$_4$—)

Step A—A solution of N-(4-hydroxy)phenyl 1-{2-[(4R,6R)-6-tert-butyoxycarbonylmethyl-2,2-dimethyl-1,3-dioxan4-yl]ethyl}-5-(4-fluorophenyl)-2-isopropyl-4-phenyl-1H-pyrrole-3-carboxamide (compound 10a in FIG. 15) (671 mg, 1.0 mmol) and 1,6-dibromohexane (122 mg, 0.5 mmol) in DMF (2 mL) is treated with finely powdered potassium carbonate (276 mg, 2.0 mmol) and the mixture is stirred at 60° C. for 18 hours. Water is added, and the product is extracted into chloroform. The solvent is removed in vacuo to give 1,6-bis{4-[1-{2-[(4R,6R)-6-tert-butyoxycarbonylmethyl-2,2-dimethyl-1,3-dioxan-4-yl]ethyl}-5-(4-fluorophenyl)-2-isopropyl-4-phenyl-1H-pyrrole-3-carboxamidol-phenloxy}hexanle (compound 19 in FIG. 15 where Link=—(CH$_2$)$_4$—).

Step B—Compound 19 is dissolved in methanol (5 mL) and 1N HCl (5 mL) and stirred at room temperature for 18 hours. The reaction mixture is concentrated and treated with THF/MeOH/1 NaOH (10 mL). After 4 hours at room temperature, the reaction is concentrated, water (10 mL) is added, and the solution is washed with ether. The aqueous layer is acidified with 1N HCl, and extracted with ethyl acetate. The organic layer is dried, filtered and concentrated. The residue is purified by reverse-phase HPLC using a gradient of 0.1% TFA/acetonitrile in 0.1% aqueous TFA to give the title compound.

Example 4

Synthesis of 3R,5R-1,17-Di-[4-[1-[6-carboxy-3,5-dihdroxyhexyl]-5-(4-fluorophenyl]-2-(1-methylethyl)-4-phenyl]-1H-pyrrole-3-carbonylamino]phenoxy-3,6,9,12,15-pentaoxaheptadecane (Compound 20, Link=—CH$_2$O[(CH$_2$)$_2$O]$_4$CH$_2$—)

Step A—1,17-Dihydroxy-3,6,9,12,15-pentaoxaheptadecanediol (5 mmol) and p-toluenesulfonyl chloride (10 mmol) are dissolved in pyridine (50 mL). The reaction is monitored by tlc. When the reaction is complete, the solution is added to water and extracted with CH$_2$Cl$_2$. The extract is washed with dilute HCl, then dried and evaporated. The product, 1,17-di-(p-toluenesulfonyloxy)-3,6,9,12,15-pentaoxaheptadecane, is then purified by chromatography.

Step B—1,17-Di-(p-toluenesulfonyloxy)-3,6,9,12,15-hexaoxaheptadecane (0.5 mmol), compound 10 (R=4-OH) (from Example A) (1 mmol) and K$_2$CO$_3$ (2 g) are stirred in DMF (50 mL) at room temperature. The reaction is monitored by tic. When the reaction is complete, the solution is added to water and extracted with CH$_2$Cl$_2$. The extract is dried and evaporated, and the residue is chromatographed to afford (4R-cis) 1,17-di-[4-[1-[2-[2,2-dimethyl-4-[1,1-dimethylethoxycarbonylmethyl]-1,3-dioxan-6-yl]ethyl]-5-(4-fluorophenyl]-2-(1-methylethyl)-4-phenyl]-1H-pyrrole-3-carbonylamino]-phenoxy-3,6,9,12,15-pentaoxaheptadecane, 19 (Link=—CH$_2$O[(CH$_2$)$_2$O]$_4$CH$_2$—).

Step C—Compound 19 (0.2 mmol) is dissolved in MeOH (5 mL) and 1N HCl (5 mL) and maintained at room temperature. The progress of the reaction is monitored by tlc. When the reaction is complete, the solvents are removed under reduced pressure and to the residue is added 1:1 THF/MeOH (10 mL), and then 1N NaOH (3 mL). The progress of the reaction is monitored by tlc. When the reaction is complete, the pH is adjusted to 1 by addition of 1N HCL. The solution is extracted with CH$_2$Cl$_2$ and the extract is dried and evaporated to afford a residue from which the title compound 20 is isolated by chromatography.

In a similar manner, by employing compound 10 (R=2- or 3-hydroxy) in place of the 4-hydroxy starting material above, the 2- and 3-substituted isomers of compound 20, namely 3R, 5R-1,17-di-[2- or 3-[1-[6-carboxy-3,5-dihdroxyhexyl]-5 -(4-fluorophenyl]-2-(1-methylethyl)-4-phenyl]-1H-pyrrole-3-carbonylamino]phenoxy-3,6,9,12,15-pentaoxaheptadecane, are prepared.

Additionally, in a similar manner, by employing compound 16 (R=2-, 3- or 4-hydroxy) in place of the 4-hydroxy starting material 10 above, the corresponding dimers, namely (3R,5R)-1,17-di-[2-, 3- or 4-[1-[6-carboxy-3,5-dihdroxyhexyl]-5-(4-fluorophenyl]-2-(1-methylethyl)-3-phenylcarbonylamino]-1H-pyrrol-4-yl]phenoxy-3,6,9,12,15-pentaoxaheptadecane, are prepared. Other linking groups may also be employed in these reactions.

Example 5

Synthesis of N,N'-Bis{4-[1-(3R,5R)-(6carboxy-3,5-dihydroxyhex-1-yl)-5-(4-fluorophenyl)-2-isopropyl-4-phenyl-1H-pyrrole-3-carboxamido]phenyl}adipamide (Compound 22, Link=—(CH$_2$)$_4$—)

Step A—To a solution of adipoyl dichloride (92 mg, 0.5 mmol) in dichloromethane (5 mL) at 0° C. is added dropwise a solution of N-(4-amino)phenyl 1-{2-[(4R,6R)-6-tert-butyoxycarbonylmethyl-2,2-dimethyl-1,3-dioxan-4-yl]ethyl}-5-(4-fluorophenyl)-2-isopropyl-4-phenyl-1H-pyrrole-3-carboxamide (compound 10b in FIG. 16) (670 mg, 1.0 mmol) and pyridine (87 mg, 1.1 mmol) in dichloromethane (5 mL). After 1 hour at 0° C., the ice bath is removed and the reaction allowed to warm to room temperature and stir for an additional two hours. The solution is washed successively with 1N HCl, saturated aqueous sodium bicarbonate, and brine, then dried and concentrated to give N,N'-bis{4-[1-{2-[(4R,6R)-6-tert-butyoxycarbonylmethyl-2,2-dimethyl-1,3-dioxan-4-yl]ethyl}-5-(4-fluorophenyl)-2-isopropyl-4-phenyl-1H-pyrrole-3-carboxamido]phenyl}adipamide (compound 21 in FIG. 16 where Link=—(CH$_2$)$_4$—).

Step B—The residue is dissolved in methanol (5 mL) and 1N HCl (5 mL) and stirred at ambient temperature 18 hours. The reaction mixture is concentrated and treated with THF/MeOH/1N NaOH (10 mL). After 4 hours at room temperature, the reaction is concentrated, water (10 mL) is added, and the solution washed with ether. The aqueous layer is acidified with 1N HCl, and extracted with ethyl acetate. The organic layer is dried, filtered and concentrated. The residue is purified by reverse-phase HPLC using a gradient of 0.1% TFA/acetonitrile in 0.1% aqueous TFA to give the title compound.

Example 6

Synthesis of N,N'-bis-[4-[1-[6-carboxy-3,5-dihydroxyhexyl]-5-(4-fluorophenyl)-2-(1-methylethyl)-4-phenyl]-1H-pyrrole-3-carbonylamino]phenyl-(3R,5R)-1,16-hexadecanediainide (Compound 22, Link=—(CH$_2$)$_{14}$—)

Step A—Dicyclohexylcarbodiimide (1 mmol) is added to a solution of hexadecane-1,16-dioic acid (0.5 mmol) and (4R-cis)-1,1-dimethylethyl-6-[2-[(4-fluorophenyl)-5-(1-methylethyl)-3-phenyl-4-[(4-aminophenylamino)carbonyl]-1H-pyrrol-1-yl]ethyl]-2,2-dimnethyl-1,3-dioxane-4-acetate, 10b (R=4-NH$_2$) (1 mmol in dry CH$_2$Cl$_2$ (25 mL). When the reaction is complete by tlc, the solution is washed with water and dilute HCl, then dried and evaporated. The residue is chromatographed to afford N,N'-bis-[4-[1-[2-[2,2-dimnethyl-4-[1,1-ditnethylethoxycarbonylmethyl]-1,3-dioxan-6-yl]ethyl]-5-(4-fluorophenyl)-2-(1-methylethyl)-4-phenyl]-1H-pyrrole-3-carbonylamino]phenyl-(3R,5R)-1,16-hexadecanediamide, 21 (Link=—(CH$_2$)$_{14}$—).

Step B—Compound 21 (0.2 mmol) is dissolved in MeOH (5 mL) and 1N HCl (2 mL) and the solution is maintained at room temperature. The progress of the reaction is monitored by tlc. When the reaction is complete, the solvents are removed under reduced pressure and to the residue is added 1:1 THF/MeOH (10 mL) and then 1N NaOH (3 mL). The progress of the reaction is monitored by tlc. When the reaction is complete, the pH is adjusted to 1 by addition of 1N HCl. The solution is extracted with CH$_2$Cl$_2$ and the extract is dried and evaporated to afford the title compound, 22 (Link=—(CH$_2$)$_{14}$—).

In a similar manner, by employing compound 10 (R=2- or 3-amino) in place of 10b above, the corresponding 2- and 3-substituted diamides, namely N,N'-bis-[2- or 3-[1-[6-carboxy-3,5-dihydroxyhexyl]-5-(4-fluorophenyl)-2-(1-methylethyl)-4-phenyl]-1H-pyrrole-3-carbonylamino]phenyl-(3R,5R)-1,16-hexadecanediamide, are obtained.

Addtionally, in a similar manner, by employing compound 16 (R=2- 3- or 4-amino) in place of compound 10 above, the corresponding diamides, namely N,N'-bis-[2-, 3- or 4-[1-[6-carboxy-3,5-dihydroxyhexyl]-5-(4-fluorophenyl)-2-(1-methylethyl)-3-phenylcarbonylamino]-1H-pyrrol-4-yl]phenyl-(3R,5R)-1,16-hexadecanediamide, are obtained. Other diacids may also be employed the these reactions.

Example 7

Synthesis of 1,10-Bis[1-(3R,5R)-(6-carboxy-3,5-dihydroxyhex-1-yl)-5-(4-fluorophenyl)-2-isopropyl-4-phenyl-1H-pyrrole-3-carboxamido]decane (Compound 24, Link=—(CH$_2$)$_{10}$—)

Step A—To a solution of 1-[2-(2R,4R)(tetrahydro-4-hydroxy-6-oxo-2H-pyran-2-yl)ethyl]-5-(4-fluorophenyl)-2-isopropyl-4-phenyl-1H-pyrrole-3-carboxylic acid (compound 18 in FIG. 17) (465 mg, 1.0 mmol) and 1,10-diaminodecane (86 mg, 0.5 mmol) in DMF (100 mL) is added N,N-diisopropylethylamine (258 mg, 2.0 mmol), N-hydroxybenzotriazole (135 mg, 1.0 mmol) and PyBOP (570 mg, 1.1 mmol). The reaction is stirred at room temperature for 2 hours, at which time the solvent is removed in vacuo. The residue is dissolved in ethyl acetate and washed successively with 1N HCl, saturated aqueous sodium bicarbonate, and brine, then dried and concentrated to give 1,10-bis[1-[2-(2R,4R)(tetrahydro 4-hydroxy-6-oxo-2H-pyran-2-yl)ethyl]-5-(4-fluorophenyl)-2-isopropyl-4-phenyl-1H-pyrrole-3-carboxamido]decane (compound 23 in FIG. 17 where Link=—(CH$_2$)$_{10}$—).

Step B—The dimer is treated with THF/MeOH/1N NaOH (10 mL). After 4 hours at room temperature, the reaction is concentrated, water (10 mL) is added, and the solution washed with ether. The aqueous layer is acidified with 1N HCl, and extracted with ethyl acetate. The organic layer is dried, filtered and concentrated. The residue is purified by reverse-phase HPLC using a gradient of 0.1% TFA/acetonitrile in 0.1% aqueous TFA to give the title compound.

Example 10

Synthesis of Compound 24 (Link=—(CH$_2$)$_3$O[(CH$_2$)$_2$O]$_2$[(CH$_2$)$_3$NHCO(CH$_2$)$_2$CO—NH(CH$_2$)$_3$[O(CH$_2$)$_2$]$_2$O(CH$_2$)$_3$—)

Step A—1-Amino-13-benzyloxycarbonylamino-4,7,10-trioxatridecane (20 mmol) is added to a solution of succinoyl chloride (3 mmol) and triethylamine (2 mL) in CH$_2$Cl$_2$ (50 mL), maintaining the temperature at 0° C. with ice cooling. After 4 hours, the solution is added to water and the organic phase is washed with dilute HCl, then dried and evaporated. The residue is chromatographed to afford N,N'-di-(13-benzyloxycarbonylamino-4,7,10-trioxatridecyl)succinamide.

Step B—The product from Step A above (3 mmol) is dissolved in MeOH (5 mL) and THF (5 mL). Ammonium formate (5 mmol) and 5% Pd/C (50 mg) are added and the mixture is stirred at room temperature the reaction is complete by tlc. The solution is then filtered and the filtrate is evaporated. The residue is chromatographed to afford N,N'-di-(1,3-amino-4,7,10-trioxatridecyl)succinamide.

Step C—Compound 18 (1 mmol) is dissolved in $CH_2Cl_2$ (20 mL) and then dicyclohexylcarbodiimide (1 mmol) and N,N'-di-(13-amino-4,7,10-trioxatridecyl)succinamide (0.5 mmol) are added. The reaction is monitored by tlc. When the reaction is complete, the solution is added to water and washed with dilute HCl, then dried and evaporated. The residue is chromatographed to afford the compound 23 (Link=—$(CH_2)_3O[(CH_2)_2O]_2[(CH_2)_3NHCO(CH_2)_2CO$—$NH(CH_2)_3[O(CH_2)_2]_2O(CH_2)_3$—).

Step D—Compound 23 (0.5 mmol) is dissolved in MeOH (20 mL) and water (10 mL), and NaOH (5 mmol) is added. The progress of the reaction is monitored by tlc. When the reaction is complete, the pH is adjusted to 1 by addition of dilute HCl, and the solution is extracted with $CH_2Cl_2$. The extract is dried and evaporated, and the residue is chromatographed to afford compound 24 (Link=—$(CH_2)_3O[(CH_2)_2O]_2[(CH_2)_3NHCO(CH_2)_2CO$—$NH(CH_2)_3[O(CH_2)_2]_2O(CH_2)_3$—). Other linkers may also be employed in the above reactions.

Bioassay Example 1

Rat Hepatic HMG-COA Reductase Inhibition Assay

Rat hepatic HMG-COA reductase activity can be measured using a modification of the method described by Edwards et al., *J. Lipid Res.* 1979, 20, 40–46, the disclosure of which is incorporated herein by reference in its entirety. Rat hepatic microsomes are used as a source of enzyme, and the enzyme activity is determined by measuring the conversion of the $^{14}C$-HMG-CoA substrate to [$^{14}C$]mevalonic acid. Livers are removed from 2–4 cholestyramine-fed, decapitated, Sprague-Dawley rats, and homogenized in phosphate buffer A (potassium phosphate, 0.04 M, pH 7.2; KCl, 0.05 M; sucrose, 0.1 M; EDTA, 0.03 M, aprotinin, 500 KI units/mL). The homogenate is spun at 16000 g for 15 min at 4° C. The supernatant is removed and recentrifuged under the same conditions a second time. The second 16000 g supernatant is spun at 100000 g for 70 min at 4° C. Pelleted microsomes are resuspended in a minimum volume of buffer A (3–5 mL per liver) and homogenized in a glass homogenizer. Dithiothreitol is added (10 mM), and the preparation is aliquoted, quick frozen in acetone/dry ice, and stored at −80° C. The specific activity of a typical microsomal preparation is 0.68 nmol of mevalonic acid/mg of protein per minute. The reductase is assayed in 0.25 mL, which contains the following components at the indicated final concentrations: 0.04 M potassium phosphate, pH 7.2; 0.05 M KCl; 0.10 M sucrose; 0.03 M EDTA; 0.01 M dithiothreitol; 3.5mM NaCl; 1% dimethyl sulfoxide; 50–200 µg of microsomal protein; 100 µM of $^{14}C$-[D,L]-HMG-CoA (0.05 µCi, 30–60 mCi/mmol.); 2.7 mM NADPH. Reaction mixtures are incubated at 37° C. Under conditions described, enzyme activity increases linearly up to 300 µg of microsomal protein per reaction mixture and is linear with respect to incubation time up to 30 min. The standard incubation time chosen for drug studies is 20 min, which results in 12–15% conversion of HMG-COA substrate to the mevalonic acid product. [D,L]HMG-CoA substrate is used at 100 µM. NADPH is used in excess at a level 2.7 times the concentration required to achieve maximum enzyme velocity. Standardized assays for the evaluation of inhibitors are conducted according to the following procedure. Microsomal enzyme is incubated in the presence of NADPH at 37° C. for 15 min. DMSO vehicle with or without test compound is added, and the mixture further incubated for 15 min at 37° C. The enzyme assay is initiated by adding $^{14}C$-HMG-CoA substrate. After 20 min of incubation at 37° C., the reaction is stopped by the addition of 25 µL of 33% KOH. [$^3H$] Mevalonic acid (0.05 µCi) is added, and the reaction mixture allowed to stand at room temperature for 30 min. Fifty microliters of 5 N HCl is added to lactonize the mevalonic acid. Bromophenol blue is added as a pH indicator to monitor an adequate drop in pH. Lactonization is allowed to proceed for 30 minutes at room temperature. Reaction mixtures are layered onto 2 g of AG 1-X8 anion exchange resin (Biorad, formate form), poured in 0.7 cm (i.d.) glass columns, and eluted with 2.5 mL of $H_2O$. The first 0.5 mL is discarded, and the next 2.0 mL is collected and counted for both tritium and carbon-14 in 10.0 mL of Opti-fluor (Packard) scintillation fluid. Results are calculated as nanomoles mevalonic acid produced per 20 min and are corrected to 100% recovery of tritium. Drug effects are expressed as $I_{50}$ values (concentration of drug producing 50% inhibition of enzyme activity) derived from composite dose response data from 2–5 experiments.

Bioassay Example 2

Inhibition of Cholesterol Synthesis in Freshly Isolated Rat Hepatocytes

Inhibitors of HMG-CoA reductase can be evaluated for their ability to inhibit [$^{14}C$] acetate incorporation into cholesterol in freshly isolated rat hepatocyte suspensions using a modification of the methods originally described by Capuzzi et al., *Lipids* 1971, 6, 601–607, the disclosure of which is incorporated herein by reference in its entirety. Sprague-Dawley rats (180–220 g) are anesthetized with Nembutal (50 mg/kg). The abdomen is opened, and the first branch of the portal vein is tied closed. Two closing sutures are placed on the distal section of the portal vein, and the portal vein is canulated between the sutures and the first branching vein. The liver is perfused at a rate of 20 mL/min with prewarmed (37° C.) oxygenated buffer A ((HBSS, Hanks' Balanced Salt Solution) without calcium or magnesium containing 0.05% EDTA) after severing the vena cava to allow drainage of the effluent. The liver is additionally perfused with 200 mL of prewarmed oxygenated buffer B (HBSS containing 0.05% bacterial collagenase). Following perfusion with buffer B, the liver is excised and decapsulated in 50 mL of Waymouth's medium, allowing free cells to disperse into the medium. Hepatocytes are isolated either by low-speed centrifugation for 3 min at 50 g at room temperature or by unit gravity sedimentation at 4° C. for 30–45 min. Pelleted hepatocytes are washed once in Waymouth's medium, counted, and assayed for viability by trypan blue exclusion. These hepatocyte enriched cell suspensions routinely show 70–90% viability. Hepatocytes are resuspended at $5\times10^6$ cells per 2.0 mL in incubation medium (IM) [0.02 M Tris-HCl (pH 7.4), 0.1 M KCl, 0.33 mM $MgCl_2$, 0.01 mM $MnCl_2$, 0.001 mM sodium succinate, 0.003 mM Coenzyme A, 0.33 mM sodium citrate, 0.67 mM nicotinamide, 0.23 mM NADP, 1.7 mM glucose-6-phosphate]. Test compounds are routinely dissolved in $H_2O$, DMSO, or DMSO-$H_2O$ (1:3) and added to the IM. Final DMSO concentration in the IM is ≦1.0% and has no significant effect on cholesterol synthesis. Incubation is initiated by adding [$^{14}C$] acetate (58 mCi/mmol, 2 µCi/mL) and placing the cell suspensions (2.0 mL) in 35-mm tissue culture dishes at 37° C. for 2.0 h. Following incubation, cell suspensions are transferred to glass centrifuge tubes and spun at 50 g for 3 min at room temperature. Cell pellets are resuspended and lysed in 1.0 mL of $H_2O$. Lipids are extracted essentially as described in Bligh et al., *Can. J. Biochem. Physiol.* 1959, 37, 911–917, the disclosure of which is incorporated herein by reference in its entirety. Following extraction, the lower organic phase is removed and dried under a stream of nitrogen and the residue resuspended in 100 μL $CHCl_3$-MeOH (2:1). The total sample is spotted on silica gel (LK6D) thin-layer plates and developed in $CH_2Cl_2$-acetone (60:1). Plates are scanned and counted using a BioScan automated scanning system. Radiolabel in the cholesterol peak ($R_f$ 0.28) is determined and expressed as total counts per peak and as a percent of the label in the total lipid extract. Cholesterol peaks in control cultures routinely contain 5000–20000 dpm, and are approximately 30% of the label present in the total lipid extract. Drug effects (percent inhibition of cholesterol synthesis) are determined by comparing the percent of label in the cholesterol peak for control and drug treated cultures. Dose response curves can be constructed from 25 composite data from two or more studies and results are expressed as $I_{50}$ values (concentration of drug which inhibits cholesterol synthesis 50%).

Bioassay Example 3

Inhibition of Cholesterol Synthesis in Human Skin Fibroblasts

Human skin fibroblasts (passage 7–27) are grown in minimal essential medium (MEM, Gibco) containing 10% fetal calf serum. For each experiment, stock cultures are trypsinized to disperse the cell monolayer, counted, and plated in 35-mm tissue culture wells ($5 \times 10^5$ cells/2.0 mL). Cultures are incubated for 18 h at 37° C. in 5% $CO_2$/95% humidified room air. Cholesterol biosynthetic enzymes are induced by removing the serum containing medium, washing the cell monolayers with MEM, adding 1.0 mL of MEM containing 1.0% fatty acid free bovine serum albumin, and incubating the cultures an additional 24 h. Test compounds are dissolved in $H_2O$, DMSO, or DMSO-EM (1:3) (final DMSO concentration in cell cultures $\leq 1.0\%$) and added to the cultures, and the cultures are preincubated for 30 min at 37° C. in 5% $CO_2$/95% humidified room air. Following preincubation with drugs, sodium [1-$^{14}$C] acetate (2.0 μCi/mL, 58 mCi/mmol) is added, and the cultures are reincubated for 4 h. After incubation, the culture medium is removed and the cell monolayer is scraped into 1.0 mL of $H_2O$. Lipids in the lysed cell suspension are extracted as described for hepatocyte suspensions. The organic phase is dried under nitrogen, and the residue is resuspended and analyzed as described for hepatocytes. Cholesterol peaks in control cultures routinely contain 8000–12000 dpm and are approximately 15% of the label present in the total lipid extract.

Inhibition of cholesterol synthesis is determined as described for hepatocytes. Results are expressed as $I_{50}$ values and are derived from composite dose response curves from two or more experiments.

Bioassay Example 4

In Vivo Cholesterol Biosynthesis Inhibition in Rats

The methods used for intravenous (iv) and oral (po) drug testing can be adapted from a procedure originally described in U.S. Pat. No. 4,613,610 and PCT Int. Application WO 86/00367, the disclosures of which are incorporated herein by reference in their entirety. Male Sprague-Dawley rates (200–300 g) are adapted to a reverse light cycle for 7–10 days and fed Purina rat chow (no. 5001) ad libitum. In order to measure cholesterol synthesis, sodium [1-$^{14}$C] acetate (1–3 mCi/mmol) (25 μCi/100 g of body weight) is injected intraperitoneally (ip) 2 h before the mid-dark point in the diurnal cycle. Two hours after the mid-dark point animals are anesthetized ip with ketamineixylazine and bled into EDTA-treated centrifuge tubes from the abdominal aorta. Plasma is obtained by centrifugation at 1100 g for 10 min. One-milliliter plasma samples are aliquoted and either processed directly or frozen at −20° C. For iv testing, the salt forms of test compounds are routinely dissolved in saline and injected iv into the tail vein 5 min before [$^{14}$C] acetate injection. For po testing, drugs are dissolved in saline and given by gavage 30 min before [$^{14}$C] acetate injection. Cholesterol synthesis is measured by determining the level of $^{14}$C-labeled nonsaponifiable lipid present in 1 mL of plasma; the method used is a modification of the method described by Dugan et al., *Arch. Biochem. Biophys.* 1972, 152, 21–27, the disclosure of which is incorporated herein by reference in its entirety. One milliliter physiological saline is added to 1 mL of plasma, followed by the addition of 5.0 mL of 10% KOH in absolute ethanol. Samples are mixed and saponified at 75° C. for 1 h. After cooling, approximately 0.02 μCi (44,000 dpm) [1,2-$^3$H] cholesterol (40–60 Ci/mmol.) is added to each sample. Samples are extracted once with 5 mL of petroleum ether, and the organic phase is backwashed with 5 mL of saline. This extraction procedure typically results in 50–90% recovery of the added [$^3$PH] cholesterol internal standard. The extracts are dried in glass vials, and the residue resuspended in 0.5 mL of $CHCl_3$-MeOH (2:1). Samples are counted for both $^3$H and $^{14}$C in 10 mL of Optifluor scintillation fluid. The [$^3$PH] cholesterol internal standard recovery value from each sample is used to correct each sample to 100% recovery of [$^{14}$C] cholesterol. In early experiments, sample extract residues are redissolved in 100 mL of $CHCl_3$-MeOH (2:1) and chromatographed on silica gel (Whatman LK6D) thin-layer plates using either hexanes-$Et_2O$-HOAc (75:25:1) or $CH_2Cl_2$-acetone (60:1). Using either chromatographic system, greater than 90% of the $^{14}$C-label cochromatographed with authentic cholesterol. Thus, to simplify the method, the TLC step is omitted in subsequent experiments and results are calculated as $^{14}$C-labeled nonsaponifiable plasma lipid values, of which, greater than 90% of the $^{14}$C-label is authentic cholesterol. The percent inhibition of cholesterol synthesis is derived by comparing $^{14}$C-labeled nonsaponifiable plasma lipid values per milliliter of plasma from control and drug-treated animal groups (4–5 rats/group). Percent inhibition is plotted relative to the log drug dose and a linear best fit regression line is determined for each experiment. Mean $ED_{50}$ values (level of drug required to suppress cholesterol synthesis in vivo by 50%) are calculated from two or more experiments.

What is claimed is:

1. A compound of formula I:

wherein each L is a ligand independently selected from the group consisting of:

(a) a ligand of formula IA:

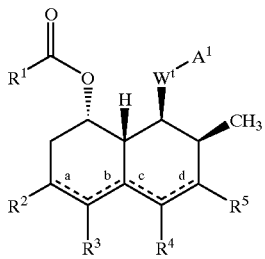

wherein
A¹ is selected from the group consisting of:

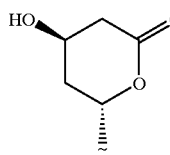 and 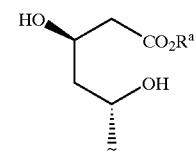

where $R^a$ is selected from the group consisting of hydrogen, lower alkyl and a pharmaceutically-acceptable cation;

$R^1$ is selected from the group consisting of alkyl, substituted alkyl, alkenyl, substituted alkenyl, alkynyl, substituted alkynyl, cycloalkyl, substituted cycloalkyl, alkoxy, substituted alkoxy, aryl, heterocyclic, amino, substituted amino, thioalkoxy, substituted thioalkoxy and thioaryloxy;

$R^2$ is selected from the group consisting of hydrogen, alkyl, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or $R^2$ together with the carbon atom to which it is attached represents a spiro-attached cycloalkyl group;

$R^3$ is selected from the group consisting of hydrogen, alky, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or $R^3$ together with the carbon atom to which it is attached represents a spiro-attached cycloalkyl group;

$R^4$ is selected from the group consisting of hydrogen, alkyl, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or $R^4$ together with the carbon atom to which it is attached represents a spiro-attached cycloalkyl group;

$R^5$ is selected from the group consisting of hydrogen, alkyl, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or $R^2$ together with the carbon atom to which it is attached represents a spiro-attached cycloalkyl group; and a, b, c and d represent optional double bonds, provided that when a or c is a double bond, b is not a double bond; and when b or d is a double bond, c is not a double bond; and $W^1$ is —CH$_2$CH$_2$—;

provided that one of $R^2$, $R^3$, $R^4$ or $R^5$ is a covalent bond linking the ligand to a linker;

(b) a ligand of formula IB:

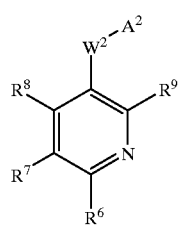

wherein
A² is selected from the group consisting of:

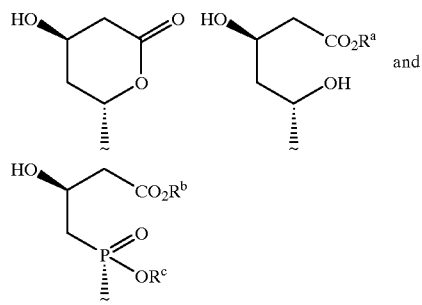

where $R^a$, $R^b$ and $R^c$ are independently selected from the group consisting of hydrogen, lower alkyl and a pharmaceutically-acceptable cation;

$R^6$ is selected from the group consisting of hydrogen, alkyl, substituted alkyl, alkenyl, substituted alkenyl, alkoxy, substituted alkoxy, cycloalkyl, substituted cycloalkyl, cycloalkenyl, substituted cycloalkenyl, aryl, substituted amino, heterocyclic, heteroaryl and a covalent bond attaching the ligand to a linker;

$R^7$ is selected from the group consisting of hydrogen, alkyl, substituted alkyl, alkenyl, substituted alkenyl, alkoxy, substituted alkoxy, cycloalkyl, substituted cycloalkyl, cycloalkenyl, substituted cycloalkenyl, aryl, substituted amino, heterocyclic, heteroaryl, alkoxycarbonyl, cyano, carboxyl and a covalent bond attaching the ligand to a linker;

$R^8$ and $R^9$ are independently selected from the group consisting of hydrogen, alkyl, akenyl, cycloalkyl, cycloalkenyl, aryl, aralkyl and aralkoxy;

$W^2$ is —CH$_2$CH$_2$—, —CH=CH— or —C≡C—;

provided that one of $R^6$ or $R^7$ is a covalent bond linking the ligand to a linker;

(c) a ligand of formula IC:

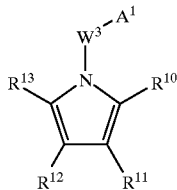

IC wherein
A¹ is as defined above;
R¹⁰ is selected from the group consisting of cycloalkyl and aryl;
one of R¹¹ and R¹² is —C(O)NR¹⁴R¹⁵ where R¹⁴ and R¹⁵ are independently selected from the group consisting of hydrogen, alkyl, aryl and a covalent bond attaching the ligand to a linker; and the other of R¹¹ and R¹² is selected from the group consisting of hydrogen, alkyl, cycloalkyl and a covalent bond attaching the ligand to a linker;
R¹³ is selected from the group consisting of alkyl, cycloalkyl and trifluoromethyl;
W³ is —CH₂—, —CH₂CH₂—, —CH₂CH₂CH₂— or —CH₂CH(CH₃)—;
provided that one of R¹¹, R¹², R¹⁴ or R¹⁵ is a covalent bond linking the ligand to a linker; and (d) a ligand of formula ID:

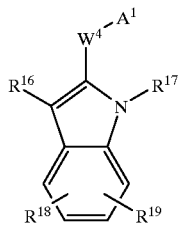

ID wherein
A¹ is as defined above;
one of R¹⁶ and R¹⁷ is aryl; and the other of R¹⁶ and R¹⁷ is selected from the group consisting of alkyl, cycloalkyl and aralkyl;
R¹⁸ and R¹⁹ are independently selected from the group consisting of hydrogen, alkyl, cycloalkyl, alkoxy, halo, aryloxy, aralkoxy and a covalent bond attaching the ligand to a linker; and
W⁴ is —CH₂—, —CH₂CH₂—, —CH₂CH₂CH₂— or —CH=CH—;
provided that one of R¹⁸ or R¹⁹ is a covalent bond linking the ligand to a linker; each X is independently a linker of the formula:

—Xᵃ—Z—(Yᵃ—Z)ₘ—Yᵇ—Z—Xᵃ— wherein
m is an integer of from 0 to 20;
Xᵃ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;
Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;
Yᵃ and Yᵇ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)ₙCR'R"—, —S(O)ₙ—NR'—, —S—S— and a covalent bond; where n is 0, 1 or 2; and
R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;
p is an integer of from 2 to 10;
q is an integer of from 1 to 20, provided that q is less than p;
and further wherein the distance between ligands is at least 10 Å;
and pharmaceutically-acceptable salts thereof.

2. A compound of formula II:

L'—X'—L'  II wherein each L' is a ligand independently selected from the group consisting of:
(a) a ligand of formula IIA:

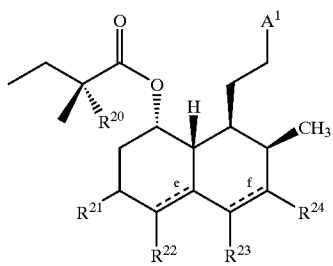

IIA wherein
A¹ is selected from the group consisting of:

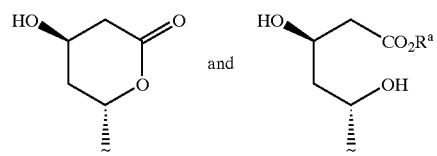

and where Rᵃ is selected from the group consisting of hydrogen, lower alkyl and a pharmaceutically-acceptable cation;
R²¹ is selected from the group consisting of hydrogen, lower alkyl, hydroxy and a covalent bond attaching the ligand to a linker;
R²², R²³ and R²⁴ are independently selected from the group consisting of hydrogen and a covalent bond attaching the ligand to a linker; and
e and f represent optional double bonds;
provided that one of R²¹, R²², R²³ or R²⁴ is a covalent bond linking the ligand to a linker;

(b) a ligand of formula IIB:

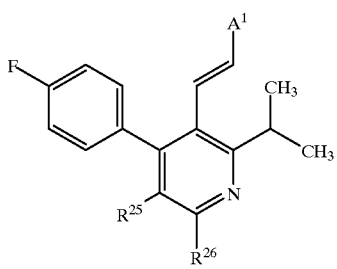

IIB wherein
$A^1$ is as defined above;
$R^{25}$ is selected from the group consisting of hydrogen, alkyl, alkoxyalkyl and a covalent bond attaching the ligand to a linker; and
$R^{26}$ is selected from the group consisting of hydrogen, alkyl, cycloalkyl and a covalent bond attaching the ligand to a linker;
provided that one of $R^{25}$ or $R^{26}$ is a covalent bond linking the ligand to a linker;
(c) a ligand of formula IIC:

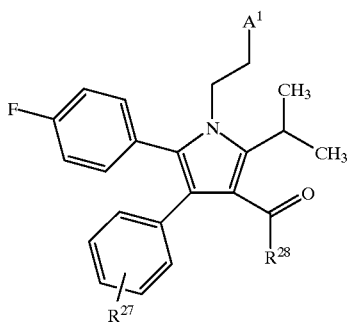

IIC wherein
$A^1$ is as defined above;
$R^{27}$ is selected from the group consisting of hydrogen and a covalent bond attaching the ligand to a linker; and
$R^{28}$ is selected from the group consisting of amino, substituted amino and a covalent bond attaching the ligand to a linker;
provided that one of $R^{27}$ or $R^{28}$ is a covalent bond linking the ligand to a linker; and
(d) a ligand of formula IID:

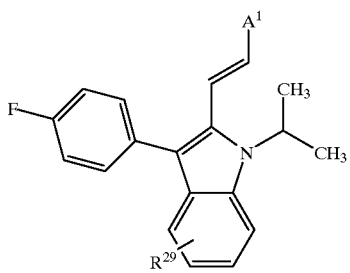

IID wherein $A^1$ is as defined above; and
$R^{29}$ is a covalent bond attaching the ligand to a linker;
X' is a linker of the formula:

—$X^a$—Z—($Y^a$—Z)$_m$—$Y^b$—Z—$X^a$— wherein
m is an integer of from 0 to 20;
$X^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;
Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;
$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)$_n$CR'R"—, —S(O)$_n$—NR'—, —S—S— and a covalent bond; where n is 0, 1 or 2; and
R, R' R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;
and further wherein the distance between ligands is at least 10 Å;
and pharmaceutically-acceptable salts thereof.

3. A compound of formula III:

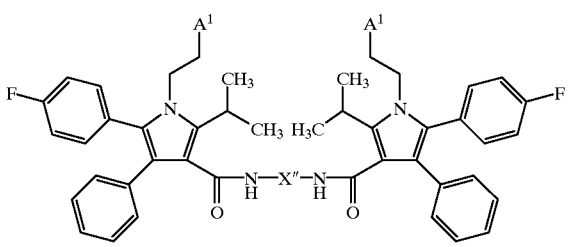

III wherein
each $A^1$ is independently selected from the group consisting of:

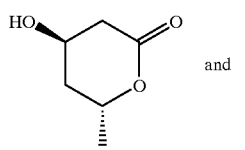

and where $R^a$ is selected from the group consisting of hydrogen, lower alkyl and a pharmaceutically-acceptable cation; and
X" is a linker of the formula:

—$X^a$—Z—($Y^a$—Z)$_m$—$Y^b$—Z—$X^a$—

181 wherein
m is an integer of from 0 to 20;
$X^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;
Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;
$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, -P(O)(OR')—O—, -S(O)$_n$CR'R"—, —S(O)$_n$—NR'—, —S—S— and a covalent bond; where n is 0, 1 or 2; and
R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;
and further wherein the distance between ligands is at least 10 Å;
and pharmaceutically acceptable salts thereof.

4. A compound of formula IV:

IV wherein
each $A^1$ is independently selected from the group consisting of:

where $R^a$ is selected from the group consisting of hydrogen, lower alkyl and a pharmaceutically-acceptable cation; and
X" is a linker of the formula:

—$X^a$—Z—($Y^a$—Z)$_m$—$Y^b$—Z—$X^a$— wherein
m is an integer of from 0 to 20;

182

$X^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;
Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;
$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)$_n$CR'R"—, —S(O)C—NR'—, —S—S— and a covalent bond; where n is 0, 1 or 2; and
R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;
and further wherein the distance between ligands is at least 10 Å;
and pharmaceutically acceptable salts thereof.

5. A pharmaceutical composition comprising a pharmaceutically acceptable carrier and an effective amount of a compound of formula I:

$$(L)_p(X)_q \qquad I$$

wherein each L is a ligand independently selected from the group consisting of:
(a) a ligand of formula IA:

IA wherein
$A^1$ is selected from the group consisting of:

where $R^a$ is selected from the group consisting of hydrogen, lower alkyl and a pharmaceutically-acceptable cation;
$R^1$ is selected from the group consisting of alkyl, substituted alkyl, alkenyl, substituted alkenyl, alkynyl, substituted alkynyl, cycloalkyl, substituted cycloalkyl, alkoxy, substituted alkoxy, aryl, heterocyclic, amino, substituted amino, thioalkoxy, substituted thioalkoxy and thioaryloxy;

R² is selected from the group consisting of hydrogen, alkyl, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or R² together with the carbon atom to which it is attached represents a spiro-attached cycloalkyl group; substituted alkoxy, aryl, heterocyclic, amino, substituted amino, thioalkoxy, substituted thioalkoxy and thioaryloxy;

R² is selected from the group consisting of hydrogen, alkyl, substituted alky, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or R² together with the carbon atom to which it is attached represents a spiro-attached cycloalkyl group;

R³ is selected from the group consisting of hydrogen, alky, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or R³ together with the carbon atom to which it is attached represents a spiro-attached cycloalkyl group;

R⁴ is selected from the group consisting of hydrogen, alkyl, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or R⁴ together with the carbon atom to which it is attached represents a spiro-attached cycloalkyl group;

R⁵ is selected from the group consisting of hydrogen, alkyl, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or R² together with the carbon atom to which it is attached represents a spiro-attached cycloalkyl group; and a, b, c and d represent optional double bonds, provided that when a or c is a double bond, b is not a double bond; and when b or d is a double bond, c is not a double bond; and W¹ is —CH₂CH₂—;

provided that one of R², R³, R⁴ or R⁵ is a covalent bond linking the ligand to a linker;

(b) a ligand of formula IB:

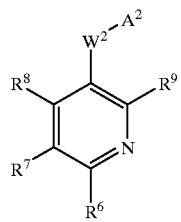

IB wherein

A² is selected from the group consisting of:

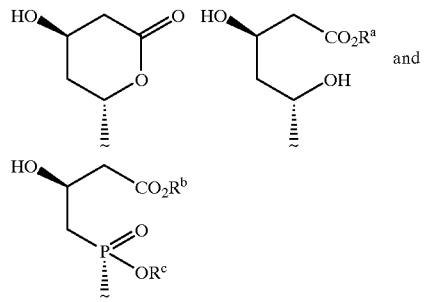

where R$^a$, R$^b$ and R$^c$ are independently selected from the group consisting of hydrogen, lower alkyl and a pharmaceutically-acceptable cation;

R⁶ is selected from the group consisting of hydrogen, alkyl, substituted alkyl, alkenyl, substituted alkenyl, alkoxy, substituted alkoxy, cycloalkyl, substituted cycloalkyl, cycloalkenyl, substituted cycloalkenyl, aryl, substituted amino, heterocyclic, heteroaryl and a covalent bond attaching the ligand to a linker;

R⁷ is selected from the group consisting of hydrogen, alkyl, substituted alkyl, alkenyl, substituted alkenyl, alkoxy, substituted alkoxy, cycloalkyl, substituted cycloalkyl, cycloalkenyl, substituted cycloalkenyl, aryl, substituted amino, heterocyclic, heteroaryl, alkoxycarbonyl, cyano, carboxyl and a covalent bond attaching the ligand to a linker;

R⁸ and R⁹ are independently selected from the group consisting of hydrogen, alkyl, akenyl, cycloalkyl, cycloalkenyl, aryl, aralkyl and aralkoxy;

W² is —CH₂CH₂—, —CH=CH— or —C≡C—;

provided that one of R⁶ or R⁷ is a covalent bond linking the ligand to a linker;

(c) a ligand of formula IC:

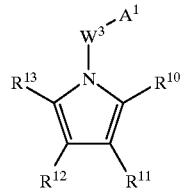

IC wherein

A¹ is as defined above;

R¹⁰ is selected from the group consisting of cycloalkyl and aryl;

one of R¹¹ and R¹² is —C(O)NR¹⁴R¹⁵ where R¹⁴ and R¹⁵ are independently selected from the group consisting of hydrogen, alkyl, aryl and a covalent bond attaching the ligand to a linker; and the other of R¹¹ and R¹² is selected from the group consisting of hydrogen, alkyl, cycloalkyl and a covalent bond attaching the ligand to a linker;

R¹³ is selected from the group consisting of alkyl, cycloalkyl and trifluoromethyl;

W³ is —CH₂—, —CH₂CH₂—, —CH₂CH₂CH₂— or —CH₂CH(CH₃)—;

provided that one of R¹¹, R¹², R¹⁴ or R¹⁵ is a covalent bond linking the ligand to a linker; and (d) a ligand of formula ID:

R³ is selected from the group consisting of hydrogen, alkyl, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or R³ together with the carbon atom to which it is attached represents a spiro-attached cycloalkyl group;

R⁴ is selected from the group consisting of hydrogen, alkyl, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or R⁴ together with the carbon atom to which it is attached represents a spiro-attached cycloalkyl group;

R⁵ is selected from the group consisting of hydrogen, alkyl, substituted alkyl, acyl, acyloxy, alkoxy, alkoxycarbonyl, aminoacyl, aminoacyloxy, aryloxy, carboxyl, hydroxy, keto, thioalkoxy, thioaryloxy, =N—OR$^d$ where R$^d$ is hydrogen or alkyl, and a covalent bond attaching the ligand to a linker; or R² together with the carbon atom to which it is attached represents a spiro-attached cycloalkyl group; and a, b, c and d represent optional double bonds, provided that when a or c is a double bond, b is not a double bond; and when b or d is a double bond, c is not a double bond; and W¹ is —CH₂CH₂—;

provided that one of R², R³, R⁴ or R⁵ is a covalent bond linking the ligand to a linker;

(b) a ligand of formula IB:

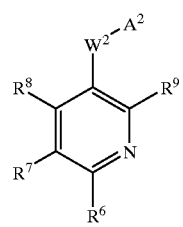

IB wherein
A² is selected from the group consisting of:

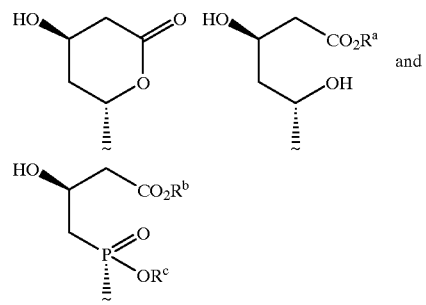

and where R$^a$, R$^b$ and R$^c$ are independently selected from the group consisting of hydrogen, lower alkyl and a pharmaceutically-acceptable cation;

R⁶ is selected from the group consisting of hydrogen, alkyl, substituted alkyl, alkenyl, substituted alkenyl, alkoxy, substituted alkoxy, cycloalkyl, substituted cycloalkyl, cycloalkenyl, substituted cycloalkenyl, aryl, substituted amino, heterocyclic, heteroaryl and a covalent bond attaching the ligand to a linker;

R⁷ is selected from the group consisting of hydrogen, alkyl, substituted alkyl, alkenyl, substituted alkenyl, alkoxy, substituted alkoxy, cycloalkyl, substituted cycloalkyl, cycloalkenyl, substituted cycloalkenyl, aryl, substituted amino, heterocyclic, heteroaryl, alkoxycarbonyl, cyano, carboxyl and a covalent bond attaching the ligand to a linker;

R⁸ and R⁹ are independently selected from the group consisting of hydrogen, alkyl, akenyl, cycloalkyl, cycloalkenyl, aryl, aralkyl and aralkoxy;

W² is —CH₂CH₂—, —CH=CH— or —C≡C—;

provided that one of R⁶ or R⁷ is a covalent bond linking the ligand to a linker;

(c) a ligand of formula IC:

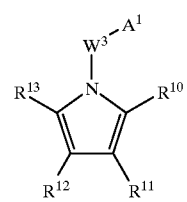

IC wherein
A¹ is as defined above;
R¹⁰ is selected from the group consisting of cycloalkyl and aryl;
one of R¹¹ and R¹² is —C(O)NR¹⁴R¹⁵ where R¹⁴ and R¹⁵ are independently selected from the group consisting of hydrogen, alkyl, aryl and a covalent bond attaching the ligand to a linker; and the other of R¹¹ and R¹² is selected from the group consisting of hydrogen, alkyl, cycloalkyl and a covalent bond attaching the ligand to a linker;
R¹³ is selected from the group consisting of alkyl, cycloalkyl and trifluoromethyl;
W³ is —CH₂—, —CH₂CH₂—, —CH₂CH₂CH₂— or —CH₂CH(CH₃)—;
provided that one of R¹¹, R¹², R¹⁴ or R¹⁵ is a covalent bond linking the ligand to a linker; and (d) a ligand of formula ID:

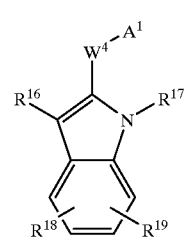

ID wherein
A¹ is as defined above;
one of R¹⁶ and R¹⁷ is aryl; and the other of R¹⁶ and R¹⁷ is selected from the group consisting of alkyl, cycloalkyl and aralkyl;
R¹⁸ and R¹⁹ are independently selected from the group consisting of hydrogen, alkyl, cycloalkyl, alkoxy, halo, aryloxy, aralkoxy and a covalent bond attaching the ligand to a linker; and
W⁴ is —CH₂—, —CH₂CH₂—, —CH₂CH₂CH₂— or —CH=CH—;

provided that one of $R^{18}$ or $R^{19}$ is a covalent bond linking the ligand to a linker;

each X is independently a linker of the formula:

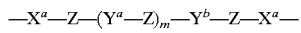

wherein m is an integer of from 0 to 20;

$X^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;

$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)$_n$CR'R"—, —S(O)n—NR'—, —S—S— and a covalent bond; where n is 0, 1 or 2; and R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

p is an integer of from 2 to 10;

q is an integer of from 1 to 20, provided that q is less than p;

and further wherein the distance between ligands is at least 10 Å;

and pharmaceutically-acceptable salts thereof.

6. A pharmaceutical composition comprising a pharmaceutically acceptable carrier and an effective amount of a compound of formula II:

   II wherein each L' is a ligand independently selected from the group consisting of:

(a) a ligand of formula IIA:

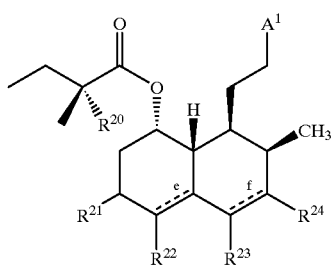

wherein $A^1$ is selected from the group consisting of:

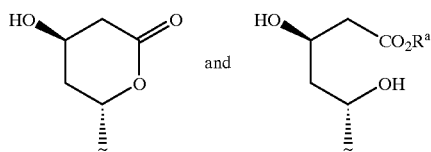

where $R^a$ is selected from the group consisting of hydrogen, lower alkyl and a pharmaceutically-acceptable cation;

$R^{21}$ is selected from the group consisting of hydrogen, lower alkyl, hydroxy and a covalent bond attaching the ligand to a linker;

$R^{22}$, $R^{23}$ and $R^{24}$ are independently selected from the group consisting of hydrogen and a covalent bond attaching the ligand to a linker; and e and f represent optional double bonds;

provided that one of $R^{21}$, $R^{22}$, $R^{23}$ or $R^{24}$ is a covalent bond linking the ligand to a linker;

(b) a ligand of formula IIB:

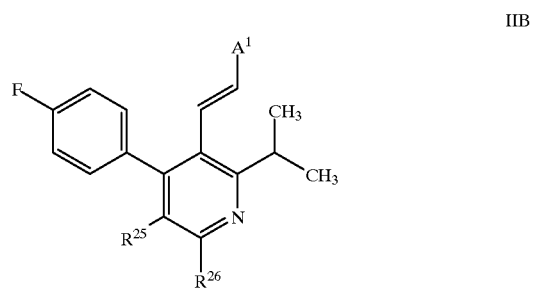

wherein $A^1$ is as defined above;

$R^{25}$ is selected from the group consisting of hydrogen, alkyl, alkoxyalkyl and a covalent bond attaching the ligand to a linker; and $R^{26}$ is selected from the group consisting of hydrogen, alkyl, cycloalkyl and a covalent bond attaching the ligand to a linker;

provided that one of $R^{25}$ or $R^{26}$ is a covalent bond linking the ligand to a linker;

(c) a ligand of formula IIC:

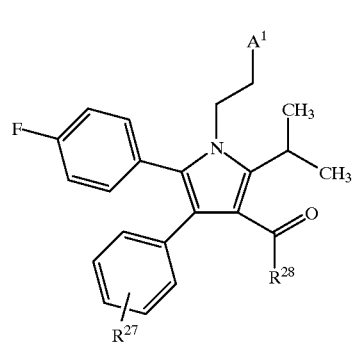

wherein $A^1$ is as defined above;

$R^{27}$ is selected from the group consisting of hydrogen and a covalent bond attaching the ligand to a linker; and R²⁸ is selected from the group consisting of amino, substituted amino and a covalent bond attaching the ligand to a linker;

provided that one of R²⁷ or R²⁸ is a covalent bond linking the ligand to a linker; and (d) a ligand of formula IID:

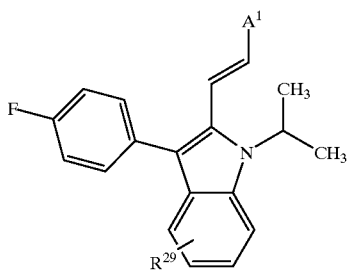

IID wherein

A¹ is as defined above; and

R²⁹ is a covalent bond attaching the ligand to a linker;

X' is a linker of the formula:

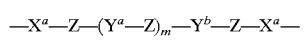

wherein m is an integer of from 0 to 20;

X^a at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;

Y^a and Y^b at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)_nCR'R"—, —S(O)_n—NR'—, —S—S— and a covalent bond; where n is 0, 1 or 2; and R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

and further wherein the distance between ligands is at least 10 Å;

and pharmaceutically-acceptable salts thereof.

7. A pharmaceutical composition comprising a pharmaceutically acceptable carrier and an effective amount of a compound of formula III:

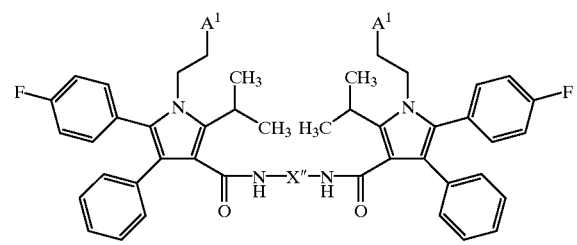

III wherein each A¹ is independently selected from the group consisting of:

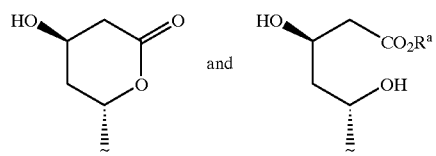

where R^a is selected from the group consisting of hydrogen, lower alkyl and a pharmaceutically-acceptable cation; and X" is a linker of the formula:

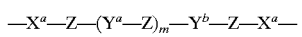

wherein m is an integer of from 0 to 20;

X^a at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;

Y^a and Y^b at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)_nCR'R"—, —S(O)_n—NR'—, —S—S— and a covalent bond; where n is 0, 1 or 2; and R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

and further wherein the distance between ligands is at least 10 Å;

and pharmaceutically-acceptable salts thereof.

8. A pharmaceutical composition comprising a pharmaceutically acceptable carrier and an effective amount of a compound of formula IV:

IV

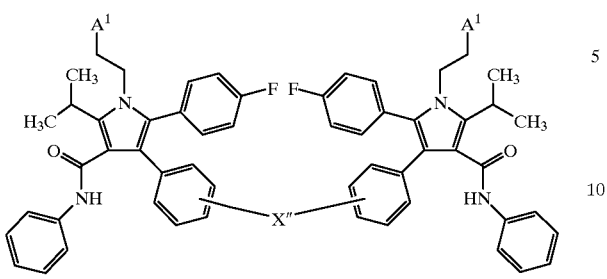

wherein
each A¹ is independently selected from the group consisting of:

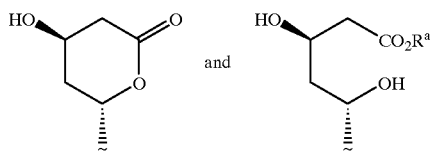
and where $R^a$ is selected from the group consisting of hydrogen, lower alkyl and a pharmaceutically-acceptable cation; and
X" is a linker of the formula:

$$-X^a-Z-(Y^a-Z)_m-Y^b-Z-X^a-$$

wherein m is an integer of from 0 to 20;

$X^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;

$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)$_n$CR'R"—, —S(O)$_n$—NR'—, —S—S— and a covalent bond; where n is 0, 1 or 2; and R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

and further wherein the distance between ligands is at least 10 Å; and pharmaceutically-acceptable salts thereof.

* * * * *